(12) United States Patent
Eshhar et al.

(10) Patent No.: US 12,139,522 B2
(45) Date of Patent: Nov. 12, 2024

(54) T-CELLS COMPRISING TWO DIFFERENT CHIMERIC ANTIGEN RECEPTORS AND USES THEREOF

(71) Applicants: THE MEDICAL RESEARCH INFRASTRUCTURE AND HEALTH SERVICES FUND OF THE TEL AVIV MEDICAL CENTER, Tel Aviv (IL); YEDA RESEARCH AND DEVELOPMENT CO. LTD., Tel Aviv (IL)

(72) Inventors: Zelig Eshhar, Tel Yitzhak (IL); Tova Waks, Petach Tikva (IL); Anat Globerson Levin, Tel Aviv (IL); Naamit Deshet-Unger, Ramat Gan (IL); Moran Rawet Slobodkin, Tel Aviv (IL); Dan Grisaru, Herzlia (IL); Ben Zion Katz, Rehovot (IL); Ido Laskov, Tel Aviv (IL)

(73) Assignees: THE MEDICAL RESEARCH INFRASTRUCTURE AND HEAL SERVICED FUND OF THE TEL AVIV MEDECAL CENTER, Tel Aviv (IL); YEDA RESEARCH AND DEVELOPMENT CO. LTD., Tel Aviv (IL)

( * ) Notice: Subject to any disclaimer, the term of this patent is extended or adjusted under 35 U.S.C. 154(b) by 1166 days.

(21) Appl. No.: 16/769,867

(22) PCT Filed: Dec. 4, 2018

(86) PCT No.: PCT/IL2018/051326
§ 371 (c)(1),
(2) Date: Jun. 4, 2020

(87) PCT Pub. No.: WO2019/111250
PCT Pub. Date: Jun. 13, 2019

(65) Prior Publication Data
US 2021/0300986 A1  Sep. 30, 2021

Related U.S. Application Data

(60) Provisional application No. 62/594,577, filed on Dec. 5, 2017, provisional application No. 62/668,826, filed on May 9, 2018.

(51) Int. Cl.
| | | |
|---|---|---|
| C07K 14/725 | (2006.01) | |
| A61K 35/17 | (2015.01) | |
| C07K 16/28 | (2006.01) | |
| C07K 16/32 | (2006.01) | |
| A61K 38/00 | (2006.01) | |

(52) U.S. Cl.
CPC .......... *C07K 14/7051* (2013.01); *A61K 35/17* (2013.01); *C07K 16/2896* (2013.01); *C07K 16/32* (2013.01); *A61K 38/00* (2013.01); *C07K 2317/622* (2013.01); *C07K 2319/33* (2013.01)

(58) Field of Classification Search
CPC ........................ C07K 16/2896; C07K 16/32; C07K 14/7051; A61K 35/17; A61K 39/464; A61K 39/4644–464499
See application file for complete search history.

(56) References Cited

U.S. PATENT DOCUMENTS

| | | | |
|---|---|---|---|
| 7,829,673 B2 | 11/2010 | De Weers | |
| 8,614,301 B2 * | 12/2013 | Arber ...................... | A61P 35/00 530/387.3 |
| 9,221,914 B2 | 12/2015 | Kraus | |
| 2014/0099309 A1 * | 4/2014 | Powell, Jr. ............. | C07K 16/28 435/328 |
| 2015/0342993 A1 * | 12/2015 | Kloss ..................... | A61P 37/04 435/325 |
| 2018/0305433 A1 | 10/2018 | Pulé | |

FOREIGN PATENT DOCUMENTS

| | | |
|---|---|---|
| CA | 2958672 A1 | 12/2008 |
| CN | 107326014 A | 11/2017 |
| WO | 2014055668 A1 | 4/2014 |
| WO | 2014138704 A1 | 9/2014 |
| WO | 2014152177 A1 | 9/2014 |
| WO | 2015142314 A1 | 9/2015 |
| WO | 2015142675 A2 | 9/2015 |
| WO | 2016130598 A1 | 8/2016 |
| WO | 2016210293 A1 | 12/2016 |
| WO | 2016210447 A1 | 12/2016 |

(Continued)

OTHER PUBLICATIONS

Fesnak et al., Nature Reviews Cancer, 16:566-581 (Year: 2016).*
Geldres et al., Sem Immunol 28:3-9 (Year: 2016).*
Hanada & Restifo, "News & Views" Nat. Biotech. 31:71-76 (Year: 2013).*
Sadelain et al., Cancer Disc 3:388-98 (Year: 2013).*
Finlay & Almagro, Front. Immunol. vol. 3, doi: 10.3389/fimmu. 2012.00342, pp. 1-18 (Year: 2012).*
Ayed et al., (2015) Immunotherapy for multiple myeloma: Current status and future directions. Critical Reviews in Oncology/Hematology 96(3): 399-412.

(Continued)

*Primary Examiner* — Jessica H Roark
(74) *Attorney, Agent, or Firm* — Dorsey & Whitney LLP

(57) ABSTRACT

The present invention provides T-cells modified to express at least two chimeric antigen receptors, wherein one of the CARs binds specifically to an antigen selected from CD138, HER2 and CD24 and another CAR binds specifically a different antigen selected from CD 138, HER2 and CD24. Further, the invention provides pharmaceutical compositions comprising these CAR T-cells and their use in treatment of cancer, in particular, ovarian cancer, DNA constructs encoding said CARs and methods for preparation of T-cells expressing said CARs.

18 Claims, 3 Drawing Sheets

Specification includes a Sequence Listing.

(56) References Cited

FOREIGN PATENT DOCUMENTS

| | | | |
|---|---|---|---|
| WO | 2017025323 A1 | 2/2017 | |
| WO | 2017027291 A1 | 2/2017 | |
| WO | 2017149515 A1 | 9/2017 | |
| WO | 2018144535 A1 | 8/2018 | |
| WO | 2019111249 A1 | 6/2019 | |
| WO | 2020261280 A1 | 12/2020 | |

OTHER PUBLICATIONS

Chang et al., (2015) Abstract 3149: Chimeric antigen receptor-modified T cells against several target antigens in multiple myeloma. Proceedings: AACR 106th Annual Meeting 2015; Apr. 18-22, 2015; Philadelphia, PA. Aug. 1, 2015 (Aug. 1, 2015). Retrieved from the Internet: URL: https://cancerres.aacrjournals.org/content/75/15_Supplement/3149.

Globerson et al., (2020) Treatment of Multiple Myeloma Using Chimeric Antigen Receptor T Cells with Dual Specificity. Cancer Immunol Res 8(12): 1485-1495.

Guo et al., (2016) CD138-directed adoptive immunotherapy of chimeric antigen receptor (CAR)-modified T cells for multiple myeloma. Journal of Cellular Immunotherapy 2(1): 28-35.

Lanitis et al., (2012) Primary human ovarian epithelial cancer cells broadly express HER2 at immunologically-detectable levels. PLoS One 7(11): e49829; 12 pages.

Lanitis et al., (2013) Chimeric antigen receptor T Cells with dissociated signaling domains exhibit focused antitumor activity with reduced potential for toxicity in vivo. Cancer Immunol Res. Author manuscript; available in PMC Jul. 1, 2014. Published in final edited form as: Cancer Immunol Res. Jul. 1, 2013; 1(1): 43-53.

Orecchia et al., (2013) A novel human anti-syndecan-1 antibody inhibits vascular maturation and tumour growth in melanoma. Eur J Cancer 49(8): 2022-2033.

Salnikov et al., (2013) Antibody targeting of CD24 efficiently retards growth and influences cytokine milieu in experimental carcinomas. Br J Cancer 108(7): 1449-1459.

Sun et al., (2014) Construction and evaluation of a novel humanized HER2-specific chimeric receptor. Breast Cancer Res 16(3): R61; 10 pages.

Zhu et al., (2017) CAR-T cell therapy in ovarian cancer: from the bench to the bedside. Oncotarget 8(38): 64607-64621.

Can-Can et al., (2021) Off-target effect and optimization of CAR-T cell therapy in solid tumors. Chinese Journal of Immunology 37: 2754-2758. Abstract.

Hao He and Wang Zhiyu (2017) Off-target effects of CAR-T cells in tumor therapy and prevention strategies. Chinese Journal of Cancer Biotherapy 24: 317-322. Translated abstract.

Lanitis et al., (2013) Chimeric antigen receptor T Cells with dissociated signaling domains exhibit focused antitumor activity with reduced potential for toxicity in vivo. Cancer Immunol Res 1(1): 43-53.

Ahmed et al., (2015) Human Epidermal Growth Factor Receptor 2 (HER2)-Specific Chimeric Antigen Receptor-Modified T Cells for the Immunotherapy of HER2-Positive Sarcoma. J Clin Oncol 33(15): 1688-1696.

Aigner et al., (1997) CD24, a mucin-type glycoprotein, is a ligand for P-selectin on human tumor cells. Blood 89(9): 3385-3395.

Ali et al., (2016) T cells expressing an anti-B-cell maturation antigen chimeric antigen receptor cause remissions of multiple myeloma. Blood 128(13): 1688-1700.

Atanackovic et al., (2016) Chimeric Antigen Receptor (CAR) therapy for multiple myeloma. Br J Haematol 172(5): 685-698.

Baldwin et al., (2012) Ten-year relative survival for epithelial ovarian cancer. Obstet Gynecol 120(3): 612-618.

Bhattacharyya et al., (2012) T-cell immunotherapy with a chimeric receptor against CD38 is effective in eradicating chemotherapy-resistant B-cell lymphoma cells overexpressing survivin induced by BMI-1. Blood Cancer J 2(6): e75; 3 pages.

Campana et al., (2000) CD38 in hematopoiesis. Chem Immunol 75: 169-188.

Carpenter et al., (2013) B-cell maturation antigen is a promising target for adoptive T-cell therapy of multiple myeloma. Clin Cancer Res 19(8): 2048-2060.

Chen et al., (2018) A compound chimeric antigen receptor strategy for targeting multiple myeloma. Leukemia 32(2): 402-412.

Cohen (2018) CAR T Cells and Other Cellular Therapies for Multiple Myeloma: 2018 Update. Am Soc Clin Oncol Educ Book 38: e6-e15.

Cohen et al., (2019) B cell maturation antigen-specific CAR T cells are clinically active in multiple myeloma. J Clin Invest 129(6): 2210-2221.

Danhof et al., (2018) CARs and other T cell therapies for MM: The clinical experience. Best Pract Res Clin Haematol. Author manuscript; available in PMC Jul. 1, 2019. Published in final edited form as: Best Pract Res Clin Haematol. Jun. 2018; 31(2): 147-157.

De Felipe et al., (1999) Use of the 2A sequence from foot-and-mouth disease virus in the generation of retroviral vectors for gene therapy. Gene Ther 6(2): 198-208.

Deaglio et al., (2001) Human CD38: a (r)evolutionary story of enzymes and receptors. Leuk Res 25(1): 1-12.

Deshet-Unger et al., "Targeting Ovarian Cancer Using Double Car T Cells". Poster Presented at EACR-AACR-ISCR Conference: The Cutting Edge of Contemporary Cancer Research. Oct. 9-11, 2018, Jerusalem, Israel. 1 page.

Deterre et al., (2000) CD38 in T- and B-cell functions. Chem Immunol 75: 146-168.

Drent et al., (2016) Pre-clinical evaluation of CD38 chimeric antigen receptor engineered T cells for the treatment of multiple myeloma. Haematologica 101(5): 616-625.

Eshhar et al., (2014) The emergence of T-bodies/CAR T cells. Cancer J 20(2): 123-126.

Fedorov et al., (2014) Novel approaches to enhance the specificity and safety of engineered T cells. Cancer J 20(2): 160-165.

Fonseca and Monge (2013) Myeloma: classification and risk assessment. Semin Oncol 40(5): 554-566.

Gauthier and Yakoub-Agha (2017) Chimeric antigen-receptor T-cell therapy for hematological malignancies and solid tumors: Clinical data to date, current limitations and perspectives. Curr Res Transl Med 65(3): 93-102.

Globerson Levin; "CAR T Cells Promising Immunotherapy for Cancer; From Basic Research to Cancer Treatment". Presented at the 2nd Annual Next Gen Immuno Oncology Congress 2018, London. 31 pages.

Globerson-Levin et al., (2014) Elimination of progressive mammary cancer by repeated administrations of chimeric antigen receptor-modified T cells. Mol Ther 22(5): 1029-1038.

Goff et al., (2000) Ovarian carcinoma diagnosis: Results of a National Ovarian Cancer Survey. Cancer 89(10): 2068-2075.

Gross and Eshhar (1992) Endowing T cells with antibody specificity using chimeric T cell receptors. FASEB J 6(15): 3370-3378.

Gross and Eshhar (2016) Therapeutic Potential of T Cell Chimeric Antigen Receptors (CARs) in Cancer Treatment: Counteracting Off-Tumor Toxicities for Safe CAR T Cell Therapy. Annu Rev Pharmacol Toxicol 56: 59-83.

Hasegawa and Hosen (2019) Chimeric antigen receptor T cell therapy for multiple myeloma. Inflamm Regen 39: 10; 5 pages.

Helpman et al., (2009) Systematic antigenic profiling of hematopoietic antigens on ovarian carcinoma cells identifies membrane proteins for targeted therapy development. Am J Obstet Gynecol 201(2): 196.e1-196.e7.

Jackson et al., (1992) CD24, a signal-transducing molecule expressed on human B cells, is a major surface antigen on small cell lung carcinomas. Cancer Res 52(19): 5264-5270.

Jayson et al., (2014) Ovarian cancer. Lancet 384(9951): 1376-1388.

Kloss et al., (2013) Combinatorial antigen recognition with balanced signaling promotes selective tumor eradication by engineered T cells. Nat Biotechnol 31(1): 71-75.

Kristiansen et al., (2010) Molecular and clinical dissection of CD24 antibody specificity by a comprehensive comparative analysis. Lab Invest 90(7): 1102-1116.

(56) References Cited

OTHER PUBLICATIONS

Lee et al., (2018) An APRIL-based chimeric antigen receptor for dual targeting of BCMA and TACI in multiple myeloma. Blood 131(7): 746-758.
Liegel et al., (2018) Cellular immunotherapy as a therapeutic approach in multiple myeloma. Accepted manuscript; published as: Expert Rev Hematol 11(7): 525-536; 40 pages.
Maliar et al., (2012) Redirected T cells that target pancreatic adenocarcinoma antigens eliminate tumors and metastases in mice. Gastroenterology 143(5): 1375-1384.
Morgan et al., (2010) Case report of a serious adverse event following the administration of T cells transduced with a chimeric antigen receptor recognizing ERBB2. Mol Ther 18(4): 843-851.
Perez-Amill et al., (2018) CAR-T Cell Therapy: A Door Is Open to Find Innumerable Possibilities of Treatments for Cancer Patients. CAR-T Hücre Tedavisi: Kanser Hastalarına Sayısız Tedavi Olanağı Bulunmasıiçin Kapı Aralandı. Turk J Haematol 35(4): 217-228.
Raje et al., (2019) Anti-BCMA CAR T-Cell Therapy bb2121 in Relapsed or Refractory Multiple Myeloma. N Engl J Med 380(18): 1726-1737.
Richardson et al., (2011) Monoclonal antibodies in the treatment of multiple myeloma. Br J Haematol 154(6): 745-754.
Rousseau et al., (2012) Dosimetry results suggest feasibility of radioimmunotherapy using anti-CD138 (B-B4) antibody in multiple myeloma patients. Tumour Biol 33(3): 679-688.
Ruella et al., (2016) Dual CD19 and CD123 targeting prevents antigen-loss relapses after CD19-directed immunotherapies. J Clin Invest 126(10): 3814-3826.
Shubinsky and Schlesinger (1997) The CD38 lymphocyte differentiation marker: new insight into its ectoenzymatic activity and its role as a signal transducer. Immunity 7(3): 315-324.
Smith et al., (2019) GPRC5D is a target for the immunotherapy of multiple myeloma with rationally designed CAR T cells. Sci Transl Med 11(485): eaau7746; 15 pages.
Sun et al., (2019) Safety and efficacy of targeting CD138 with a chimeric antigen receptor for the treatment of multiple myeloma. Oncotarget 10(24): 2369-2383.
Tenca et al., (2003) Death of T cell precursors in the human thymus: a role for CD38. Int Immunol 15(9): 1105-1116.
Touzeau and Moreau (2017) Daratumumab for the treatment of multiple myeloma. Accepted manuscript; published as: Expert Opin Biol Ther 17(7): 887-893. 18 pages.
Weber et al., (1993) Antibodies to the protein core of the small cell lung cancer workshop antigen cluster-w4 and to the eucocyte workshop antigen CD24 recognize the same short protein sequence leucine-alanine-proline. Clin Exp Immunol 93(2): 279-285.
Yang and Yi (2011) Therapeutic monoclonal antibodies for multiple myeloma: an update and future perspectives. Am J Blood Res 1(1): 22-33.
Zhang et al., (2017) Application of chimeric antigen receptor-engineered T cells in ovarian cancer therapy. Immunotherapy 9(10): 851-861.
Database clinical trials [online] NIH. Lung-Ji Chang; Multi-CAR T Cell Therapy in the Treatment of Multiple Myeloma. ClinicalTrials.gov Identifier: NCT03271632. <URL: https://clinicaltrials.gov/ct2/show/study/NCT03271632>.
IMGT/2Dstructure-DB card for INN 9486. Retrieved from: https://web.archive.org/web/20150424173255/http://www.imgt.org/3Dstructure-DB/cgi/details.cgi?pdbcode=9486 [dated Apr. 24, 2015], on Oct. 29, 2020. 4 pages.
IMGT/2Dstructure-DB card for INN 9128. Retrieved from: https://web.archive.org/web/20150425031816/http://www.imgt.org/3Dstructure-DB/cgi/details.cgi?pdbcode=9128 [dated Apr. 25, 2015], on Oct. 29, 2020. 4 pages.
UniProtKB/Swiss-Prot: P18827.2; RecName: Full=Syndecan-1; Short=SYND1; AltName: CD_antigen=CD138; Flags: Precursor. Dated Apr. 14, 2009 (Apr. 14, 2009); retrieved from: https://www.ncbi.nlm.nih.gov/protein/P18827.2 on Oct. 29, 2020. 4 pages.
UniProtKB/Swiss-Prot: P25063.2; RecName: Full=Signal transducer CD24; AltName: Full=Small cell lung carcinoma cluster 4 antigen; AltName: CD_antigen=CD24; Flags: Precursor. Dated Feb. 28, 2018 (Feb. 28, 2018); retrieved from: https://www.ncbi.nlm.nih.gov/protein/P25063.2 on Oct. 29, 2020. 4 pages.
Bhattacharya et al., (2017) Impact of genetic variation on three dimensional structure and function of proteins. PLoS One 12(3): e0171355.
Bork (2000) Powers and pitfalls in sequence analysis: the 70% hurdle. Genome Res 10(4): 398-400.
Bork and Bairoch (1996) Go hunting in sequence databases but watch out for the traps. Trends Genet 12(10): 425-427.
Brenner (1999) Errors in genome annotation. Trends Genet 15(4): 132-133.
Brorson et al., (1999) Mutational analysis of avidity and fine specificity of anti-levan antibodies. J Immunol 163(12): 6694-6701.
Brummell et al., (1993) Probing the combining site of an anti-carbohydrate antibody by saturation-mutagenesis: role of the heavy-chain CDR3 residues. Biochemistry 32(4): 1180-1187. Abstract.
Burks et al., (1997) In vitro scanning saturation mutagenesis of an antibody binding pocket. Proc Natl Acad Sci U S A 94(2): 412-417.
Casset et al., (2003) A peptide mimetic of an anti-CD4 monoclonal antibody by rational design. Biochem Biophys Res Commun 307(1): 198-205.
Chen et al., (1999) Selection and analysis of an optimized anti-VEGF antibody: crystal structure of an affinity-matured Fab in complex with antigen. J Mol Biol 293(4): 865-881.
Colman (1994) Effects of amino acid sequence changes on antibody-antigen interactions. Res Immunol 145(1): 33-36.
De Pascalis et al., (2002) Grafting of "abbreviated" complementarity-determining regions containing specificity-determining residues essential for ligand contact to engineer a less immunogenic humanized monoclonal antibody. J Immunol 169(6): 3076-3084.
Doerks et al., (1998) Protein annotation: detective work for function prediction. Trends Genet 14(6): 248-250.
Fenton et al., (2020) Rheostat positions: A new classification of protein positions relevant to pharmacogenomics. Med Chem Res 29(7): 1133-1146.
Guo et al., (2004) Protein tolerance to random amino acid change. Proc Natl Acad Sci U S A 101(25): 9205-9210.
Holm et al., (2007) Functional mapping and single chain construction of the anti-cytokeratin 8 monoclonal antibody TS1. Mol Immunol 44(6): 1075-1084.
Jang et al., (1998) The structural basis for DNA binding by an anti-DNA autoantibody. Mol Immunol 35(18): 1207-1217.
Kobayashi et al., (1999) Tryptophan H33 plays an important role in pyrimidine (6-4) pyrimidone photoproduct binding by a high-affinity antibody. Protein Eng 12(10): 879-884.
MacCallum et al., (1996) Antibody-antigen interactions: contact analysis and binding site topography. J Mol Biol 262(5): 732-745.
Ngo et al., (1994) Computational Complexity, Protein Structure Prediction, and the Levinthal Paradox. In: Merz, K.M., Le Grand, S.M. (eds) The Protein Folding Problem and Tertiary Structure Prediction. Birkhäuser Boston; pp. 492-495.
Paul, William E., Fundamental Immunology, 3rd Edition, Raven Press, New York, Chapt. 8, pp. 292-295 (1993).
Rudikoff et al., (1982) Single amino acid substitution altering antigen-binding specificity. Proc Natl Acad Sci U S A 79(6): 1979-1983.
Sela-Culang et al., (2013) The structural basis of antibody-antigen recognition. Front Immunol 4: 302 (13 total pages).
Sherbenou et al., (2015) The development of potential antibody-based therapies for myeloma. Blood Rev. Author manuscript; available in PMC Jun. 26, 2015. Published in final edited form as: Blood Rev. Mar. 2015; 29(2): 81-91.
Skolnick and Fetrow (2000) From genes to protein structure and function: novel applications of computational approaches in the genomic era. Trends Biotechnol 18(1): 34-39.
Smith and Zhang (1997) The challenges of genome sequence annotation or "the devil is in the details". Nat Biotechnol 15(12): 1222-1223.
Stevenson (2006) CD38 as a therapeutic target. Mol Med 12(11-12): 345-346.
Tokuriki and Tawfik (2009) Stability effects of mutations and protein evolvability. Curr Opin Struct Biol 19(5): 596-604.

(56) References Cited

OTHER PUBLICATIONS

Vajdos et al., (2002) Comprehensive functional maps of the antigen-binding site of an anti-ErbB2 antibody obtained with shotgun scanning mutagenesis. J Mol Biol 320(2): 415-428.

Vasudevan et al., (2004) A single amino acid change in the binding pocket alters specificity of an anti-integrin antibody AP7.4 as revealed by its crystal structure. Blood Cells Mol Dis 32(1): 176-181.

Wells (1990) Additivity of mutational effects in proteins. Biochemistry 29(37): 8509-8517.

Wilkie et al., (2012) Dual targeting of ErbB2 and MUC1 in breast cancer using chimeric antigen receptors engineered to provide complementary signaling. J Clin Immunol 32(5): 1059-1070.

Wu et al., (1999) Humanization of a murine monoclonal antibody by simultaneous optimization of framework and CDR residues. J Mol Biol 294(1): 151-162.

Zhang et al., (2015) Comprehensive optimization of a single-chain variable domain antibody fragment as a targeting ligand for a cytotoxic nanoparticle. MAbs 7(1): 42-52.

Newick et al., (2016) Chimeric antigen receptor T-cell therapy for solid tumors. Molecular Therapy—Oncolytics 3: 16006; 7 pages.

Tchou et al., (2017) Safety and Efficacy of Intratumoral Injections of Chimeric Antigen Receptor (CAR) T Cells in Metastatic Breast Cancer. Cancer Immunol Res 5(12): 1152-1161.

Lefranc (1997) Unique database numbering system for immunogenetic analysis. Immunol Today 18(11): 509.

Database clinical trials [online] NIH. Zhujiang Hospital; CAR-T Cells Therapy in Relapsed/Refractory Multiple Myeloma (MM). ClinicalTrials.gov Identifier: NCT03473496. <URL: <https://clinicaltrials.gov/ct2/show/NCT03473496> Apr. 18, 2018. 8 pages.

\* cited by examiner

T-CELLS COMPRISING TWO DIFFERENT CHIMERIC ANTIGEN RECEPTORS AND USES THEREOF

CROSS-REFERENCE TO RELATED APPLICATIONS

This application is a U.S. Nationalization of PCT International Application No. PCT/IL2018/051326 filed Dec. 4, 2018, which claims benefit to U.S. Provisional Application No. 62/594,577 filed Dec. 5, 2017 and U.S. Provisional Application No. 62/668,826 filed May 9, 2018, the disclosure of each of which is hereby incorporated by reference in its entirety.

FIELD OF THE INVENTION

The present inventions relates to T-cells expressing at least two different chimeric antigen receptors binding to at least two different antigens selected from CD138, CD24 and HER2, pharmaceutical compositions comprising said cells, and their use in treating cancer, in particular to use in treating ovarian cancer.

SEQUENCE LISTING

The instant application contains a Sequence Listing which has been submitted electronically and in .txt format and is hereby incorporated by reference in its entirety. Said sequence listing file, created on 18 Jan. 2024, is named 2024-01-18_Corrected_Sequence_Listing SMC-014 US.txt and is 51,372 bytes in size.

BACKGROUND OF THE INVENTION

Chimeric antigen receptor T-cell (CAR-T) therapy is a newly developed adoptive antitumor treatment. Genetically modified T cells express chimeric antigen receptors, which generally consist of a signaling end domain, a CD3-zeta or gamma chain from the FcR transmembrane domain and an extracellular single-chain variable fragment (scFv) derived from a monoclonal antibody which gives the receptor specificity for a tumor-associated antigen on a target malignant cell. Upon binding the tumor-associated antigen via the chimeric antigen receptor, the chimeric antigen receptor expressed on T cell (CAR T-cell) mounts an immune response that is cytotoxic to the malignant cell. Theoretically, CAR-T cells can specifically localize and eliminate tumor cells by interacting with the tumor-associated antigens (TAAs) expressed on tumor cell surface.

Despite the fast growth in the field, the development of efficient and safe CAR-T treatment encounters in many challenges. Many known and numerous yet unidentified factors are likely to contribute to the variability observed in clinical responses across trials and also between individual patients. The factors that have to be considered are for example in vivo fate of the T-cells, properties of a tumor and safety. To improve the safety and efficacy it was suggested to generate T-cells transduced with a CAR that provides suboptimal activation upon binding to one antigen and a chimeric costimulatory receptor that recognizes a second antigen (Kloss et al., 2013, Nature Biotechnology, 13, 71-75, WO 2014/055668 and WO 2015/142314). Additional factor, which is always one of the major obstacles when cancer treatment is concerned, is the choice of the target(s). Truly tumor specific surface antigens are hardly identified, and the implementation of effective mechanisms to mitigate life threatening and unexpected off-target toxicities is crucial.

Epithelial ovarian cancer (EOC) is the deadliest of all gynecological malignancies. Known as "the cancer that whispers", EOC often does not present any symptoms in its early stages, and therefore the majority of patients are diagnosed at an advanced stage of the disease. While significant progress has been made in the surgical and chemotherapeutic treatments for EOC, the survival rates for this disease have only modestly improved. Approximately 80% of women diagnosed with advanced-stage cancer suffer from disease recurrence, with a 5-year survival of approximately 30%.

Standard treatment includes debulking surgery and chemotherapy with platinum- and taxane-based agents. Response rates are around 75%, however, 75% of patients will have a recurrence with 25%, 40% and 70% of recurrences occurring within 12, 24, and 36 months, respectively.

Multiple recurrences and the chronic aspect of this disease leads patients to be exposed to multiple lines of chemotherapy, with decreasing response rates, and shorter progression free survival and survival with each line of chemotherapy.

Targeted therapies are the newest options for tubo-ovarian cancer treatment. In ideal, targeted therapies use drugs or substances that identify and attack cancer cells while doing little damage to normal cells. One of such treatments is Bevacizumab, an antibody that binds and inhibits a substance called vascular endothelial growth factor and consequently prevent angiogenesis. Other treatment are Olaparib (Lynparza), rucaparib (Rubraca), and niraparib (Zejula), untibodies targeting and inhibiting poly(ADP)-ribose polymerase, involved in one pathway to help repair damaged DNA inside cells.

Although CAR-T therapy could, in principle, overcome some of the problems of the "classic" and novel treatments of ovarian cancer, the major roadblock in development of CAR T-cells therapy is their substantial on-target off-tissue toxicity. Only a few proteins and cell surface antigens, are exclusively expressed by malignant cells, resulting in the undesired targeting of healthy tissues. Therefore, the search for antigens specifically expressed on tumor cells only has become a central objective in identifying CAR targets in ovarian cancer. Zhang, Zhang and Shi (Immunotherapy, 2017, 9(10), 851-861) review the progress of CAR T-cell therapy of ovarian cancer. Zhang describes several targets antigen on the ovarian cancer cells that serve as a target for development of CAR-T cells. These antigen include Folate receptor-α, Mesothelin, EGFR, Her2, CD70, CD133, PSMA, NKG2DLs, MUC-2 and MUC-16. For some of these antigens clinical trials are being currently conducted.

CD138 is a surface protein, which functions as an adhesion molecule binding to the extracellular matrix molecules collagen and fibronectin. Anti-CD138 antibodies were previously described, for example in U.S. Pat. No. 9,221,914. Despite the fact that CD138 is considered as one of the most promising markers, in a phase I/II study with immunoconjugate BT062 used as a single agent, only 1 out of 23 patients showed an objective clinical response (Atanackovic et al.). Moreover, CD138 is expressed on many mature epithelial cells. Indeed liver and skin toxicity was observed in those clinical trials indicating that significant side effects of CAR-T treatment directing CD138 may be expected.

Human epidermal growth factor receptor 2 (HER2) is a member of the epidermal growth factor receptor family having tyrosine kinase activity. Dimerization of the receptor results in the autophosphorylation of tyrosine leading to cell proliferation and tumorigenesis. Overexpression of HER2 occurs in breast cancers, gastric/gastroesophageal cancers, ovary and other solid tumors. HER2 overexpression is associated with poor clinical outcomes. HER2-CAR T cells against glioblastoma provide initial evidence of the safety and antitumor activity of CAR T cell immunotherapy in patients with malignant brain tumors. (Ahmed N. et al. 2015). Eshhars lab, have already published work using CAR T cells with N29 (anti Her2) (Globerson-Levin A, Waks T and, Eshhar Z) Mol Ther. 2014 May; 22(5):1029-38. Clinical trials using anti-Her2 CAR was reported with mortality as for toxicity against normal tissues and cytokine storm (Morgan et al., Mol Ther. 2010 April; 18(4):843-51).

CD24 is a small, heavily glycosylated mucin-like cell surface protein that binds to the membrane via a glycosylphosphatidylinositol anchor. Under physiological conditions, CD24 was initially identified as a B cell marker granulocytes keratinocytes and renal tubules. Under pathological conditions, CD24 plays an important role in hematologic malignancies and also in various solid tumors such as glioma, small cell lung and breast cancer, and epithelial ovarian. Marial et al., (Gastroenterology. 2012 November; 143(5)) tested the efficacy of CAR-T cell against CD24 for treating pancreatic adenocarcinoma.

Other targets described above also have their merits as well as drawbacks, most of which are related to high level of side effects, that maintains the choice of the target as one of the major obstacles in developing safe and efficient CAR-T therapies. There is an unmet need in rational development of additional CAR-T therapeutic systems allowing long lasting safe treatment of ovarian cancer with fewer off-target side effects.

SUMMARY OF THE INVENTION

It is now disclosed according to the present invention that T-cells genetically modified to express two CARs capable of binding to two different carefully chosen targets on ovarian cancer cells such as HER2, CD138, or CD24, effectively enhanced excretion of interferon upon incubation with different types of cancer cells. Moreover, the specific design of the CAR system, in which one CAR carried only an activation domain and the second CAR carried only a co-stimulating domain, allowed reducing the severity of side effect related to "on target off tumor" biding of the T-cells.

According to one aspect, the present invention provides a T-cell genetically modified to express two distinct separate chimeric antigen receptors (CARs), wherein each one of the two distinct CARs comprises an antigen binding domain that binds specifically an antigen selected from CD138 (anti-CD138 scFv), HER2 (anti-HER2 scFv) and CD24 (anti-CD24 scFv).

According to one aspect, the present invention provides a T-cell genetically modified to express at least two distinct separate chimeric antigen receptors (CARs), wherein the first CAR comprises an antigen binding domain that binds specifically to CD138 and the second CAR comprises an antigen binding domain that binds specifically to HER2. According to some embodiments, the antigen binding domains binding specifically to HER2 or CD138 are single chain variable domains (scFv) of anti-HER2 and anti-CD138 antibodies, respectively. Thus according to one embodiment, the present invention provides a T-cell genetically modified to express two distinct separate chimeric antigen receptors (CARs), wherein the first CAR comprises an anti-CD138 scFv and the second CAR anti-HER2 scFv.

According to another aspect, the present invention provides a T-cell genetically modified to express at least two distinct separate chimeric antigen receptors (CARs), wherein the first CAR comprises an antigen binding domain that binds specifically to CD138 and the second CAR comprises an antigen binding domain that binds specifically to CD24. According to some embodiments, the antigen binding domains binding specifically to CD138 or CD24 are single chain variable domains (scFv) of anti-CD24 and anti-CD138 antibodies, respectively. Thus according to one embodiment, the present invention provides a T-cell genetically modified to express two distinct separate chimeric antigen receptors (CARs), wherein the first CAR comprises an anti-CD138 scFv and the second CAR anti-CD24 scFv.

According to yet another aspect, the present invention provides a T-cell genetically modified to express at least two distinct separate chimeric antigen receptors (CARs), wherein the first CAR comprises an antigen binding domain that binds specifically to HER2 and the second CAR comprises an antigen binding domain that binds specifically to CD24. According to some embodiments, the antigen binding domains binding specifically to HER2 or CD24 are single chain variable domains (scFv) of anti-HER2 and anti-CD138 antibodies, respectively. Thus according to one embodiment, the present invention provides a T-cell genetically modified to express two distinct separate chimeric antigen receptors (CARs), wherein the first CAR comprises an anti-HER2 scFv and the second CAR anti-CD24 scFv.

According to any one of the above aspects and embodiments, at least one of the CARs comprises a costimulatory domain and the other one of the CARs comprises an activation domain. According to one embodiment, the costimulatory domain is a costimulatory domain of CD28, 4-1BB, OX40, iCOS, CD27, CD80, CD70. According to other embodiments, the activation domain is selected from FcRγ and CD3-ζ.

According to some embodiments, the present invention provides an engineered T-cell comprising two chimeric antigen receptors (CARs), wherein the first CAR has the amino acid sequence SEQ ID NO: 10 or being an analog thereof, and the second CAR has the amino acid sequence in SEQ ID NO: 11 or being an analog thereof. According to other embodiments, the present invention provides an engineered T-cell comprising two chimeric antigen receptors (CARs), wherein the first CAR has the amino acid sequence SEQ ID NO: 10 or being an analog thereof, and the second CAR has the amino acid sequence in SEQ ID NO: 12 or being an analog thereof. According to further embodiments, the present invention provides an engineered T-cell comprising two chimeric antigen receptors (CARs), wherein the first CAR has the amino acid sequence SEQ ID NO: 13 or being an analog thereof, and the second CAR has the amino acid sequence in SEQ ID NO: 11 or being an analog thereof.

According to one embodiment, the T-cell is a CD4+ T-cell. According to another embodiment, the T-cell is a CD8+ T-cell. According to any one of the above embodiments, the T-cell expresses the CARs of the present invention.

According to another aspect, the present invention provides a T-cell, comprising at least one copy of one or more DNA constructs encoding the two or more CARs of the present invention. According to one embodiment, the T-cell comprises at least one copy of a DNA construct encoding, from 5' to 3', (i) a leader peptide, (ii) anti-CD138 scFv, (iii) a costimulatory domain, an activation domain or both, (iii) transmembrane domain I, (iv) a self-cleaving peptide, (vi) a leader peptide, (vii) anti-HER2 scFv, (viii) transmembrane domain II and (ix) a costimulatory domain, an activation domain or both.

According to another embodiment, the present invention provides a T-cell, comprising at least one copy of one or more DNA constructs encoding, from 5' to 3': (i) a leader peptide, (ii) anti-CD138 scFv, (iii) a costimulatory domain, an activation domain or both, (iii) transmembrane domain I, (iv) a self-cleaving peptide, (vi) a leader peptide, (vii) anti-CD24 scFv, (viii) transmembrane domain II and (ix) a costimulatory domain, an activation domain or both.

According to a further embodiment, the present invention provides a T-cell, comprising at least one copy of a DNA construct encoding, from 5' to 3': (i) a leader peptide, (ii) anti-HER2 scFv, (iii) a costimulatory domain, an activation domain or both, (iii) transmembrane domain I, (iv) a self-cleaving peptide, (vi) a leader peptide, (vii) anti-CD24 scFv, (viii) transmembrane domain II and (ix) a costimulatory domain, an activation domain or both.

Alternatively the T-cell comprises two different DNA constructs encoding the CARs of the present invention. According to one embodiment, the first DNA construct comprises a sequence encoding, from 5' to 3', (i) a leader peptide, (ii) anti-CD138 scFv, (iii) a transmembrane domain I and (iv) a costimulatory domain, an activation domain or both, and the second DNA construct comprises a sequence encoding, from 5' to 3' (i) a leader peptide, (ii) anti-HER2 scFv, (iii) a transmembrane domain II and (iv) a costimulatory domain, an activation domain or both.

According to another embodiment, the first DNA construct comprises a sequence encoding, from 5' to 3', (i) a leader peptide, (ii) anti-CD138 scFv, (iii) a transmembrane domain I and (iv) a costimulatory domain, an activation domain or both, and the second DNA construct comprises a sequence encoding, from 5' to 3' (i) a leader peptide, (ii) anti-CD24 scFv, (iii) a transmembrane domain II and (iv) a costimulatory domain, an activation domain or both. According to yet another embodiment, the first DNA construct comprises a sequence encoding, from 5' to 3', (i) a leader peptide, (ii) anti-HER2 scFv, (iii) a transmembrane domain I and (iv) a costimulatory domain, an activation domain or both, and the second DNA construct comprises a sequence encoding, from 5' to 3' (i) a leader peptide, (ii) anti-CD24 scFv, (iii) a transmembrane domain II and (iv) a costimulatory domain, an activation domain or both.

According to other embodiments, the present invention provides a T-cell comprising at least one copy of each one of two DNA constructs, wherein the first DNA construct comprises the DNA sequence SEQ ID NO: 24 or a variant thereof and the second DNA construct comprises the DNA sequence SEQ ID NO: 25 or a variant thereof. According to another embodiment, the first DNA construct comprises the DNA sequence SEQ ID NO: 24 or a variant thereof and the second DNA construct comprises the DNA sequence SEQ ID NO: 26 or a variant thereof. According to still another embodiment, the first DNA construct comprises the DNA sequence SEQ ID NO: 27 or a variant thereof and the second DNA construct comprises the DNA sequence SEQ ID NO: 26 or a variant thereof. According to yet another embodiment, the present invention provides a T-cell comprising at least one copy of a DNA construct comprising DNA sequence selected from SEQ ID NO: 21, 22 and 23.

According to a certain aspect, the present invention provides the DNA constructs of the present invention. According to some embodiments, the DNA construct encodes for: (A) from 5' to 3': (i) a leader peptide, (ii) an antigen binding domain selected from anti-CD138, anti-HER2 and anti-CD24 (iii) transmembrane domain I, and (iv) a costimulatory domain, an activation domain or both; and (B) from 5' to 3' (v) a leader peptide, (vi) an antigen binding domain selected from anti-CD138, anti-HER2 and anti-CD24 (vii) transmembrane domain II and (viii) an activation domain, a costimulatory domain or both; wherein (A) and (B) are separated by a self-cleaving peptide, and wherein the an antigen binding domains of (ii) and of (vi) are different. In other embodiments, the present invention provides a DNA construct comprising DNA sequence selected from SEQ ID NO: 21, 22 and 23. On other embodiments, the DNA construct of the present invention consists of DNA sequence selected from SEQ ID NO: 21, 22 and 23

According to another aspect, the present invention provides a pharmaceutical composition comprising the T-cells of the present invention. According to one embodiment, the T-cell is genetically modified to express two CARs of the present invention. According to one embodiment, the T-cell expresses the CARs of the present invention. According to further embodiment, the T-cell comprises a DNA construct encoding the two CARs of the present invention or two or more different constructs encoding the two different CARs of the present invention. According to some embodiments, the pharmaceutical composition of the present invention is for use in treating cancer. According to one embodiment, the cancer is ovarian cancer.

According to another aspect, the present invention provides a method of treating cancer such as ovarian cancer in a subject in need thereof, comprising administering an effective amount of T-cells of the present invention. According to another aspect, the present invention provides a method for preparation of T-cells genetically modified to express at least two distinct separate chimeric antigen receptors (CARs), wherein the first CAR comprises an anti-HER2 scFv and the second CAR comprises an antigen anti-CD138 scFv, said method comprises transfecting T-cells with the DNA construct of the present invention.

BRIEF DESCRIPTION OF THE FIGURES

FIG. 1 shows a scheme of dual-CAR DNA constructs: $V_L$ and $V_H$ are parts of scFv separated by a linker, T2A is a self-cleaving peptide, CD28 refers to a costimulatory element of CD28, and FcRγ is an activator element. FIG. 1B—a construct for Dual αCD138-αCD24 CAR; and FIG. 1C—a construct for Dual αHER2-αCD24 CAR.

FIG. 3—interactions of T-cells transduced with αCD138-αHER2 CAR; FIG. 4—interactions of T-cells transduced with αCD138-αCD24 CAR; FIG. 5—interactions of T-cells transduced with αHER2-αCD24 CAR.

DETAILED DESCRIPTION OF THE INVENTION

Figure 1A:
FIG. 1A—a construct for Dual αCD138-αHER2 CAR.

According to one aspect, the present invention provides a T-cell genetically modified to express at least two distinct and separate chimeric antigen receptors (CARs), wherein the antigen binding domain of one CAR is different from the antigen binding domain of another CAR and wherein the antigen binding domain is selected from anti-CD138, anti-HER2 and anti-CD24 antigen binding domain. Therefore, the T-cell is genetically modified to express at least two different CAR, wherein the antigen binding domains of said distinct CARs are different from each other.

The term "T cell" as used herein refers a lymphocyte of a type produced or processed by the thymus gland that participates in a variety of cell-mediated immune reactions, as well known in art. The term encompasses T-cells transduces with a DNA or RNA polypeptide, optionally using a vector. The T-cells of the present invention are capable of expressing the CAR molecules encoded by the DNA or RNA by which the T-cells are transduced infected or electroporated.

The terms "chimeric antigen receptor" or "CAR" are used herein interchangeably and refer to engineered receptors, i.e. proteins, which are expressed onto cells. In general, a CAR comprises an extracellular domain (extracellular part) comprising the antigen binding domain, a transmembrane domain and an intracellular domain.

The extracellular domain may comprise an antigen binding domain and optionally a spacer or hinge region.

The antigen binding domain of the CAR targets a specific antigen. The targeting regions may comprise full length heavy chain, Fab fragments, or single chain variable fragment (scFv) of an antibody. The antigen binding domain can be derived from the same species or a different species for or in which the CAR will be used in. In one embodiment, the antigen binding domain is a scFv.

The extracellular spacer or hinge region of a CAR is located between the antigen binding domain and a transmembrane domain. Extracellular spacer domains may include, but are not limited to, Fc fragments of antibodies or fragments or derivatives thereof, hinge regions of antibodies or fragments or derivatives thereof, CH2 regions of antibodies, CH3 regions of antibodies, accessory proteins, artificial spacer sequences or combinations thereof.

The term "transmembrane domain" refers to the region of the CAR, which crosses or bridges the plasma membrane. The transmembrane domain of the CAR of the invention is the transmembrane region of a transmembrane protein, an artificial hydrophobic sequence or a combination thereof. According to some embodiments, the term comprises also transmembrane domain together with extracellular spacer or hinge region.

The terms "specifically binds" or "specific for" with respect to an antigen-binding domain of an antibody, of a fragment thereof or of a CAR refers to an antigen-binding domain which recognizes and binds to a specific antigen, but does not substantially recognize or bind other molecules in a sample. The term encompasses that the antigen-binding domain binds to its antigen with high affinity and binds other antigens with low affinity. An antigen-binding domain that binds specifically to an antigen from one species may bind also to that antigen from another species. This cross-species reactivity is not contrary to the definition of that antigen-binding domain as specific.

An intracellular domain may be an intracellular domain of T cell receptor or of any other receptor (e.g., TNFR super-family member) or portion thereof, such as an intracellular activation domain (e.g., an immunoreceptor tyrosine-based activation motif (ITAM)-containing T cell activating motif), an intracellular costimulatory domain, or both.

The terms "genetically modified T cells" of the present invention and "CAR-T cells" are used herein interchangeably.

The terms "HER2" and "human HER2" are used herein interchangeably and refer to the protein known as human epidermal growth factor receptor 2, Receptor tyrosine-protein kinase erbB-2, also known as CD340 (cluster of differentiation 340), proto-oncogene Neu, Erbb2 (rodent), or ERBB2 and has an extension number EC 2.7.10.1. The terms "anti HER2" or "αHER2" refers to an antigen binding domain of an antibody that binds specifically to human HER2. According to one embodiment, antigen binding domain is an antigen binding domain of a CAR. According to another embodiments, the antigen binding domain is a scFv. According to a further embodiment, the antigen binding domain binds to an epitope of the human HER2, and in particular to an epitope of the extracellular domain of the human HER2. According to one embodiment, HER2 is N29. Thus according to one embodiment, the antigen binding domain is an anti-N29 scFv.

The term "CD138" and "human CD138" are used herein interchangeably and refer to the protein known as Syndecan 1, SDC1, CD138, SDC, or SYND1, and having an accession number P18827. The terms "anti CD138" or "αCD138" refers to an antigen binding domain of an antibody that binds specifically to human CD138. According to one embodiment, antigen binding domain is an antigen binding domain of a CAR. According to another embodiments, the antigen binding domain is a scFv. According to a further embodiment, the antigen binding domain binds to an epitope of the human CD138, and in particular to an epitope of the extracellular domain of the human CD138.

The term "CD24" and "human CD24" are used herein interchangeably and refer to the protein known as cluster of differentiation 24 having UniProt accession number P25063. The terms "anti CD24" or "αCD24" refer to an antigen binding domain of an antibody that binds specifically to human CD24. According to one embodiment, antigen binding domain is an antigen binding domain of a CAR. According to another embodiments, the antigen binding domain is a scFv. According to a further embodiment, the antigen binding domain binds to an epitope of the human CD24, and in particular to an epitope of the extracellular domain of the human CD24.

According to some embodiments, the antigen binding domains of the CARs of the present invention are scFv. Thus according to one embodiment, the present invention provides a T-cell genetically modified to express two distinct separate chimeric antigen receptors (CARs), wherein each one of the two distinct CARs comprises a scFv antigen binding domain that binds specifically an antigen selected from CD138 (anti-CD138 scFv), HER2 (anti-HER2 scFv) and CD24 (anti-CD24 scFv).

According to one embodiment, the present invention provides a T-cell genetically modified to express at least two distinct separate chimeric antigen receptors (CARs), wherein the first CAR comprises an antigen binding domain that binds specifically to human CD138 and the second CAR comprises an antigen binding domain that binds specifically to human HER2. According to some embodiments, the antigen binding domain is scFv. Thus according to one embodiment, the present invention provides a T-cell genetically modified to express at least two distinct separate chimeric antigen receptors (CARs), wherein the first CAR comprises an scFv antigen binding domain that binds specifically to human CD138 (anti-CD138 scFv) and the second CAR comprises an scFv antigen binding domain that binds specifically to human HER2 (anti-HER2 scFv).

According to one embodiment, the present invention provides a T-cell genetically modified to express two distinct separate chimeric antigen receptors (CARs), wherein the first CAR comprises anti-CD138 scFv and the second CAR comprises anti-HER2 scFv.

According to any one of the above embodiments, anti-CD138 and anti-HER2 scFv binding domains comprise $V_L$ and $V_H$ domains.

According to any one of the aspects and embodiments of the invention, the terms "peptide comprising the amino acid sequence SEQ ID NO: X", "peptide comprising SEQ ID NO: X" and "peptide having SEQ ID NO: X" are used herein interchangeably. The terms "peptide consisting of the amino acid sequence SEQ ID NO: X", "peptide consisting of SEQ ID NO: X" and "peptide of SEQ ID NO: X" are used herein interchangeably.

According to any one of the above embodiments, the anti-CD138 scFv comprises a $V_L$ domain having amino acid sequence SEQ ID NO: 1 or an analog thereof and a $V_H$ domain having amino acid sequence SEQ ID NO: 2 or an analog thereof, wherein the $V_L$ and the $V_H$ domains of the anti-CD138 scFv are bound by a peptide linker and wherein the analog has at least 70% identity to the original sequence. According to one embodiment, the anti-CD138 scFv comprises a $V_L$ domain having amino acid sequence SEQ ID NO: 1 and a $V_H$ domain having amino acid sequence SEQ ID NO: 2. According to another embodiment, the $V_L$ domain is an analog of SEQ ID NO: 1. According to a further embodiment, the $V_H$ domain is an analog of SEQ ID NO: 2. According to some embodiments, the anti-CD138 scFv comprises a $V_L$ domain being an analog of SEQ ID NO: 1 and a $V_H$ domain being an analog of SEQ ID NO: 2.

According to one embodiment, the anti-CD138 scFv comprises $V_L$ and $V_H$ domains, wherein the $V_L$ domain comprises three complementarity determining regions (CDRs) of a $V_L$ having SEQ ID NO: 1 and the $V_H$ domain comprises three CDRs of a $V_H$ having SEQ ID NO: 2.

According to any one of the above embodiments, the anti-HER2 scFv comprises a $V_L$ domain having amino acid sequence SEQ ID NO: 3 or an analog thereof and a $V_H$ domain having amino acid sequence SEQ ID NO: 4 or an analog thereof, wherein the $V_L$ and the $V_H$ domains of the anti-HER2 scFv are bound by a peptide linker and wherein the analog has at least 70% identity to the original sequence. According to one embodiment, the anti-HER2 scFv comprises a $V_L$ domain having amino acid sequence SEQ ID NO: 3 and a $V_H$ domain having amino acid sequence SEQ ID NO: 4. According to another embodiment, the $V_L$ domain is an analog of SEQ ID NO: 3. According to another embodiment, the $V_H$ domain is an analog of SEQ ID NO: 4. According to some embodiments, the anti-HER2 scFv comprises a $V_L$ domain being an analog of SEQ ID NO: 3 and a $V_H$ domain being an analog of SEQ ID NO: 4.

According to one embodiment, the anti-HER2scFv comprises $V_L$ and $V_H$ domains, wherein the $V_L$ domain comprises three complementarity determining regions (CDRs) of a $V_L$ having SEQ ID NO: 3 and the $V_H$ domain comprises three CDRs of a $V_H$ having SEQ ID NO: 4.

The term "peptide linker" refers to any peptide capable of connecting two variable domains, and the length of the linker depends on the kinds of variable domains to be connected. According to some embodiments, the peptide linker is a peptide having amino acid sequence SEQ ID NO: 7. According to another embodiment, the peptide linker is an analog of a peptide having SEQ ID NO: 7. According to a further embodiment, the peptide linker has amino acid sequence SEQ ID NO: 36 or an analog thereof.

As described above, the scFv comprises a $V_H$ domain linked by a peptide linker to a $V_L$ domain. According to some embodiments, the $V_H$ is located N-terminally to $V_L$. According to another embodiment, the $V_L$ is located N-terminally to $V_H$.

According to some embodiments, the present invention provides T-cell genetically modified to express two CARs, wherein one CAR comprises an anti-CD138 scFv comprising a $V_L$ domain having SEQ ID NO: 1 and a $V_H$ domain having amino acid sequence SEQ ID NO: 2, and the second CAR comprises an anti-HER2 scFv comprising a $V_L$ domain having IN SEQ ID NO: 3 and a $V_H$ domain having amino acid sequence SEQ ID NO: 4.

The term "peptide" refers to a short chain of amino acid residues linked by peptide bonds, i.e., a covalent bond formed between the carboxyl group of one amino acid and an amino group of an adjacent amino acid. The term "peptide" refers to short sequences having up to 50 amino acids. A chain of amino acids monomers longer than 50 amino acid is referred as a "polypeptide". Such polypeptides, when having more than 50 amino acid residues, can also be classified as proteins, more particularly, proteins of low or medium molecular weight.

The terms "peptide analog", "analog", "sequence analog", "analogous sequence" and "analog of SEQ ID NO: X" are used herein interchangeably and refer to an analog of a peptide having at least 70% sequence identity to the original peptide, wherein the analog retains the activity of the original peptide; X represents a number of the sequence. Thus, the terms "analog" and "active analog" may be used interchangeably. The term "analog" refer to a peptide or a protein that contains substitutions, rearrangements, deletions, additions and/or chemical modifications in the amino acid sequence of the parent peptide or a protein, respectively. According to some embodiments, the peptide analog has at least 80%, at least 90% at least 95%, at least 98% or at least 99% sequence identity to the original peptide. According to one embodiment, the analog has about 80% to about 99%, about 85% to about 98% or about 90% to about 95% sequence identity to the original peptide. According to some embodiments, the analog of the present invention comprises the sequence of the original peptide in which 1, 2, 3, 4, or 5 substitutions were made.

The substitutions of the amino acids may be conservative or non-conservative substitution. The non-conservative substitution encompasses substitution of one amino acid by any other amino acid.

According to some embodiments, the term "analog" encompasses also the term "conservative analog".

Conservative substitutions of amino acids as known to those skilled in the art are within the scope of the present invention. Conservative amino acid substitutions include replacement of one amino acid with another having the same type of functional group or side chain, e.g., aliphatic, aromatic, positively charged, negatively charged. One of skill will recognize that individual substitutions, is a "conservatively modified analog" where the alteration results in the substitution of an amino acid with a chemically similar amino acid. Conservative substitution tables providing functionally similar amino acids are well known in the art. One typical example of conservative substitution is provided below.

The following six groups each contain amino acids that are conservative substitutions for one another: (1) Alanine (A), Serine (S), Threonine (T); (2) Aspartic acid (D), Glutamic acid (E); (3) Asparagine (N), Glutamine (Q); (4) Arginine (R), Lysine (K); (5) Isoleucine (I), Leucine (L), Methionine (M), Valine (V); and (6) Phenylalanine (F), Tyrosine (Y), Tryptophan (W). In other embodiments, the conservative substitution encompass substitution with a chemically similar non-natural amino acid.

Thus, in some embodiments, the analog is a conservative analog of the scFv, either anti-HER2 or anti-CD138. According to some embodiments, the conservative analog of the present invention comprises the sequence of the original scFv in which 1, 2, 3, 4, or 5 conservative substitutions were made. According to another embodiment, the analog consists of the amino acid sequence of the original peptide in which 1, 2 or 3 conservative substitution were made. Thus, the analog consists of the amino acid sequence of the original peptide with 1, 2 or 3 conservative substitutions.

According to some embodiments, the anti-CD138 scFv has amino acid sequence SEQ ID NO: 28. According to other embodiments, the anti-CD138 scFv consists of amino acid sequence SEQ ID NO: 28.

According to other embodiments, the anti-HER2 scFv has an amino acid sequence SEQ ID NO: 29. According to other embodiments, the anti-HER2 scFv consists of amino acid sequence SEQ ID NO: 29.

According to further embodiments, the anti-CD138 scFv has an amino acid sequence SEQ ID NO: 28 and the anti-HER2 scFv has an amino acid sequence SEQ ID NO: 29. According to another embodiment, the anti-CD138 scFv consists of the amino acid sequence SEQ ID NO: 28 and the anti-HER2 scFv consists of the amino acid sequence SEQ ID NO: 29.

According to any one of the above embodiments, the extracellular domain of the CARs comprises a leader peptide. According to one embodiment, the leader peptide is located N-terminally to scFv. The term "leader peptide", "lead peptide" and "signal peptide" are used herein interchangeable and refer to a peptide that translocates or prompts translocation of the target protein to cellular membrane. According to one embodiment, the leader peptide is located N-terminally to scFv.

According to one embodiment, the first CAR comprises a leader peptide comprising SEQ ID NO: 30 located N-terminally to anti-CD138 scFv. According to another embodiment, the leader peptide comprising SEQ ID NO: 30 is located N-terminally to anti-CD138 scFv comprising or consisting of SEQ ID NO: 28.

According to one embodiment, the second CAR comprises a leader peptide comprising SEQ ID NO: 30 located N-terminally to anti-HER2 scFv. According to another embodiment, the leader peptide comprising SEQ ID NO: 30 is located N-terminally to anti-HER2 scFv comprising or consisting of SEQ ID NO: 29.

According to any one of the above embodiments, at least one of the CARs comprises a costimulatory domain and at least one other CAR comprises an activation domain.

According to some embodiments, the first CAR comprises a costimulatory domain and the second CAR comprises an activation domain.

According to some embodiments, the costimulatory domain is selected from a costimulatory domain of CD28, 4-1BB, OX40, iCOS, CD27, CD80 and CD70. According to one embodiment, the costimulatory domain is a costimulatory domain of CD28. According to another embodiment, the costimulatory domain has an amino acid sequence SEQ ID NO: 9. According to a further embodiment, the costimulatory domain is an analog of SEQ ID NO: 9.

According to some embodiments, the activation domain is selected from FcRγ and CD3-ζ. According to one embodiment, the activation domain has the amino acid sequence SEQ ID NO: 8. According to a further embodiment, the activation domain is an analog of SEQ ID NO: 8

According to the teaching of the present invention, it is beneficial to separate between a costimulatory domain and an activation domain, thus, according to one embodiment, one CAR comprises only a costimulatory domain and the other CAR comprises only an activation domain. Thus, in one embodiment, the first CAR, comprising anti-CD138 scFv, comprises a costimulatory domain and devoid of an activation domain, and the second CAR comprising anti-HER2 scFv comprises an activation domain and devoid of a costimulatory domain. According to another embodiment, the first CAR comprises an activation domain and devoid of a costimulatory domain and the second CAR comprises a costimulatory domain and devoid of an activation domain.

According to a further embodiment, at least one of the CARs comprises both an activation domain and a costimulatory domain.

According to another embodiment, the second CAR comprises both an activation domain and a costimulatory domain. According to such embodiments, the first CAR comprises a costimulatory domain and devoid of an activation domain.

According to some embodiments, the activation domain has amino acid sequence SEQ ID NO: 8 and the costimulatory domain has the amino acid sequence SEQ ID NO: 9. According to one embodiment, the activation domain is an analog of the activation domain having SEQ ID NO: 8. According to a further embodiment, the costimulatory domain in an analog of the costimulatory domain having SEQ ID NO: 9.

According to one embodiment, the first CAR comprises amino acid sequences SEQ ID NO: 28 and SEQ ID NO: 9. According to another embodiment, the second CAR comprises amino acid sequences SEQ ID NO: 29 and SEQ ID NO: 8. According to one embodiment, the present invention provides an T-cell engineered to express two CARs, wherein the first CAR comprises amino acid sequences SEQ ID NO: 28 and SEQ ID NO: 9 and the second CAR comprises amino acid sequences SEQ ID NO: 29 and SEQ ID NO: 8.

According to any one of the above embodiments, the CARs comprise a transmembrane domain (TM) and hinge domain. According to the teaching of the present invention when reference made to a TM domain it includes also a hinge domain and sequences of the transmembrane domain include also the sequences of the hinge domains. According to one embodiment, the first CAR comprises a TM domain I (TM-I) having amino acid sequence SEQ ID NO: 31. According to another embodiment, the second CAR comprises a TM domain II (TM-II) having amino acid sequence SEQ ID NO: 32.

According to some embodiments, the present invention provides a T-cell genetically modified to express two different CARs, wherein the first CAR comprises anti-CD138 scFv and the second CAR comprises anti-HER2 scFv wherein the CAR comprising anti-CD138 scFv has the amino acid sequence SEQ ID NO: 10. According to other embodiments, the present invention provides a T-cell genetically modified to express two different CARs, wherein the first CAR comprises anti-CD138 scFv and the second CAR comprises anti-HER2 scFv wherein the CAR comprising anti-HER2 scFv has the amino acid sequence SEQ ID NO:

11. According to some embodiments, the present invention provides a T-cell genetically modified to express two different CARs, wherein the first CAR comprises SEQ ID NO: 10 and the second CAR comprises SEQ ID NO: 11. According to one embodiment, the first CAR has an amino acid sequence being an analog of SEQ ID NO: 10. According to another embodiment, the second CAR has an amino acid sequence being an analog of SEQ ID NO: 11. According to a further embodiment, the first CAR has the amino acid sequence analogous to SEQ ID NO: 10 and the second CAR has the amino acid sequence analogous to SEQ ID NO: 11. According to one embodiment, the present invention provides an engineered T-cell comprising two chimeric antigen receptors (CARs), wherein the first CAR consists of amino acid sequence SEQ ID NO: 10 and the second CAR consists of amino acid sequence SEQ ID NO: 11.

According to any one of the above embodiments, the T cell is selected are from CD4+ T-cell and a CD8+ T-cell. Thus, in one embodiment, the present invention provides CD4+ T-cells genetically modified to express two distinct separate CARs, wherein the first CAR comprises anti-CD138 scFv and the second CAR comprises anti-HER2 scFv. According to another embodiment, the present invention provides CD8+ T-cells genetically modified to express two distinct separate CARs, wherein the first CAR comprises anti-CD138 scFv and the second CAR comprises anti-HER2 scFv. According to some such embodiments, the first CAR comprises amino acid sequences SEQ ID NO: 28 and SEQ ID NO: 9. According to another embodiment, the second CAR comprises amino acid sequences SEQ ID NO: 29 and SEQ ID NO: 8. According to one embodiment, the first CAR comprises amino acid sequences SEQ ID NO: 28 and SEQ ID NO: 9 and the second CAR comprises amino acid sequences SEQ ID NO: 29 and SEQ ID NO: 8. According to one such embodiments, the first CAR has the amino acid sequence SEQ ID NO: 10 or being an analog thereof and the second CAR has the amino acid sequence SEQ ID NO: 11 or being an analog thereof. According to a further embodiment, the present invention provides CD4+ and/or CD8+ T-cells genetically modified to express two distinct separate CARs, wherein the first CAR consists of amino acid sequence SEQ ID NO: 10 and the second CAR consists of amino acid sequence SEQ ID NO: 11.

According to some embodiments, the present invention provides a T-cell genetically modified to express at least two distinct separate chimeric antigen receptors (CARs), wherein the first CAR comprises an scFv antigen binding domain that binds specifically to human CD138 (anti-CD138 scFv) and the second CAR comprises an scFv antigen binding domain that binds specifically to human CD24 (anti-CD24 scFv).

According to one embodiment, the present invention provides a T-cell genetically modified to express two distinct separate chimeric antigen receptors (CARs), wherein the first CAR comprises anti-CD138 scFv and the second CAR comprises anti-CD24 scFv.

According to any one of the above embodiments, anti-CD138 and anti-CD24 scFv binding domains comprise $V_L$ and $V_H$ domains.

According to some embodiments, the present invention provides a T-cell genetically modified to express two different CARs, wherein the first CAR comprises anti-CD138 scFv and the second CAR comprises anti-CD24 scFv, and the anti-CD138 scFv comprises a $V_L$ domain having amino acid sequence SEQ ID NO: 1 or an analog thereof and a $V_H$ domain having amino acid sequence SEQ ID NO: 2 or an analog thereof, wherein the $V_L$ and the $V_H$ domains of the anti-CD138 scFv are bound by a peptide linker and wherein the analog has at least 70% identity to the original sequence. According to one embodiment, the anti-CD138 scFv comprises a $V_L$ domain having amino acid sequence SEQ ID NO: 1 and a $V_H$ domain having amino acid sequence SEQ ID NO: 2. According to another embodiment, the $V_L$ domain is an analog of SEQ ID NO: 1. According to a further embodiment, the $V_H$ domain is an analog of SEQ ID NO: 2. According to some embodiments, the anti-CD138 scFv comprises a $V_L$ domain being an analog of SEQ ID NO: 1 and a $V_H$ domain being an analog of SEQ ID NO: 2. According to one embodiment, the anti-CD138 scFv comprises $V_L$ and $V_H$ domains, wherein the $V_L$ domain comprises three complementarity determining regions (CDRs) of a $V_L$ having SEQ ID NO: 1 and the $V_H$ domain comprises three CDRs of a $V_H$ having SEQ ID NO: 2.

According to such embodiments, the anti-CD24 scFv comprises a $V_L$ domain having amino acid sequence SEQ ID NO: 5 or an analog thereof and a $V_H$ domain having amino acid sequence SEQ ID NO: 6 or an analog thereof, wherein the $V_L$ and the $V_H$ domains of the anti-CD24 scFv are bound by a peptide linker and wherein the analog has at least 70% identity to the original sequence. According to one embodiment, the anti-CD24 scFv comprises a $V_L$ domain having amino acid sequence SEQ ID NO: 5 and a $V_H$ domain having amino acid sequence SEQ ID NO: 6. According to another embodiment, the $V_L$ domain is an analog of SEQ ID NO: 5. According to another embodiment, the $V_H$ domain is an analog of SEQ ID NO: 5. According to some embodiments, the anti-CD24 scFv comprises a $V_L$ domain being an analog of IN SEQ ID NO: 5 and a $V_H$ domain being an analog of SEQ ID NO: 6. According to one embodiment, the anti-CD24 scFv comprises $V_L$ and $V_H$ domains, wherein the $V_L$ domain comprises three complementarity determining regions (CDRs) of a $V_L$ having SEQ ID NO: 5 and the $V_H$ domain comprises three CDRs of a $V_H$ having SEQ ID NO: 6.

According to some embodiments, the peptide linker is a peptide having amino acid sequence SEQ ID NO: 36. According to another embodiment, the peptide linker is an analog of a peptide having SEQ ID NO: 36. As described above, the scFv comprises a $V_H$ domain linked by a peptide linker to a $V_L$ domain. According to some embodiments, the $V_H$ is located N-terminally to $V_L$. According to another embodiment, the $V_L$ is located N-terminally to $V_H$. According to a further embodiment, the peptide linker is a peptide having amino acid sequence SEQ ID NO: 7.

According to some embodiments, the present invention provides T-cell genetically modified to express two CARs, wherein one CAR comprises an anti-CD138 scFv comprising a $V_L$ domain having SEQ ID NO: 1 and a $V_H$ domain having amino acid sequence SEQ ID NO: 2, and the second CAR comprises an anti-CD24 scFv comprising a $V_L$ domain having SEQ ID NO: 5 and a $V_H$ domain having amino acid sequence SEQ ID NO: 6.

According to some embodiments, the peptide analog has at least 80%, at least 90% at least 95%, at least 98% or at least 99% sequence identity to the original peptide. According to one embodiment, the analog has about 80% to about 99%, about 85% to about 98% or about 90% to about 95% sequence identity to the original peptide. According to some embodiments, the analog of the present invention comprises the sequence of the original peptide in which 1, 2, 3, 4, or 5 substitutions were made.

In some embodiments, the analog is a conservative analog of the scFv, either anti-CD24 or anti-CD138. According to some embodiments, the conservative analog of the present invention comprises the sequence of the original scFv in which 1, 2, 3, 4, or 5 conservative substitutions were made. According to another embodiment, the analog consists of the amino acid sequence of the original peptide in which 1, 2 or 3 conservative substitution were made. Thus, the analog consists of the amino acid sequence of the original peptide with 1, 2 or 3 conservative substitutions.

According to some embodiments, the present invention provides a T-cell genetically modified to express two different CARs, wherein the first CAR comprises anti-CD138 scFv and the second CAR comprises anti-CD24 scFv, and the anti-CD138 scFv has an amino acid sequence SEQ ID NO: 28. According to other embodiments, the anti CD138 scFv consists of amino acid sequence SEQ ID NO: 28. According to other embodiments, the anti-CD24 scFv has an amino acid sequence SEQ ID NO: 33. According to other embodiments, the anti-CD24 scFv consists of amino acid sequence SEQ ID NO: 33.

According to further embodiments, the anti-CD138 scFv has an amino acid sequence SEQ ID NO: 28 and the anti-CD24 scFv has an amino acid sequence SEQ ID NO: 30. According to another embodiment, the anti-CD138 scFv consists of the amino acid sequence SEQ ID NO: 28 and the anti-CD24 scFv consists of the amino acid sequence SEQ ID NO: 30.

According to one embodiment, the first CAR comprises a leader peptide comprising SEQ ID NO: 30 located N-terminally to anti-CD138 scFv. According to another embodiment, the leader peptide comprising SEQ ID NO: 30 is located N-terminally to anti-CD138 scFv comprising or consisting of SEQ ID NO: 28. According to one embodiment, the second CAR comprises a leader peptide comprising SEQ ID NO: 30 located N-terminally to anti-CD24 scFv. According to another embodiment, the leader peptide comprising SEQ ID NO: 30 is located N-terminally to anti-CD24 scFv comprising or consisting of SEQ ID NO: 33.

According to any one of the above embodiments, at least one of the CARs comprises a costimulatory domain and at least one other CAR comprises an activation domain. According to some embodiments the CAR comprises a costimulatory domain and the second CAR comprises an activation domain. According to some embodiments, the costimulatory domain is selected from a costimulatory domain of CD28, 4-1BB, OX40, iCOS, CD27, CD80 and CD70. According to one embodiment, the costimulatory domain is a costimulatory domain of CD28. According to another embodiment, the costimulatory domain has an amino acid sequence SEQ ID NO: 9. According to a further embodiment, the costimulatory domain is an analog of SEQ ID NO: 9. According to some embodiments, the activation domain is selected from FcRγ and CD3-ζ. According to one embodiment, the activation domain has the amino acid sequence SEQ ID NO: 8. According to a further embodiment, the activation domain is an analog of SEQ ID NO: 8

In one embodiment, the first CAR, comprising anti-CD138 scFv, comprises a costimulatory domain and devoid of an activation domain, and the second CAR comprising anti-CD24 scFv comprises an activation domain and devoid of a costimulatory domain. According to another embodiment, the first CAR comprising anti-CD138 scFv comprises an activation domain and devoid of a costimulatory domain and the second CAR comprising anti-CD24 scFv comprises a costimulatory domain and devoid of an activation domain.

According to a further embodiment, at least one of such CARs comprises both an activation domain and a costimulatory domain.

According to another embodiment, the second CAR comprises both an activation domain and a costimulatory domain. According to such embodiments, the first CAR comprises a costimulatory domain and devoid of an activation domain.

In one embodiment, the first CAR, comprising anti-CD138 scFv, the second CAR comprising anti-CD24 scFv, the activation domain has the amino acid sequence SEQ ID NO: 8 and the costimulatory domain has the amino acid sequence SEQ ID NO: 9. According to another embodiment, the activation domain is an analog of the activation domain having SEQ ID NO: 8. According to a further embodiment, the costimulatory domain in an analog of the costimulatory domain having SEQ ID NO: 9.

According to one embodiment, the first CAR comprises amino acid sequences SEQ ID NO: 28 and SEQ ID NO: 9 and the second CAR comprises anti-CD24 scFv. According to another embodiment, the second CAR comprises amino acid sequences SEQ ID NO: 33 and SEQ ID NO: 8. According to one embodiment, the present invention provides an engineered T-cell comprising two CARs, wherein the first CAR comprises amino acid sequences SEQ ID NO: 28 and SEQ ID NO: 9 and the second CAR comprises amino acid sequences SEQ ID NO: 33 and SEQ ID NO: 8.

According to some embodiments, the present invention provides a T-cell genetically modified to express two different CARs, wherein the first CAR comprises anti-CD138 scFv and the second CAR comprises anti-CD24 scFv and the first CAR comprising anti-CD138 scFv, comprises a TM domain I (TM-I) having amino acid sequence SEQ ID NO: 31. According to another embodiment, the second CAR, comprising anti-CD24 scFv, comprises a TM domain II (TM-II) having amino acid sequence SEQ ID NO: 32.

According to some embodiments, the present invention provides a T-cell genetically modified to express two different CARs, wherein the first CAR comprises anti-CD138 scFv and the second CAR comprises anti-CD24 scFv wherein the CAR comprising anti-CD138 scFv has the amino acid sequence SEQ ID NO: 10. According to another embodiment, the present invention provides a T-cell genetically modified to express two different CARs, wherein the first CAR comprises anti-CD138 scFv and the second CAR comprises anti-CD24 scFv wherein the CAR comprising anti-CD24 scFv has the amino acid sequence SEQ ID NO: 12. According to some embodiments, the present invention provides a T-cell genetically modified to express two different CARs, wherein the first CAR comprises SEQ ID NO: 10 and the second CAR comprises SEQ ID NO: 12. According to one embodiment, the first CAR has an amino acid sequence being an analog of SEQ ID NO: 10. According to another embodiment, the second CAR has an amino acid sequence being an analog of SEQ ID NO: 12. According to a further embodiment, the first CAR has the amino acid sequence analogous to SEQ ID NO: 10 and the second CAR has the amino acid sequence analogous to SEQ ID NO: 12. According to one embodiment, the present invention provides an engineered T-cell comprising two chimeric antigen receptors (CARs), wherein the first CAR consists of amino acid sequence SEQ ID NO: 10 and the second CAR consists of amino acid sequence SEQ ID NO: 12.

According to any one of the above embodiments, the T cell is selected are from CD4+ T-cell and a CD8+ T-cell. Thus, in one embodiment, the present invention provides CD4+ T-cells genetically modified to express two distinct separate CARs, wherein the first CAR comprises anti-CD138 scFv and the second CAR comprises anti-CD24 scFv. According to another embodiment, the present invention provides CD8+ T-cells genetically modified to express two distinct separate CARs, wherein the first CAR comprises anti-CD138 scFv and the second CAR comprises anti-CD24 scFv. According to some such embodiments, the first CAR comprises amino acid sequences SEQ ID NO: 28 and SEQ ID NO: 9. According to another embodiment, the second CAR comprises amino acid sequences SEQ ID NO: 33 and SEQ ID NO: 8. According to one embodiment, the first CAR comprises amino acid sequences SEQ ID NO: 28 and SEQ ID NO: 9 and the second CAR comprises amino acid sequences SEQ ID NO: 33 and SEQ ID NO: 8. According to one such embodiments, the first CAR has the amino acid sequence SEQ ID NO: 10 or being an analog thereof and the second CAR has the amino acid sequence SEQ ID NO: 12 or being an analog thereof. According to a further embodiment, the present invention provides CD4+ and/or CD8+ T-cells genetically modified to express two distinct separate CARs, wherein the first CAR consists of amino acid sequence SEQ ID NO: 10 and the second CAR consists of amino acid sequence SEQ ID NO: 12.

According to some embodiments, the present invention provides a T-cell genetically modified to express at least two distinct separate chimeric antigen receptors (CARs), wherein the first CAR comprises an scFv antigen binding domain that binds specifically to human HER2 (anti-HER2 scFv) and the second CAR comprises an scFv antigen binding domain that binds specifically to human CD24 (anti-CD24 scFv).

According to one embodiment, the present invention provides a T-cell genetically modified to express two distinct separate chimeric antigen receptors (CARs), wherein the first CAR comprises anti-HER2 scFv and the second CAR comprises anti-CD24 scFv.

According to any one of the above embodiments, anti-HER2 and anti-CD24 scFv binding domains comprise $V_L$ and $V_H$ domains.

According to some embodiments, the present invention provides a T-cell genetically modified to express two different CARs, wherein the first CAR comprises anti-HER2 scFv and the second CAR comprises anti-CD24 scFv, and the anti-HER2 scFv comprises a $V_L$ domain having amino acid sequence SEQ ID NO: 3 or an analog thereof and a $V_H$ domain having amino acid sequence SEQ ID NO: 4 or an analog thereof, wherein the $V_L$ and the $V_H$ domains of the anti-HER2 scFv are bound by a peptide linker and wherein the analog has at least 70% identity to the original sequence. According to one embodiment, the anti-HER2 scFv comprises a $V_L$ domain having amino acid sequence SEQ ID NO: 3 and a $V_H$ domain having amino acid sequence SEQ ID NO: 4. According to another embodiment, the $V_L$ domain is an analog of SEQ ID NO: 3. According to a further embodiment, the $V_H$ domain is an analog of SEQ ID NO: 4. According to some embodiments, the anti-HER2 scFv comprises a $V_L$ domain being an analog of SEQ ID NO: 3 and a $V_H$ domain being an analog of SEQ ID NO: 4. According to one embodiment, the anti-HER2 scFv comprises $V_L$ and $V_H$ domains, wherein the $V_L$ domain comprises three complementarity determining regions (CDRs) of a $V_L$ having SEQ ID NO: 3 and the $V_H$ domain comprises three CDRs of a $V_H$ having SEQ ID NO: 4.

According to such embodiments, the anti-CD24 scFv comprises a $V_L$ domain having amino acid sequence SEQ ID NO: 5 or an analog thereof and a $V_H$ domain having amino acid sequence SEQ ID NO: 6 or an analog thereof, wherein the $V_L$ and the $V_H$ domains of the anti-CD24 scFv are bound by a peptide linker and wherein the analog has at least 70% identity to the original sequence. According to one embodiment, the anti-CD24 scFv comprises a $V_L$ domain having amino acid sequence SEQ ID NO: 5 and a $V_H$ domain having amino acid sequence SEQ ID NO: 6. According to another embodiment, the $V_L$ domain is an analog of SEQ ID NO: 5. According to another embodiment, the $V_H$ domain is an analog of SEQ ID NO: 5. According to some embodiments, the anti-CD24 scFv comprises a $V_L$ domain being an analog of IN SEQ ID NO: 5 and a $V_H$ domain being an analog of SEQ ID NO: 6. According to one embodiment, the anti-CD24 scFv comprises $V_L$ and $V_H$ domains, wherein the $V_L$ domain comprises three complementarity determining regions (CDRs) of a $V_L$ having SEQ ID NO: 5 and the $V_H$ domain comprises three CDRs of a $V_H$ having SEQ ID NO: 6.

According to some embodiments, the peptide linker is a peptide having amino acid sequence SEQ ID NO: 7. According to another embodiment, the peptide linker is an analog of a peptide having SEQ ID NO: 7. As described above, the scFv comprises a $V_H$ domain linked by a peptide linker to a $V_L$ domain. According to some embodiments, the $V_H$ is located N-terminally to $V_L$. According to another embodiment, the $V_L$ is located N-terminally to $V_H$.

According to some embodiments, the present invention provides T-cell genetically modified to express two CARs, wherein one CAR comprises an anti-HER2 scFv comprising a $V_L$ domain having SEQ ID NO: 3 and a $V_H$ domain having amino acid sequence SEQ ID NO: 4, and the second CAR comprises an anti-CD24 scFv comprising a $V_L$ domain having SEQ ID NO: 5 and a $V_H$ domain having amino acid sequence SEQ ID NO: 6.

According to some embodiments, the peptide analog has at least 80%, at least 90% at least 95%, at least 98% or at least 99% sequence identity to the original peptide. According to one embodiment, the analog has about 80% to about 99%, about 85% to about 98% or about 90% to about 95% sequence identity to the original peptide. According to some embodiments, the analog of the present invention comprises the sequence of the original peptide in which 1, 2, 3, 4, or 5 substitutions were made. Thus, in some embodiments, the analog is a conservative analog of the scFv, either anti-CD24 or anti-HER2. According to some embodiments, the conservative analog of the present invention comprises the sequence of the original scFv in which 1, 2, 3, 4, or 5 conservative substitutions were made. According to another embodiment, the analog consists of the amino acid sequence of the original peptide in which 1, 2 or 3 conservative substitution were made. Thus, the analog consists of the amino acid sequence of the original peptide with 1, 2 or 3 conservative substitutions.

According to some embodiments, the present invention provides a T-cell genetically modified to express two different CARs, wherein the first CAR comprises anti-HER scFv, the second CAR comprises anti-CD24 scFv, and the anti-HER2 scFv has an amino acid sequence SEQ ID NO: 29. According to other embodiments, the anti HER2 scFv consists of amino acid sequence SEQ ID NO: 29. According to other embodiments, the anti-CD24 scFv has an amino acid sequence SEQ ID NO: 33. According to other embodiments, the anti-CD24 scFv consists of amino acid sequence SEQ ID NO: 33.

According to further embodiments, the anti-HER2 scFv has an amino acid sequence SEQ ID NO: 29 and the anti-CD24 scFv has an amino acid sequence SEQ ID NO: 33. According to another embodiment, the anti-HER2 scFv consists of the amino acid sequence SEQ ID NO: 29 and the anti-CD24 scFv consists of the amino acid sequence SEQ ID NO: 33.

According to any one of the above embodiments, the extracellular domain of the CARs comprises a leader peptide. According to one embodiment, the leader peptide is located N-terminally to scFv.

According to one embodiment, the first CAR comprises a leader peptide comprising SEQ ID NO: 30 located N-terminally to anti-HER2 scFv. According to another embodiment, the leader peptide comprising SEQ ID NO: 30 is located N-terminally to anti-HER2 scFv comprising or consisting of SEQ ID NO: 29. According to one embodiment, the second CAR comprises a leader peptide comprising SEQ ID NO: 30 located N-terminally to anti-CD24 scFv. According to another embodiment, the leader peptide comprising SEQ ID NO: 30 is located N-terminally to anti-CD24 scFv comprising or consisting of SEQ ID NO: 33.

According to any one of the above embodiments, at least one of the CARs comprises a costimulatory domain and at least one other CAR comprises an activation domain. According to some embodiments, the CAR comprises a costimulatory domain and the second CAR comprises an activation domain. According to some embodiments, the costimulatory domain is selected from a costimulatory domain of CD28, 4-1BB, OX40, iCOS, CD27, CD80 and CD70. According to one embodiment, the costimulatory domain is a costimulatory domain of CD28. According to another embodiment, the costimulatory domain has an amino acid sequence SEQ ID NO: 9. According to a further embodiment, the costimulatory domain is an analog of SEQ ID NO: 9. According to some embodiments, the activation domain is selected from FcRγ and CD3-ζ. According to one embodiment, the activation domain has the amino acid sequence SEQ ID NO: 8. According to a further embodiment, the activation domain is an analog of SEQ ID NO: 8

In such embodiments, the first CAR, comprising anti-HER2 scFv, comprises a costimulatory domain and devoid of an activation domain, and the second CAR comprising anti-CD24 scFv comprises an activation domain and devoid of a costimulatory domain. According to another embodiment, the first CAR comprising anti-HER2 scFv comprises an activation domain and devoid of a costimulatory domain and the second CAR comprising anti-CD24 scFv comprises a costimulatory domain and devoid of an activation domain.

According to a further embodiment, at least one of such CARs comprises both an activation domain and a costimulatory domain.

According to another embodiment, the second CAR comprises both an activation domain and a costimulatory domain. According to such embodiments, the first CAR comprises a costimulatory domain and devoid of an activation domain.

In one embodiment, the first CAR, comprising anti-HER2 scFv, the second CAR comprising anti-CD24 scFv, the activation domain has the amino acid sequence SEQ ID NO: 8 and the costimulatory domain has the amino acid sequence SEQ ID NO: 9. According to another embodiment, the activation domain is an analog of the activation domain having SEQ ID NO: 8. According to a further embodiment, the costimulatory domain in an analog of the costimulatory domain having SEQ ID NO: 9.

According to one embodiment, the first CAR comprises amino acid sequences SEQ ID NO: 29 and SEQ ID NO: 9 and the second CAR comprises anti-CD24 scFv. According to another embodiment, the second CAR comprises amino acid sequences SEQ ID NO: 33 and SEQ ID NO: 8. According to one embodiment, the present invention provides an engineered T-cell comprising two CARs, wherein the first CAR comprises amino acid sequences SEQ ID NO: 29 and SEQ ID NO: 9 and the second CAR comprises amino acid sequences SEQ ID NO: 33 and SEQ ID NO: 8.

According to one embodiment, the first CAR comprising anti-HER2 scFv, comprises a TM domain I (TM-I) having amino acid sequence SEQ ID NO: 31. According to another embodiment, the second CAR, comprising anti-CD24 scFv, comprises a TM domain II (TM-II) having amino acid sequence SEQ ID NO: 32.

According to some embodiments, the present invention provides a T-cell genetically modified to express two different CARs, wherein the first CAR comprises anti-HER2 scFv and the second CAR comprises anti-CD24 scFv wherein the CAR comprising anti-HER2 scFv has the amino acid sequence SEQ ID NO: 13. According to another embodiment, the present invention provides a T-cell genetically modified to express two different CARs, wherein the first CAR comprises anti-HER2 scFv and the second CAR comprises anti-CD24 scFv wherein the CAR comprising anti-CD24 scFv has the amino acid sequence SEQ ID NO: 12. According to some embodiments, the present invention provides an engineered T-cell comprising two chimeric antigen receptors (CARs), wherein the first CAR has amino acid sequence SEQ ID NO: 13 and the second CAR has amino acid sequence SEQ ID NO: 12. According to one embodiment, the first CAR has an amino acid sequence being an analog of SEQ ID NO: 13. According to another embodiment, the second CAR has amino acid sequence being an analog of SEQ ID NO: 12. According to a further embodiment, the first CAR has the amino acid sequence analogous to SEQ ID NO: 13 and the second CAR has the amino acid sequence analogous to SEQ ID NO: 12. According to one embodiment, the present invention provides an engineered T-cell comprising two chimeric antigen receptors (CARs), wherein the first CAR consists of amino acid sequence SEQ ID NO: 13 and the second CAR consists of amino acid sequence SEQ ID NO: 11.

According to any one of the above embodiments, the T cell is selected are from CD4+ T-cell and a CD8+ T-cell. Thus, in one embodiment, the present invention provides CD4+ T-cells genetically modified to express two distinct separate CARs, wherein the first CAR comprises anti-HER2 scFv and the second CAR comprises anti-CD24 scFv. According to another embodiment, the present invention provides CD8+ T-cells genetically modified to express two distinct separate CARs, wherein the first CAR comprises anti-HER2 scFv and the second CAR comprises anti-CD24 scFv. According to some such embodiments, the first CAR comprises amino acid sequences SEQ ID NO: 29 and SEQ ID NO: 9. According to another embodiment, the second CAR comprises amino acid sequences SEQ ID NO: 33 and SEQ ID NO: 8. According to one embodiment, the first CAR comprises amino acid sequences SEQ ID NO: 29 and SEQ ID NO: 9 and the second CAR comprises amino acid sequences SEQ ID NO: 33 and SEQ ID NO: 8. According to one such embodiments, the first CAR has the amino acid sequence SEQ ID NO: 13 or being an analog thereof and the second CAR has the amino acid sequence SEQ ID NO: 12 or being an analog thereof. According to a further embodiment, the present invention provides CD4+ and/or CD8+ T-cells genetically modified to express two distinct separate CARs, wherein the first CAR consists of amino acid sequence SEQ ID NO: 13 and the second CAR consists of amino acid sequence SEQ ID NO: 12.

According to any one of the above embodiments, the T-cell of the present invention are capable of expressing the two CARs. According to other embodiments, the T-cell of the present invention express the two CARs.

According to another aspect, the present invention provides a T-cell comprising at least one copy of one or more DNA constructs encoding the at least two CARs of the present invention. Thus in one embodiment, the present invention provides a T-cell comprising at least one copy of one or more DNA constructs encoding at least two distinct and separate chimeric antigen receptors (CARs), wherein the antigen binding domain of one CAR is different from the antigen binding domain of another CAR and wherein the antigen binding domain is selected from anti-CD138, anti-HER2 and anti-CD24 antigen binding domain.

According to some embodiments, one or more DNA constructs encode two CAR of the present invention, wherein the first CAR comprises an antigen binding domain that binds specifically to CD138 and the second CAR comprises an antigen binding domain that binds specifically to HER2. According to another embodiment, the first CAR comprises anti-CD138 scFv and the second CAR comprises anti-HER2 scFv.

According to certain embodiments, one or more DNA constructs encode two CAR of the present invention, wherein the first CAR comprises an antigen binding domain that binds specifically to CD138 and the second CAR comprises an antigen binding domain that binds specifically to CD24. According to another embodiment, the first CAR comprises anti-CD138 scFv and the second CAR comprises anti-CD24 scFv.

According to other embodiments, one or more DNA constructs encode two CAR of the present invention, wherein the first CAR comprises an antigen binding domain that binds specifically to HER2 and the second CAR comprises an antigen binding domain that binds specifically to CD24. According to another embodiment, the first CAR comprises anti-HER2 scFv and the second CAR comprises anti-CD24 scFv.

According to any one of the above embodiments, the T-cell expresses or capable of expressing the CARs of the present invention.

The term "DNA construct" as used herein refers to an artificially constructed segment of a nucleic acid. It can be an isolate or integrated in to another DNA molecule. Accordingly, a "recombinant DNA construct" is produced by laboratory methods. The term "nucleic acid" encompasses DNA, RNA, single stranded or double stranded and chemical modifications thereof. The terms "nucleic acid" and "polynucleotide" are used interchangeably herein.

The CARs of the present invention may be encoded by one DNA construct or 2 or more DNA constructs.

According to one embodiment, the two CARs of the present invention are encoded by one DNA construct.

In one embodiment, the present invention provides a T-cell comprising at least one copy of a DNA construct encoding for: (A) from 5' to 3': (i) a leader peptide, (ii) anti-CD138 scFv, (iii) a transmembrane domain I, (iv) a costimulatory domain, an activation domain or both; and (B) from 5' to 3': (v) a leader peptide, (vi) anti-HER2 scFv, (vii) a transmembrane domain II, and (viii) a costimulatory domain, an activation domain or both; wherein (A) and (B) are separated by a self-cleaving peptide. According to one embodiment, the DNA construct encodes, from 5' to 3', (i) a leader peptide, (ii) anti-CD138 scFv, (iii) a transmembrane domain I, (iv) a costimulatory domain, (v) a self-cleaving peptide, (vi) a leader peptide, (vii) anti-HER2 scFv, (viii) a transmembrane domain II, and (ix) an activation domain. According to another embodiment, the DNA construct encodes, from 5' to 3', (i) a leader peptide, (ii) anti-HER2 scFv, (iii) a transmembrane domain II, (iv) an activation domain, (v) a self-cleaving peptide, (vi) a leader peptide, (vii) anti-CD138 scFv, (viii) a transmembrane domain I, and (ix) a costimulatory domain.

In one embodiment, the present invention provides a T-cell comprising at least one copy of a DNA construct encoding for: (A) from 5' to 3': (i) a leader peptide, (ii) anti-CD138 scFv, (iii) a transmembrane domain I, and (iv) a costimulatory domain, an activation domain or both; and (B) from 5' to 3': (v) a leader peptide, (vi) anti-CD24 scFv, (vii) a transmembrane domain II and (viii) a costimulatory domain, an activation domain or both, wherein (A) and (B) are separated by a self-cleaving peptide.

According to one embodiment, the DNA construct encodes, from 5' to 3', (i) a leader peptide, (ii) anti-CD138 scFv, (iii) a transmembrane domain I, (iv) a costimulatory domain, (v) a self-cleaving peptide, (vi) a leader peptide, (vii) anti-CD24 scFv, (viii) a transmembrane domain II and (ix) an activation domain. According to another embodiment, the DNA construct encodes, from 5' to 3', (i) a leader peptide, (ii) anti-CD24 scFv, (iii) a transmembrane domain II, (iv) an activation domain, (v) a self-cleaving peptide, (vi) a leader peptide, (vii) anti-CD138 scFv, (viii) a transmembrane domain I, and (ix) a costimulatory domain.

In one embodiment, the present invention provides a T-cell comprising at least one copy of a DNA construct encoding for: (A) from 5' to 3': (i) a leader peptide, (ii) anti-HER2 scFv, (iii) a transmembrane domain I, and (iv) a costimulatory domain, an activation domain or both; and (B) from 5' to 3': (v) a leader peptide, (vi) anti-CD24 scFv, (vii) a transmembrane domain II and (viii) a costimulatory domain, an activation domain or both; wherein (A) and (B) are separated by a self-cleaving peptide.

According to one embodiment, the DNA construct encodes, from 5' to 3', (i) a leader peptide, (ii) anti-CD24 scFv, (iii) a transmembrane domain I, (iv) a costimulatory domain, (v) a self-cleaving peptide, (vi) a leader peptide, (vii) anti-HER2 scFv, (viii) a transmembrane domain II and (ix) an activation domain. According to another embodiment, the DNA construct encodes, from 5' to 3', (i) a leader peptide, (ii) anti-HER2 scFv, (iii) a transmembrane domain II, (iv) an activation domain, (v) a self-cleaving peptide, (vi) a leader peptide, (vii) anti-CD24 scFv, (viii) a transmembrane domain I, and (ix) a costimulatory domain.

All definitions and embodiments used in previous aspects, and in particular those related to CARs, their parts and domains as well as to DNA constructs and T-cells are encompassed and embedded herein.

According any one of the above embodiments, the self-cleaving peptide is a peptide having the SEQ ID NO: 14 or an active analog thereof. According to another embodiment, the self-cleaving peptide is IRES peptide or an analog thereof. According to another embodiment, the self-cleaving peptide is encoded by a DNA sequence SEQ ID NO: 15 or a variant thereof.

The terms "variant", "DNA variant", "sequence variant", "polynucleotide variant" and "variant of SEQ ID NO: X" are used herein interchangeably and refer to a DNA polynucleotide having at least 70% sequence identity to the parent polynucleotide, wherein X is a number of a sequence. The variant may include mutations such as deletion, addition or substitution such that the mutations do not change the open reading frame and the polynucleotide encodes a peptide or a protein having a substantially similar structure and function as the peptide or a protein encoded by the parent polynucleotide. According to some embodiments, the variants are conservative variants. The term "conservative variants" as used herein refers to variants in which a change of one or more nucleotides in a given codon position results in no alteration in the amino acid encoded at that position. Thus, the peptide or the protein encoded by the conservative variants has 100% sequence identity to the peptide or the protein encoded by the parent polynucleotide. According to some embodiments, the variant is a non-conservative variant encoding to a peptide or a protein being a conservative analog of the peptide of the protein encoded by the parent polynucleotide. According to some embodiments, the variant has at least 75%, at least 80% at least 85%, at least 90%, at least 95%, at least 98% or at least 99% sequence identity to the parent polynucleotide.

According to some embodiments, the CARs of the present invention are encoded by two or more different DNA constructs. According to one embodiment, the two CARs of the present invention are encoded by two different DNA constructs.

In some embodiments, the present invention provides a T-cell comprising two different DNA constructs, wherein the first DNA construct comprises a sequence encoding, from 5' to 3', (i) a leader peptide, (ii) anti-CD138 scFv, (iii) a transmembrane domain I (TM-I) and (iv) a costimulatory domain, an activation domain or both, and the second DNA construct comprises a sequence encoding from 5' to 3' (i) a leader peptide, (ii) anti-HER2 scFv, (iii) a transmembrane domain II (TM-II) and (iv) a costimulatory domain, an activation domain or both. According to one embodiment, the first DNA construct comprises a sequence encoding, from 5' to 3', (i) a leader peptide, (ii) anti-CD138 scFv, (iii) a TM-I and (iv) a costimulatory domain. According to another embodiment, the second DNA construct comprises a sequence encoding (i) a leader peptide, (ii) anti-HER2 scFv, (iii) a TM-II and (iv) an activation domain. According to one embodiment, the first DNA construct comprises a sequence encoding, from 5' to 3', (i) a leader peptide, (ii) anti-CD138 scFv, (iii) a TM-I and (iv) a costimulatory domain and the second DNA construct comprises a sequence encoding (i) a leader peptide, (ii) anti-HER2 scFv, (iii) a TM-II and (iv) an activation domain.

In some embodiments, the present invention provides a T-cell comprising two different DNA constructs, wherein the first DNA construct comprises a sequence encoding, from 5' to 3', (i) a leader peptide, (ii) anti-CD138 scFv, (iii) a transmembrane domain I (TM-I) and (iv) a costimulatory domain, an activation domain or both, and the second DNA construct comprises a sequence encoding from 5' to 3' (i) a leader peptide, (ii) anti-CD24 scFv, (iii) a transmembrane domain II (TM-II) and (iv) a costimulatory domain, an activation domain or both. According to one embodiment, the first DNA construct comprises a sequence encoding, from 5' to 3', (i) a leader peptide, (ii) anti-CD138 scFv, (iii) a TM-I and (iv) a costimulatory domain. According to another embodiment, the second DNA construct comprises a sequence encoding (i) a leader peptide, (ii) anti-CD24 scFv, (iii) a TM-II and (iv) an activation domain. According to one embodiment, the first DNA construct comprises a sequence encoding, from 5' to 3', (i) a leader peptide, (ii) anti-CD138 scFv, (iii) a TM-I and (iv) a costimulatory domain and the second DNA construct comprises a sequence encoding (i) a leader peptide, (ii) anti-CD24 scFv, (iii) a TM-II and (iv) an activation domain.

In some embodiments, the present invention provides a T-cell comprising two different DNA constructs, wherein the first DNA construct comprises a sequence encoding, from 5' to 3', (i) a leader peptide, (ii) anti-HER2 scFv, (iii) a transmembrane domain I (TM-I) and (iv) a costimulatory domain, an activation domain or both, and the second DNA construct comprises a sequence encoding from 5' to 3' (i) a leader peptide, (ii) anti-CD24 scFv, (iii) a transmembrane domain II (TM-II) and (iv) a costimulatory domain, an activation domain or both. According to one embodiment, the first DNA construct comprises a sequence encoding, from 5' to 3', (i) a leader peptide, (ii) anti-HER2 scFv, (iii) a TM-I and (iv) a costimulatory domain. According to another embodiment, the second DNA construct comprises a sequence encoding (i) a leader peptide, (ii) anti-CD24 scFv, (iii) a TM-II and (iv) an activation domain. According to one embodiment, the first DNA construct comprises a sequence encoding, from 5' to 3', (i) a leader peptide, (ii) anti-HER2 scFv, (iii) a TM-I and (iv) a costimulatory domain and the second DNA construct comprises a sequence encoding (i) a leader peptide, (ii) anti-CD24 scFv, (iii) a TM-II and (iv) an activation domain.

According to some embodiments, the anti-CD138 scFv comprises amino acid sequence SEQ ID NO: 28. According to some embodiments, the anti-CD138 scFv is encoded by a DNA sequence SEQ ID NO: 16 or a variant thereof. According to some embodiments, the anti-HER2 scFv comprises amino acid sequence SEQ ID NO: 29. According to some embodiments, the anti-CD138 scFv is encoded by a DNA sequence SEQ ID NO: 17 or a variant thereof. According to some embodiments, the anti-CD24 scFv comprises amino acid sequence SEQ ID NO: 33. According to some embodiments, the anti-CD138 scFv is encoded by a DNA sequence SEQ ID NO: 18 or a variant thereof.

According to some embodiments, the leader peptide has amino acid sequence SEQ ID NO: 30. According to another embodiment, the leader peptide is encoded by DNA sequence SEQ ID NO: 37.

According some embodiments, the costimulatory domain has amino acid sequence SEQ ID NO: 9. According other embodiments, the costimulatory domain is encoded by a DNA sequence SEQ ID NO: 19, or a variant thereof.

According some embodiments, the activation domain has amino acid sequence SEQ ID NO: 8. According other embodiments, the activation domain is encoded by a DNA sequence SEQ ID NO: 20, or a variant thereof.

According to some embodiments, the costimulatory domain is encoded by a DNA sequence SEQ ID NO: 19 and the activation domain is encoded by a DNA sequence SEQ ID NO: 20

According to some embodiments, the transmembrane domain I comprises amino acid sequence SEQ ID NO: 31. According to one embodiment, the transmembrane domain I is encoded by a DNA sequence SEQ ID NO: 34.

According to other embodiments, the transmembrane domain II has amino acid sequence SEQ ID NO: 32 According other embodiments, the transmembrane domain II is encoded by a DNA sequence SEQ ID NO: 35.

According to one embodiment, two CARs are encoded by one DNA construct comprising, DNA sequences SEQ ID NO: SEQ ID NO: 16, 17, 19 and 20.

According to one embodiment, two CARs are encoded by one DNA construct comprising, DNA sequences SEQ ID NO: SEQ ID NO: 16, 18, 19 and 20.

According to one embodiment, two CARs are encoded by one DNA construct comprising, DNA sequences SEQ ID NO: SEQ ID NO: 17, 18, 19 and 20.

According to some embodiments, the DNA construct comprises SEQ ID NO: 24 or a variant thereof. According to another embodiment, the DNA construct comprises SEQ ID NO: 25 or a variant thereof. According to a further embodiment, the DNA construct comprises from 5' to 3' SEQ ID NO: 24 and SEQ ID NO: 25. According to another embodiment, the DNA construct comprises from 5' to 3' SEQ ID NO: 25 and SEQ ID NO: 24.

According to some embodiments, the DNA construct comprises SEQ ID NO: 26 or a variant thereof. According to another embodiment, the DNA construct comprises from 5' to 3' SEQ ID NO: 24 and SEQ ID NO: 26. According to another embodiment, the DNA construct comprises from 5' to 3' SEQ ID NO: 26 and SEQ ID NO: 24.

According to some embodiments, the DNA construct comprises SEQ ID NO: 27 or a variant thereof. According to another embodiment, the DNA construct comprises from 5' to 3' SEQ ID NO: 27 and SEQ ID NO: 26. According to another embodiment, the DNA construct comprises from 5' to 3' SEQ ID NO: 26 and SEQ ID NO: 27.

According to one embodiment, the present invention provides a T-cell comprising a DNA construct encoding two CARs of the present invention, wherein the DNA construct has SEQ ID NO: 21. According to another embodiment, the DNA construct is a variant, e.g. a conservative variant of SEQ ID NO: 21.

According to one embodiment, the present invention provides a T-cell comprising a DNA construct encoding two CARs of the present invention, wherein the DNA construct has SEQ ID NO: 22. According to another embodiment, the DNA construct is a variant, e.g. a conservative variant of SEQ ID NO: 22.

According to one embodiment, the present invention provides a T-cell comprising a DNA construct encoding two CARs of the present invention, wherein the DNA construct has SEQ ID NO: 23. According to another embodiment, the DNA construct is a variant, e.g. a conservative variant of SEQ ID NO: 23.

According to some embodiments, the present invention provides a T-cell comprising two DNA constructs encoding two CARs of the present invention, wherein the first DNA construct comprises the DNA sequence SEQ ID NO: 24 and the second DNA construct comprises the DNA sequence SEQ ID NO: 25. According to one embodiment, the first DNA construct has a DNA sequence being a variant, such as conservative variant of SEQ ID NO: 24. According to one embodiment, the second DNA construct has a DNA sequence being a variant, such as conservative variant of SEQ ID NO: 25. According to a further embodiment, the T-cell comprising two DNA constructs, wherein the first DNA construct comprises the DNA being a variant of SEQ ID NO: 24 and the second DNA construct has a DNA sequence being a variant of SEQ ID NO: 25.

According to some embodiments, the present invention provides a T-cell comprising two DNA constructs encoding two CARs of the present invention, wherein the first DNA construct comprises the DNA sequence SEQ ID NO: 24 and the second DNA construct comprises the DNA sequence SEQ ID NO: 26. According to one embodiment, the first DNA construct has a DNA sequence being a variant, such as conservative variant of SEQ ID NO: 24. According to one embodiment, the second DNA construct has a DNA sequence being a variant, such as conservative variant of SEQ ID NO: 26. According to a further embodiment, the T-cell comprising two DNA constructs, wherein the first DNA construct comprises the DNA being a variant of SEQ ID NO: 24 and the second DNA construct has a DNA sequence being a variant of SEQ ID NO: 26.

According to some embodiments, the present invention provides a T-cell comprising two DNA constructs encoding two CARs of the present invention, wherein the first DNA construct comprises the DNA sequence SEQ ID NO: 27 and the second DNA construct comprises the DNA sequence SEQ ID NO: 26. According to one embodiment, the first DNA construct has a DNA sequence being a variant, such as conservative variant of SEQ ID NO: 27. According to one embodiment, the second DNA construct has a DNA sequence being a variant, such as conservative variant of SEQ ID NO: 26. According to a further embodiment, the T-cell comprising two DNA constructs, wherein the first DNA construct comprises the DNA being a variant of SEQ ID NO: 27 and the second DNA construct has a DNA sequence being a variant of SEQ ID NO: 26.

According to any one of the above embodiments, the T-cells comprising the DNA constructs of the present invention express or capable of expressing the CARs encoded by the DNA constructs. According to one embodiment, the T-cell is a CD4+ T-cell. According to another embodiment, the T-cell is a CD8+ T-cell The word "expression" or "express" as used herein in reference to a DNA construct means the transcriptional and/or translational product of that construct. The level of expression of a DNA molecule in a cell may be determined on the basis of either the amount of corresponding mRNA that is present within the cell or the amount of protein encoded by that DNA produced by the cell. According to some embodiments, the expression is a conditional expression.

According to another aspect, the present invention provides a DNA construct encoding the dual CARs of the present invention, i.e. DNA construct encoding two CARs. In some embodiments, the present invention provides a DNA construct encoding for: (A) from 5' to 3': (i) a leader peptide, (ii) an antigen binding domain selected from anti-CD138, anti-HER2 and anti-CD24 (iii) transmembrane domain I, and (iv) a costimulatory domain, an activation domain or both; and (B) from 5' to 3' (v) a leader peptide, (vi) an antigen binding domain selected from anti-CD138, anti-HER2 and anti-CD24 (vii) transmembrane domain II and (viii) an activation domain, a costimulatory domain or both; wherein (A) and (B) are separated by a self-cleaving peptide, and wherein the an antigen binding domains of (ii) and of (vi) are different.

In one embodiment, the DNA construct encodes for: (A) from 5' to 3': (i) a leader peptide, (ii) anti-CD138 scFv, (iii) a transmembrane domain I, and (iv) a costimulatory domain, an activation domain or both; and (B) from 5' to 3' (v) a leader peptide, (vi) anti-HER2 scFv, (vii) a transmembrane domain II and (viii) a costimulatory domain, an activation domain or both; wherein (A) and (B) are separated by a self-cleaving peptide. According to another embodiment, the DNA construct encodes, from 5' to 3', (i) a leader peptide, (ii) anti-CD138 scFv, (iii) a transmembrane domain I, (iv) a costimulatory domain, (v) a self-cleaving peptide, (vi) a leader peptide, (vii) anti-HER2 scFv, (viii) a transmembrane domain II and (ix) an activation domain. According to another embodiment, the DNA construct encodes, from 5' to 3', (i) a leader peptide, (ii) anti-HER2 scFv, (iii) a transmembrane domain II, (iv) an activation domain, (v) a self-cleaving peptide, (vi) a leader peptide, (vii) anti-CD138 scFv, (viii) a transmembrane domain I, and (ix) a costimulatory domain.

In one embodiment, the DNA construct for: (A) from 5' to 3': (i) a leader peptide, (ii) anti-CD138 scFv, (iii) a transmembrane domain I, and (iv) a costimulatory domain, an activation domain or both; and (B) from 5' to 3': (v) a leader peptide, (vi) anti-CD24 scFv, (vii) a transmembrane domain II and (viii) a costimulatory domain, an activation domain or both, wherein (A) and (B) are separated by a self-cleaving peptide. According to one embodiment, the DNA construct encodes, from 5' to 3', (i) a leader peptide, (ii) anti-CD138 scFv, (iii) a transmembrane domain I, (iv) a costimulatory domain, (v) a self-cleaving peptide, (vi) a leader peptide, (vii) anti-CD24 scFv, (viii) a transmembrane domain II and (ix) an activation domain. According to another embodiment, the DNA construct encodes, from 5' to 3', (i) a leader peptide, (ii) anti-CD24 scFv, (iii) a transmembrane domain II, (iv) an activation domain, (v) a self-cleaving peptide, (vi) a leader peptide, (vii) anti-CD138 scFv, (viii) a transmembrane domain I, and (ix) a costimulatory domain.

In one embodiment, the present invention provides a DNA construct encoding for: (A) from 5' to 3': (i) a leader peptide, (ii) anti-HER2 scFv, (iii) a transmembrane domain I, and (iv) a costimulatory domain, an activation domain or both; and (B) from 5' to 3': (v) a leader peptide, (vi) anti-CD24 scFv, (vii) a transmembrane domain II and (viii) a costimulatory domain, an activation domain or both; wherein (A) and (B) are separated by a self-cleaving peptide. According to one embodiment, the DNA construct encodes, from 5' to 3', (i) a leader peptide, (ii) anti-CD24 scFv, (iii) a transmembrane domain I, (iv) a costimulatory domain, (v) a self-cleaving peptide, (vi) a leader peptide, (vii) anti-HER2 scFv, (viii) a transmembrane domain II and (ix) an activation domain. According to another embodiment, the DNA construct encodes, from 5' to 3', (i) a leader peptide, (ii) anti-HER2 scFv, (iii) a transmembrane domain II, (iv) an activation domain, (v) a self-cleaving peptide, (vi) a leader peptide, (vii) anti-CD24 scFv, (viii) a transmembrane domain I, and (ix) a costimulatory domain.

All definitions and embodiments used in previous aspects, and in particular those related to CARs, their parts and domains as well as to DNA constructs and T-cells are encompassed and embedded herein.

According to one embodiment, the self-cleaving peptide is a peptide having the SEQ ID NO: 14 or an active analog thereof. According to another embodiment, the self-cleaving peptide is IRES peptide or an analog thereof. According to another embodiment, the self-cleaving peptide is encoded by a DNA sequence SEQ ID NO: 15 or a variant thereof.

According to some embodiments, the anti-CD138 scFv comprises amino acid sequence SEQ ID NO: 28. According to one embodiment, the anti-CD138 scFv is encoded by a DNA sequence SEQ ID NO: 16 or a variant thereof. Thus according to one embodiment, the DNA construct encoding anti-CD138 scFv comprises SEQ ID NO: 16. According to other embodiments, such DNA construct comprises a variant, such as conservative variant, of SEQ ID NO: 16.

According to other embodiments, the anti-HER2 scFv is encoded by a DNA sequence SEQ ID NO: 17 or a variant thereof. In one embodiment, the DNA construct encoding anti-HER2 scFv comprises SEQ ID NO: 17. According to other embodiments, such DNA construct comprises a variant, such as conservative variant, of SEQ ID NO: 17.

According to some embodiments, the anti-CD24 scFv comprises amino acid sequence SEQ ID NO: 33. According to other embodiments, the anti-CD24 scFv is encoded by a DNA sequence SEQ ID NO: 18 or a variant thereof. In one embodiment, the DNA construct encoding anti-HER2 scFv comprises SEQ ID NO: 18. According to other embodiments, such DNA construct comprises a variant, such as conservative variant, of SEQ ID NO: 18.

According any one of the above embodiments, the self-cleaving peptide is a peptide having the SEQ ID NO: 14 or an active analog thereof. According to another embodiment, the self-cleaving peptide is IRES peptide or an analog thereof. According to another embodiment, the self-cleaving peptide is encoded by a DNA sequence SEQ ID NO: 15 or a variant thereof.

According to some embodiments, the leader peptide has amino acid sequence SEQ ID NO: 30. According to another embodiment, the leader peptide is encoded by DNA sequence SEQ ID NO: 37.

According some embodiments, the costimulatory domain has amino acid sequence SEQ ID NO: 9. According other embodiments, the costimulatory domain is encoded by a DNA sequence SEQ ID NO: 19, or a variant thereof.

According some embodiments, the activation domain has amino acid sequence SEQ ID NO: 8. According other embodiments, the activation domain is encoded by a DNA sequence SEQ ID NO: 20, or a variant thereof.

According to some embodiments, the DNA construct comprises SEQ ID NO: 19 and sequence SEQ ID NO: 20

According to one embodiment, the DNA construct comprises DNA sequences SEQ ID NOs: SEQ ID NO: 16, 17, 19 and 20.

According to one embodiment, the DNA construct comprises DNA sequences SEQ ID NOs: SEQ ID NO: 16, 18, 19 and 20.

According to one embodiment, two DNA construct comprises DNA sequences SEQ ID NOs: SEQ ID NO: 17, 18, 19 and 20.

According to some embodiments, the transmembrane domain I comprises amino acid sequence SEQ ID NO: 31. According other embodiments, the transmembrane domain I is encoded by a DNA sequence SEQ ID NO: 34.

According to further embodiments, the transmembrane domain II has amino acid sequence SEQ ID NO: 32. According to one embodiment, the transmembrane domain II is encoded by a DNA sequence SEQ ID NO: 35.

According to some embodiments, the DNA construct comprises SEQ ID NO: 24 or a variant thereof. According to another embodiment, the DNA construct comprises SEQ ID NO: 25 or a variant thereof. According to another embodiment, the DNA construct comprises from 5' to 3' SEQ ID NO: 24 and SEQ ID NO: 25. According to another embodiment, the DNA construct comprises from 5' to 3' SEQ ID NO: 25 and SEQ ID NO: 24.

According to some embodiments, the DNA construct comprises SEQ ID NO: 26 or a variant thereof. According to another embodiment, the DNA construct comprises from 5' to 3' SEQ ID NO: 24 and SEQ ID NO: 26. According to another embodiment, the DNA construct comprises from 5' to 3' SEQ ID NO: 26 and SEQ ID NO: 24.

According to some embodiments, the DNA construct comprises SEQ ID NO: 27 or a variant thereof. According to another embodiment, the DNA construct comprises from 5' to 3' SEQ ID NO: 27 and SEQ ID NO: 26. According to another embodiment, the DNA construct comprises from 5' to 3' SEQ ID NO: 26 and SEQ ID NO: 27.

According to one embodiment, the present invention provides a DNA construct comprising SEQ ID NO: 21. According to another embodiment, the DNA construct comprises is a variant, e.g. a conservative variant of SEQ ID NO: 21.

According to one embodiment, the present invention provides a DNA construct comprising SEQ ID NO: 22. According to another embodiment, the DNA construct comprises a variant, e.g. a conservative variant of SEQ ID NO: 22.

According to one embodiment, the present invention provides a DNA construct comprising SEQ ID NO: 23.

According to another embodiment, the DNA construct comprises a variant, e.g. a conservative variant of SEQ ID NO: 23.

According to another aspect, the present invention provides a vector comprising the DNA construct of the present invention. According to one embodiment, the vector comprises a DNA construct comprising DNA sequence SEQ ID NO: 21. According to another embodiment, the DNA variant is a variant of DNA sequence SEQ ID NO: 21. According to some embodiment, the vector comprises a DNA construct comprising DNA sequence SEQ ID NO: 22. According to another embodiment, the DNA variant is a variant of DNA sequence SEQ ID NO: 22. According to one embodiment, the vector comprises a DNA construct comprising DNA sequence SEQ ID NO: 23. According to another embodiment, the DNA variant is a variant of DNA sequence SEQ ID NO: 23.

The terms "vector" and "expression vector" are used herein interchangeably and refer to any viral or non-viral vector such as plasmid, virus, retrovirus, bacteriophage, cosmid, artificial chromosome (bacterial or yeast), phage, binary vector in double or single stranded linear or circular form, or nucleic acid, sequence which is able to transform host cells and optionally capable of replicating in a host cell. The vector may be integrated into the cellular genome or may exist extrachromosomally (e.g., autonomous replicating plasmid with an origin of replication). The vector may contain an optional marker suitable for use in the identification of transformed cells, e.g., tetracycline resistance or ampicillin resistance. A cloning vector may or may not possess the features necessary for it to operate as an expression vector.

According to other embodiments, the vector is a virus, e.g. a modified or engineered virus. The modification of a vector may include mutations, such as deletion or insertion mutation, gene deletion or gene inclusion. In particular, a mutation may be done in one or more regions of the viral genome. Such mutations may be introduced in a region related to internal structural proteins, replication, or reverse transcription function. Other examples of vector modification are deletion of certain genes constituting the native infectious vector such as genes related to the virus' pathogenicity and/or to its ability to replicate.

According to one embodiment, the vector is a viral vector. Any virus can be used by the methods disclosed herein. The virus can be a dsDNA virus (e.g. Adenoviruses, Herpesviruses, Poxviruses), a single stranded "plus" sense DNA virus (e.g., Parvoviruses) a double stranded RNA virus (e.g., Reoviruses), a single stranded sense RNA virus (e.g. Picornaviruses, Togaviruses), a single stranded "minus" sense RNA virus (e.g. Orthomyxoviruses, Rhabdoviruses), a single stranded sense RNA virus with a DNA intermediate (e.g. Retroviruses), or a double stranded reverse transcribing virus (e.g. Hepadnaviruses). In certain non-limiting embodiments of the present invention, the virus is poliovirus (PV), rhinovirus, influenza virus including avian flu (e.g. H5N1 subtype of influenza A virus), severe acute respiratory syndrome (SARS) coronavirus, Human Immunodeficiency Virus (HIV), Hepatitis B Virus (HBV), Hepatitis C Virus (HCV), infectious bronchitis virus, ebolavirus, Marburg virus, dengue fever virus (Flavivirus serotypes), West Nile disease virus, Epstein-Barr virus (EBV), yellow fever virus, Ebola (ebolavirus), chickenpox (varicella-zoster virus), measles (a paramyxovirus), mumps (a paramyxovirus), rabies (Lyssavirus), human papillomavirus, Kaposi's sarcoma-associated herpesvirus, Herpes Simplex Virus (HSV Type 1), or genital herpes (HSV Type 2). According to some embodiments, the vector is a virus selected from lentivirus, adenovirus, modified adenovirus and retrovirus. In one particular embodiment, the vector is lentivirus. According to any one of the above embodiments, the virus is a non-pathogenic virus or a modified virus lacking pathogenic genes.

According to another aspect, the present invention provides a cell comprising the DNA construct or the vector of the present invention. According to some embodiments, the cell is prokaryotic or eukaryotic cells. According to another embodiment, the cell is non-human or human mammal cell. According to some embodiments, the cell is human cell. According to some particular embodiment, the cell is T-cell. According to one embodiment, the T-cell is selected from CD4+ T-cell and a CD8+ T-cell.

According to another aspect, the present invention provides a pharmaceutical composition comprising the T-cells of the present invention and a pharmaceutically acceptable carrier.

All definitions and embodiments used in previous aspects, and in particular those related to CARs, their parts and domains as well as to DNA constructs and T-cells are encompassed and embedded herein.

The term "pharmaceutical composition" as used herein refers to a composition comprising the T-cells of the present invention formulated together with one or more pharmaceutically acceptable carriers.

Formulation of the pharmaceutical composition may be adjusted according to applications. In particular, the pharmaceutical composition may be formulated using a method known in the art so as to provide rapid, continuous or delayed release of the active ingredient after administration to mammals. For example, the formulation may be any one selected from among plasters, granules, lotions, liniments, lemonades, aromatic waters, powders, syrups, ophthalmic ointments, liquids and solutions, aerosols, extracts, elixirs, ointments, fluidextracts, emulsions, suspensions, decoctions, infusions, ophthalmic solutions, tablets, suppositories, injections, spirits, capsules, creams, troches, tinctures, pastes, pills, and soft or hard gelatin capsules. According to one embodiment, the composition is formulated as a liquid formulation. According to another embodiment, the composition is formulated as a solution for injection.

The term "pharmaceutically acceptable carrier" or "pharmaceutically acceptable excipient" as used herein refers to any and all solvents, dispersion media, preservatives, antioxidants, coatings, isotonic and absorption delaying agents, surfactants, fillers, disintegrants, binders, diluents, lubricants, glidants, pH adjusting agents, buffering agents, enhancers, wetting agents, solubilizing agents, surfactants, antioxidants the like, that are compatible with pharmaceutical administration. The use of such media and agents for pharmaceutically active substances is well known in the art. The compositions may contain other active compounds providing supplemental, additional, or enhanced therapeutic functions.

The terms "pharmaceutically acceptable" and "pharmacologically acceptable" include molecular entities and compositions that do not produce an adverse, allergic, or other untoward reactions when administered to an animal, or human, as appropriate. For human administration, preparations should meet sterility, pyrogenicity, general safety, and purity standards as required by a government drug regulatory agency, e.g., the United States Food and Drug Administration (FDA) Office of Biologics standards.

The composition of the present invention may be administered by any known method. The terms "administering" or "administration of" a composition to a subject can be carried out using one of a variety of methods known to those skilled in the art. For example, a compound or an agent can be administered, intravenously, arterially, intradermally, intramuscularly, intraperitonealy, intravenously, subcutaneously, ocularly, sublingually, orally (by ingestion), intranasally (by inhalation), intraspinally, intracerebrally, and transdermally (by absorption, e.g., through a skin duct). A compound or agent can also appropriately be introduced by rechargeable or biodegradable polymeric devices or other devices, e.g., patches and pumps, or formulations, which provide for the extended, slow or controlled release of the compound or agent. Administering can also be performed, for example, once, a plurality of times, and/or over one or more extended periods. In some embodiments, the administration includes both direct administration, including self-administration, and indirect administration, including the act of prescribing a drug. For example, as used herein, a physician who instructs a patient to self-administer a drug, or to have the drug administered by another and/or who provides a patient with a prescription for a drug is administering the drug to the patient. According to one embodiments, the pharmaceutical composition is administered parenterally, i.e. not orally. According to one embodiments, the pharmaceutical composition is administered systemically. According to another embodiment, the pharmaceutical composition is administered locally. According to one embodiments, the pharmaceutical composition is administered intravenously. According to another embodiment, the pharmaceutical composition is administered intramuscularly.

According to another embodiment, the pharmaceutical composition comprises T-cell comprising the DNA construct of the present invention. According to one embodiment, the T-cell comprises one construct encoding the 2 CARs of the present invention. According to another embodiment, the T-cell comprises two constructs; each encoding one separate CAR is the present invention.

According to one embodiment, the pharmaceutical composition comprises a plurality of T-cells genetically modified to express at least two distinct separate chimeric antigen receptors (CARs), wherein the first CAR comprises anti-CD138 scFv and the second CAR comprises anti-HER2 scFv. According to some such embodiments, the first CAR comprises amino acid sequences SEQ ID NO: 28 and SEQ ID NO: 9. According to another embodiment, the second CAR comprises amino acid sequences SEQ ID NO: 29 and SEQ ID NO: 8. According to one embodiment, the first CAR comprises amino acid sequences SEQ ID NO: 28 and SEQ ID NO: 9 and the second CAR comprises amino acid sequences SEQ ID NO: 29 and SEQ ID NO: 8. According to one such embodiments, the first CAR has the amino acid sequence SEQ ID NO: 10 or being an analog thereof and the second CAR has the amino acid sequence SEQ ID NO: 11 or being an analog thereof. According to a one embodiment, the T-cells are selected from CD4+ and CD8+ cells. Thus in one embodiment, the present invention provides a pharmaceutical composition comprising CD4+ and/or CD8+ T-cells genetically modified to express two distinct separate CARs, wherein the first CAR consists of amino acid sequence SEQ ID NO: 10 and the second CAR consists of amino acid sequence SEQ ID NO: 11.

According to another embodiment, the pharmaceutical composition comprises a plurality of T-cells genetically modified to express two distinct separate CARs, wherein the first CAR comprises anti-CD138 scFv and the second CAR comprises anti-CD24 scFv. According to some such embodiments, the first CAR comprises amino acid sequences SEQ ID NO: 28 and SEQ ID NO: 9. According to another embodiment, the second CAR comprises amino acid sequences SEQ ID NO: 33 and SEQ ID NO: 8. According to one embodiment, the first CAR comprises amino acid sequences SEQ ID NO: 28 and SEQ ID NO: 9 and the second CAR comprises amino acid sequences SEQ ID NO: 33 and SEQ ID NO: 8. According to one such embodiments, the first CAR has the amino acid sequence SEQ ID NO: 10 or being an analog thereof and the second CAR has the amino acid sequence SEQ ID NO: 12 or being an analog thereof. According to a one embodiment, the T-cells are selected from CD4+ and CD8+ cells. Thus in one embodiment, the present invention provides a pharmaceutical composition comprising CD4+ and/or CD8+ T-cells genetically modified to express two distinct separate CARs, wherein the first CAR consists of amino acid sequence SEQ ID NO: 10 and the second CAR consists of amino acid sequence SEQ ID NO: 12.

According to yet another embodiment, the pharmaceutical composition comprises a plurality of T-cells genetically modified to express two distinct separate CARs, wherein the first CAR comprises anti-HER2 scFv and the second CAR comprises anti-CD24 scFv. According to another embodiment, the present invention provides CD8+ T-cells genetically modified to express two distinct separate CARs, wherein the first CAR comprises anti-HER2 scFv and the second CAR comprises anti-CD24 scFv. According to some such embodiments, the first CAR comprises amino acid sequences SEQ ID NO: 29 and SEQ ID NO: 9. According to another embodiment, the second CAR comprises amino acid sequences SEQ ID NO: 33 and SEQ ID NO: 8. According to one embodiment, the first CAR comprises amino acid sequences SEQ ID NO: 29 and SEQ ID NO: 9 and the second CAR comprises amino acid sequences SEQ ID NO: 33 and SEQ ID NO: 8. According to one such embodiments, the first CAR has the amino acid sequence SEQ ID NO: 13 or being an analog thereof and the second CAR has the amino acid sequence SEQ ID NO: 12 or being an analog thereof. According to a one embodiment, the T-cells are selected from CD4+ and CD8+ cells. Thus in one embodiment, the present invention provides a pharmaceutical composition comprising CD4+ and/or CD8+ T-cells genetically modified to express two distinct separate CARs, wherein the first CAR consists of amino acid sequence SEQ ID NO: 13 and the second CAR consists of amino acid sequence SEQ ID NO: 12. According to some embodiments, the T-cells are capable of expressing the CARs. According to another embodiment, the T-cells express the CARs.

According to one embodiment, the pharmaceutical composition comprises T-cells comprising the DNA construct of the present invention. According to one embodiment, the DNA construct comprises DNA sequence SEQ ID NO: 21 or a variant thereof. According to some embodiment, the DNA construct comprises DNA sequence SEQ ID NO: 22 or variant of DNA sequence SEQ ID NO: 22. According to one embodiment, the DNA construct comprises DNA sequence SEQ ID NO: 23 or variant is thereof.

According to any one of the above embodiments, the pharmaceutical composition of the present invention is for use in treating cancer. According to one embodiment, the cancer is ovarian cancer.

According to some embodiments, the Dual CAR-T cells of the present invention are for use in treating other type of cancers overexpressing at least two of the antigens CD138, CD24 and HER2. According to one embodiment, the T-cell comprising a pair of CARs against (i) CD138 and CD24; (ii) CD138 and CD24; or (ii) HER2 and CD24 are useful for treating solid tumors selected from breast cancer, pancreatic and renal cancer since all three antigens overexpressed in these tumors.

The term "ovarian cancer" as used herein refers to Epithelial ovarian cancer (EOC). 90% of ovarian cancers develop in the epithelium, the thin layer of tissue that covers the ovaries. EOC generally occurs in postmenopausal women.

The term "treating" a condition or patient as used herein refers to taking steps to obtain beneficial or desired results, including clinical results. Beneficial or desired clinical results include, but are not limited to, or ameliorating abrogating, substantially inhibiting, slowing or reversing the progression of a cancer substantially ameliorating or alleviating clinical or esthetical symptoms of a condition, substantially preventing the appearance of clinical symptoms of a disease, condition, and protecting from harmful or annoying symptoms. Treating further refers to accomplishing one or more of the following: (a) reducing the severity of the disorder; (b) limiting development of symptoms characteristic of the disorder(s) being treated; (c) limiting worsening of symptoms characteristic of the disorder(s) being treated; (d) limiting recurrence of the disorder(s) in patients that have previously had the disorder(s); and/or (e) limiting recurrence of symptoms in patients that were previously asymptomatic for the disorder(s).

In some embodiments, the present invention provides a pharmaceutical composition comprising T-cells genetically modified to express two distinct separate CARs, for use in treating ovarian cancer, wherein the first CAR anti-CD138 scFv and the second CAR comprises anti-HER2 scFv. According to a further embodiment, the present invention provides a pharmaceutical composition comprising CD4+ and/or CD8+ T-cells genetically modified to express two distinct separate CARs, wherein the first CAR comprises or consists of amino acid sequence SEQ ID NO: 10 and the second CAR consists of amino acid sequence SEQ ID NO: 11, wherein the pharmaceutical composition for use in treating ovarian cancer. According to any one of the above embodiments, the T-cell expressed the two CARs.

According to other embodiments, the present invention provides a pharmaceutical composition comprising T-cells genetically modified to express two distinct separate CARs, for use in treating ovarian cancer, wherein the first CAR anti-CD138 scFv and the second CAR comprises anti-CD24 ScFv. According to a further embodiment, the present invention provides a pharmaceutical composition comprising CD4+ and/or CD8+ T-cells genetically modified to express two distinct separate CARs, wherein the first CAR comprises or consists of amino acid sequence SEQ ID NO: 10 and the second CAR consists of amino acid sequence SEQ ID NO: 12, wherein the pharmaceutical composition for use in treating ovarian cancer. According to any one of the above embodiments, the T-cell expressed the two CARs.

According to certain embodiments, the present invention provides a pharmaceutical composition comprising T-cells genetically modified to express two distinct separate CARs, for use in treating ovarian cancer, wherein the first CAR anti-HER2 scFv and the second CAR comprises anti-CD24 scFv. According to a further embodiment, the present invention provides a pharmaceutical composition comprising CD4+ and/or CD8+ T-cells genetically modified to express two distinct separate CARs, wherein the first CAR comprises or consists of amino acid sequence SEQ ID NO: 13 and the second CAR consists of amino acid sequence SEQ ID NO: 12, wherein the pharmaceutical composition for use in treating ovarian cancer. According to any one of the above embodiments, the T-cell expressed the two CARs.

According to any one of the above aspects, the term treating encompasses increasing survival rate by at least 1.5, 2, 2.5 or 3 folds.

According to another aspect, the present invention provides a method of treating cancer in a subject in need thereof, comprising administering an effective amount of T-cells of the present invention. According to another embodiment, the method comprises administering the pharmaceutical composition comprising the T-cells of the present invention. According to one embodiment, the cancer is ovarian cancer.

According to a further aspect, the present invention provides a method of preparation of T-cells of the present invention. According to one embodiment, the present invention provides a method of preparation of T-cells genetically modified to express at least two distinct separate chimeric antigen receptors (CARs), wherein the first CAR comprises an antigen binding domain that binds specifically to CD138 and the second CAR comprises an antigen binding domain that binds specifically to HER2, said method comprises transfecting of T-cells with the DNA construct of the present invention encoding anti-CD138 scFv and anti-HER2 scFv.

According to another embodiment, the present invention provides a method of preparation of T-cells genetically modified to express at least two distinct separate chimeric antigen receptors (CARs), wherein the first CAR comprises an antigen binding domain that binds specifically to CD138 and the second CAR comprises an antigen binding domain that binds specifically to CD24, said method comprises transfecting of T-cells with the DNA construct of the present invention encoding anti-CD138 scFv and anti-CD24 scFv.

According to another embodiment, the present invention provides a method of preparation of T-cells genetically modified to express at least two distinct separate chimeric antigen receptors (CARs), wherein the first CAR comprises an antigen binding domain that binds specifically to HER2 and the second CAR comprises an antigen binding domain that binds specifically to CD24, said method comprises transfecting of T-cells with the DNA construct of the present invention encoding anti-HER2 scFv and anti-CD24 scFv.

All definitions and embodiments used in previous aspects, and in particular those related to CARs, their parts and domains as well as to DNA constructs and T-cells are encompassed and embedded herein.

The terms "transfection", "transduction", "transfecting" or "transducing" can be used interchangeably and are defined as a process of introducing a nucleic acid molecule to a cell. Nucleic acids are introduced to a cell using non-viral or viral-based methods. The nucleic acid molecules may be gene sequences encoding complete proteins or functional portions thereof. Non-viral methods of transfection include any appropriate transfection method that does not use viral DNA or viral particles as a delivery system to introduce the nucleic acid molecule into the cell. Exemplary non-viral transfection methods include calcium phosphate transfection, liposomal transfection, nucleofection, sonoporation, transfection through heat shock, magnetifection and electroporation. In some embodiments, the nucleic acid molecules are introduced into a cell using electroporation following standard procedures well known in the art. For viral-based methods of transfection any useful viral vector may be used in the methods described herein. Examples for viral vectors include, but are not limited to retroviral, adenoviral, lentiviral and adeno-associated viral vectors. In some embodiments, the nucleic acid molecules are introduced into a cell using a retroviral vector following standard procedures well known in the art.

According to one embodiment, the T-cells are CD4+ T-cells. According to another embodiment, the T-cells are CD8+ cells.

According to one embodiment, the method comprises transducing T cells with a DNA construct encoding two CARs, wherein the construct comprises DNA sequences SEQ ID NOs:16, 19, 17 and 20. According to some embodiments, the DNA construct comprises SEQ ID NO: 24 or a variant thereof. According to another embodiment, the DNA construct comprises SEQ ID NO: 25 or a variant thereof. According to another embodiment, the DNA construct comprises from 5' to 3' SEQ ID NO: 24 and SEQ ID NO: 25. According to another embodiment, the DNA construct comprises from 5' to 3' SEQ ID NO: 25 and SEQ ID NO: 24.

According to one embodiment, a DNA construct encoding two CARs of the present invention has DNA sequence SEQ ID NO: 21. According to another embodiment, the DNA construct is a variant, e.g. a conservative variant, of SEQ ID NO: 21.

According to one embodiment, the method comprises transducing T cells with two DNA constructs each encoding one separate CAR of the present invention, wherein the first DNA construct comprises the DNA sequence SEQ ID NO: 24 and the second DNA construct comprises the DNA sequence SEQ ID NO: 25. According to one embodiment, the first DNA construct has a DNA sequence being a variant, such as conservative variant of SEQ ID NO: 24. According to one embodiment, the second DNA construct has a DNA sequence being a variant, such as conservative variant of SEQ ID NO: 25. According to a further embodiment, the T-cell comprising two DNA constructs, wherein the first DNA construct comprises the DNA being a variant of SEQ ID NO: 24 and the second DNA construct has a DNA sequence being a variant of SEQ ID NO: 25.

According to one embodiment, the method comprises transducing T cells with a DNA construct encoding two CARs, wherein the construct comprises DNA sequences SEQ ID NOs: 16, 19, 18 and 20. According to some embodiments, the DNA construct comprises SEQ ID NO: 24 or a variant thereof. According to another embodiment, the DNA construct comprises SEQ ID NO: 26 or a variant thereof. According to another embodiment, the DNA construct comprises from 5' to 3' SEQ ID NO: 24 and SEQ ID NO: 26. According to another embodiment, the DNA construct comprises from 5' to 3' SEQ ID NO: 26 and SEQ ID NO: 24.

According to one embodiment, a DNA construct encoding two CARs of the present invention has SEQ ID NO: 22. According to another embodiment, the DNA construct is a variant, e.g. a conservative variant, of SEQ ID NO: 22.

According to one embodiment, the method comprises transducing T cells with two DNA constructs each encoding one separate CAR of the present invention, wherein the first DNA construct comprises the DNA sequence SEQ ID NO: 24 and the second DNA construct comprises the DNA sequence SEQ ID NO: 26. According to one embodiment, the first DNA construct has a DNA sequence being a variant, such as conservative variant of SEQ ID NO: 24. According to one embodiment, the second DNA construct has a DNA sequence being a variant, such as conservative variant of SEQ ID NO: 26. According to a further embodiment, the T-cell comprising two DNA constructs, wherein the first DNA construct comprises the DNA being a variant of SEQ ID NO: 24 and the second DNA construct has a DNA sequence being a variant of SEQ ID NO: 26.

According to one embodiment, the method comprises transducing T cells with oane DNA construct encoding two CARs, wherein the construct comprises DNA sequences SEQ ID NOs: 17, 19, 18 and 20. According to some embodiments, the DNA construct comprises SEQ ID NO: 27 or a variant thereof. According to another embodiment, the DNA construct comprises SEQ ID NO: 26 or a variant thereof. According to another embodiment, the DNA construct comprises from 5' to 3' SEQ ID NO: 27 and SEQ ID NO: 26. According to another embodiment, the DNA construct comprises from 5' to 3' SEQ ID NO: 27 and SEQ ID NO: 26.

According to one embodiment, a DNA construct encoding two CARs of the present invention has SEQ ID NO: 23. According to another embodiment, the DNA construct is a variant, e.g. a conservative variant, of SEQ ID NO: 23.

According to one embodiment, the method comprises transducing T cells with two DNA constructs each encoding one separate CAR of the present invention, wherein the first DNA construct comprises the DNA sequence SEQ ID NO: 27 and the second DNA construct comprises the DNA sequence SEQ ID NO: 26. According to one embodiment, the first DNA construct has a DNA sequence being a variant, such as conservative variant of SEQ ID NO: 27. According to one embodiment, the second DNA construct has a DNA sequence being a variant, such as conservative variant of SEQ ID NO: 26. According to a further embodiment, the T-cell comprising two DNA constructs, wherein the first DNA construct comprises the DNA being a variant of SEQ ID NO: 27 and the second DNA construct has a DNA sequence being a variant of SEQ ID NO: 26.

According to any one of the above embodiments, the transduction is performed using a viral vector selected from retroviral, adenoviral, lentiviral and adeno-associated viral vectors.

According to some embodiments, the vector may contain an optional marker suitable for use in the identification of transformed cells.

The terms "comprising", "comprise(s)", "include(s)", "having", "has" and "contain(s)," are used herein interchangeably and have the meaning of "consisting at least in part of". When interpreting each statement in this specification that includes the term "comprising", features other than that or those prefaced by the term may also be present. Related terms such as "comprise" and "comprises" are to be interpreted in the same manner. The terms "have", "has", having" and "comprising" may also encompass the meaning of "consisting of" and "consisting essentially of", and may be substituted by these terms. The term "consisting of" excludes any component, step or procedure not specifically delineated or listed. The term "consisting essentially of" means that the composition or component may include additional ingredients, but only if the additional ingredients do not materially alter the basic and novel characteristics of the claimed compositions or methods.

Having now generally described the invention, the same will be more readily understood through reference to the following examples, which are provided by way of illustration and are not intended to be limiting of the present invention.

EXAMPLES

Example 1

In the following example, human T cells, transduced with different chimeric antigen receptors were prepared and tested. The aim of present example was to test the efficacy of T-cells transduces with two different CARs specifically binding to two distinct antigens in treatments of ovarian cancer. For this purpose, 3 pairs of antigens were chosen: HER2 and CD138; CD138 and CD24; and HER2 and CD24. Several CARs aimed at specifically binding these antigens were generated. One CAR comprised scFv derived from anti-CD138-specific monoclonal antibody with $V_L$ and $V_H$ having the sequences SEQ ID NO: 1 and SEQ ID NO: 2, respectively. Another CARs comprised scFv derived from anti-HER2-specific monoclonal antibody with $V_L$ and $V_H$ having the sequences SEQ ID NO: 3 and SEQ ID NO: 4, respectively. Another type of CAR comprised scFv derived from anti-CD24 specific monoclonal antibody with $V_L$ and $V_H$ having the sequences SEQ ID NO: 5 and SEQ ID NO: 6. The $V_L$ and $V_H$ in each one of the anti-CD138 and anti-HER2 CARs were connected with 14 amino acid linker having the sequence GSTSGSGKSSEGKG (SEQ ID NO: [[1]]7). The $V_L$ and $V_H$ in each one of the anti-CD24 were connected with 14 amino acid linker having the sequence GSSSGSGKSSEGK (SEQ ID NO: 36).

Figure 1B:
Figure 1C:
Figure 2A:
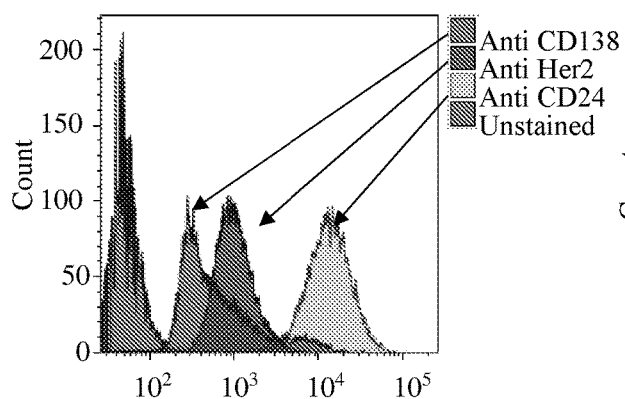
FIG. 2A—OVCAR8 cells.
Figure 2B:
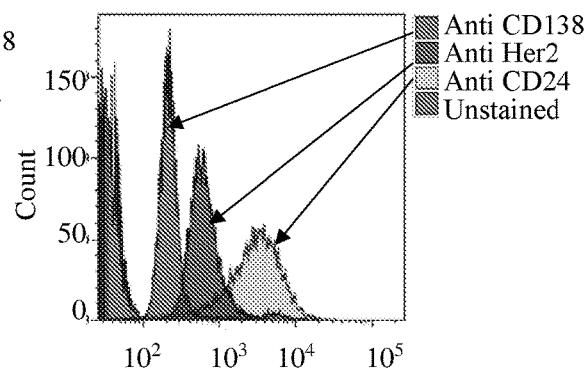
FIG. 2B—NAR cells.
Figure 2C:
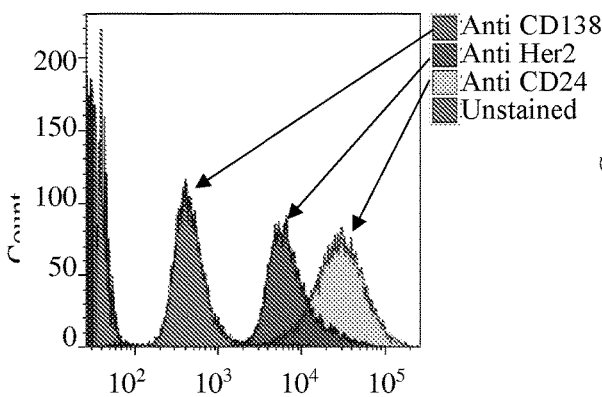
FIG. 2C—SKOV-3 cells, FIG. 2D—OVCAR423 cells and FIG. 2E—presence of CD38 antigen in NAR, OVCAR8 and skov cells (uns—unstained cells, is—isotype control; OVCAR8, NAR and SKOV are different types of ovarian cancer cells).
Figure 2D:
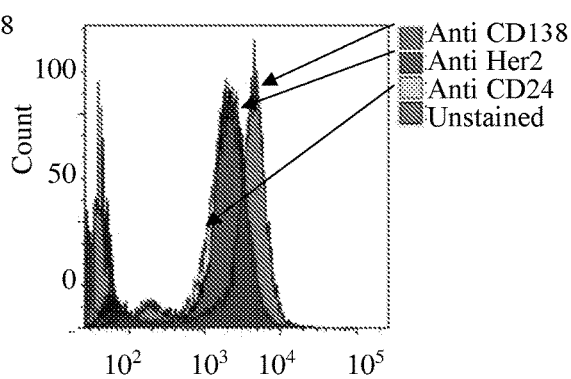
FIG. 2 shows FACS analyses of different ovarian cancer cells for presence of CD138, HER2, CD24 and CD38 antigens.
Figure 2E:
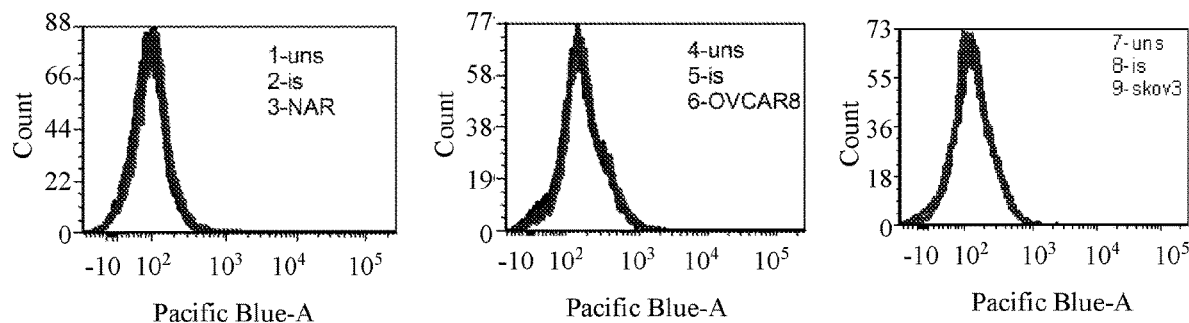

The test item of the present experiments were T-cells transduced with the following pairs of CARs: (i) CAR having anti-CD138 (αCD138) scFv and CAR having anti-HER2 (αHER2) scFv; (ii) CAR having αCD138 scFv and CAR having anti CD24 (αCD24) scFv; and (iii) CAR having αHER2 scFv and CAR having αCD24 scFv. In order to reduce "on target off tumor" toxicity, the costimulatory domain and activation domain were separated between the two CARs; one CAR harbored only a costimulatory domain (a transmembrane and co-stimulatory domain of CD28 have the sequence SEQ ID NO: 31 and SEQ ID NO: 9, respectively) and another CAR had the activation domain only (i.e. comprises the transmembrane domain of CD8 and FcR-gamma domain have the sequence SEQ ID NO: 32 and SEQ ID NO: 8, respectively). The two CARs were placed in one DNA construct comprising a self-cleaving peptide T2A, having the sequence SEQ ID NO: 14, between them. The schematic presentation of the prepared constructs is shown in FIG. 1, and the used constructs had the sequence SEQ ID NO: 21, 22 and 23. The constructs are referred as Dual-CAR 1, 2, and 3, respectively.

As a first step, 4 types of ovarian cancer cells: OVCAR8, NAR, SKOV-3 and OVCAR423 were tested for the presence of the 4 antigens: CD138, HER2b CD38 and CD24.

Flow Cytometry Analyses $10^6$ cells of ovarian cancer cells were stained with the following fluorescence-conjugated antibodies: anti-human HER2 APC (Cat:324408) anti-human CD138 APC (Cat:352307) anti-human CD24 PE (Cat:311106) all from biolegend, and anti-human CD38 eflour 450 (Cat:48-0388-42) from ebioscience. Cells were incubated with the antibodies for 30 min at 4° C. and washed with phosphate buffered saline (PBS) containing 2% fetal bovine serum (FBS) 0.05% sodium azide and 2 mM EDTA. Cells were analyzed on a FACS Canto II flow cytometer using FACSDiva (both from Becton Dickinson). Results were analyzed using FCS express 6 flow research (De Novo Software, Glendale, California)

As can be seen from FIG. 2, each one of the tested ovarian cancer cell types expressed all these antigens. On the contrary, none of these cells express CD38 (see FIG. 2). It can be seen in this figure that there is no shift between unstained and stained cells, indicating that the cell do not present CD38 on their surface).

Example 2

Figure 3:
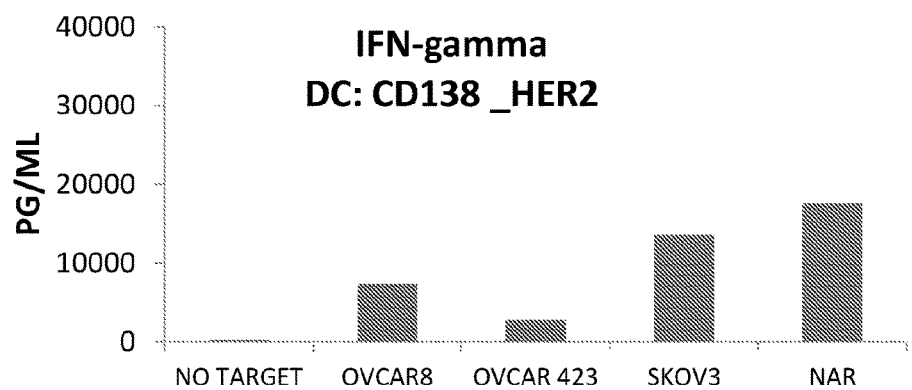
FIGS. 3-5 show the ability of T-cells transduced with different Dual CARs constructs to interact with different cell lines of ovarian cancer expressing different antigens, as tested by IFN-7 assay.
Figure 4:
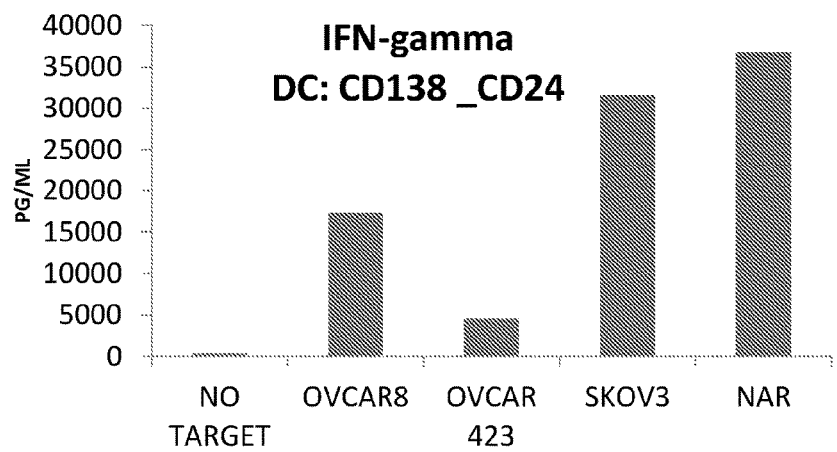
Figure 5:
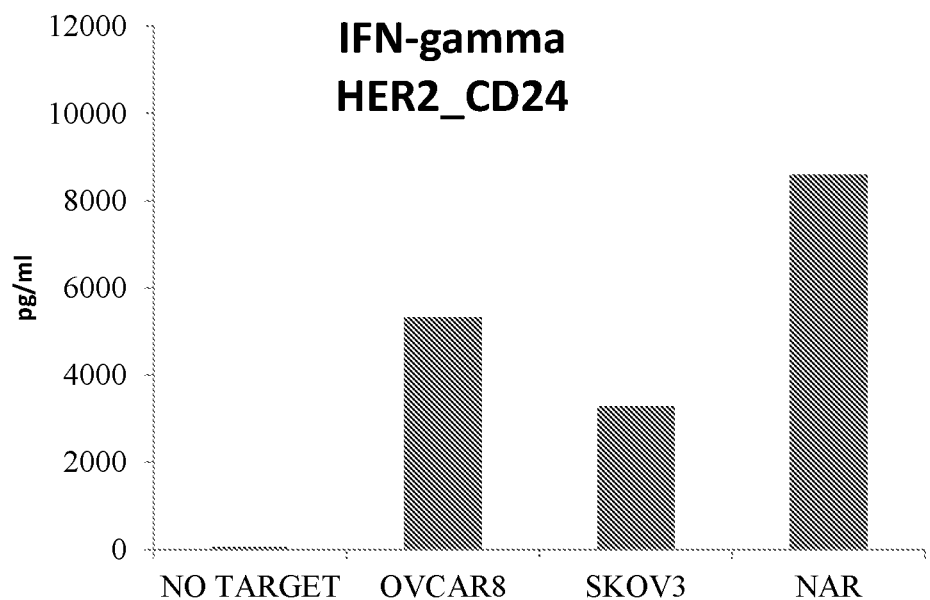

In this experiment, IFN-γ secretion by T-cells transduced with Dual-CARs 1, 2 and 3 upon incubation with different cell lines was measured and compared to the secretion without the target antigens. The cell lines were as defined in Example 1. The results are presented in FIGS. 3-5. In addition, the IFN-γ secretion by T-cells transduced with Dual-CARs 1, 2 and 3, or by T-cells transduces with only one CAR, either comprising anti-CD38 or comprising anti-CD138 scFv upon incubation with OVCAR-8 cells was tested.

IFN-γ Quantification

Target cells OVCAR8, NAR, SKOV-3 and OVCAR423 ($2.5 \times 10^4$ cells/well) were co-cultured with $5 \times 10^4$ trunsduced/untrunsduced lymphocytes. 24 h later supernatant was collected and secreted IFN-γ was analyzed by ELISA kit (R&D systems).

As shown in Example 1, OVCAR-8 ovarian cancer cells do not express CD38 antigen.

It can be seen from the results that all ovarian cancer cell types caused IFN-γ secretion by the T-cells induced with Dual CARs 1, 2 and 3. As shown in these figures, different cells caused to different level of secretion.

Figure 6:
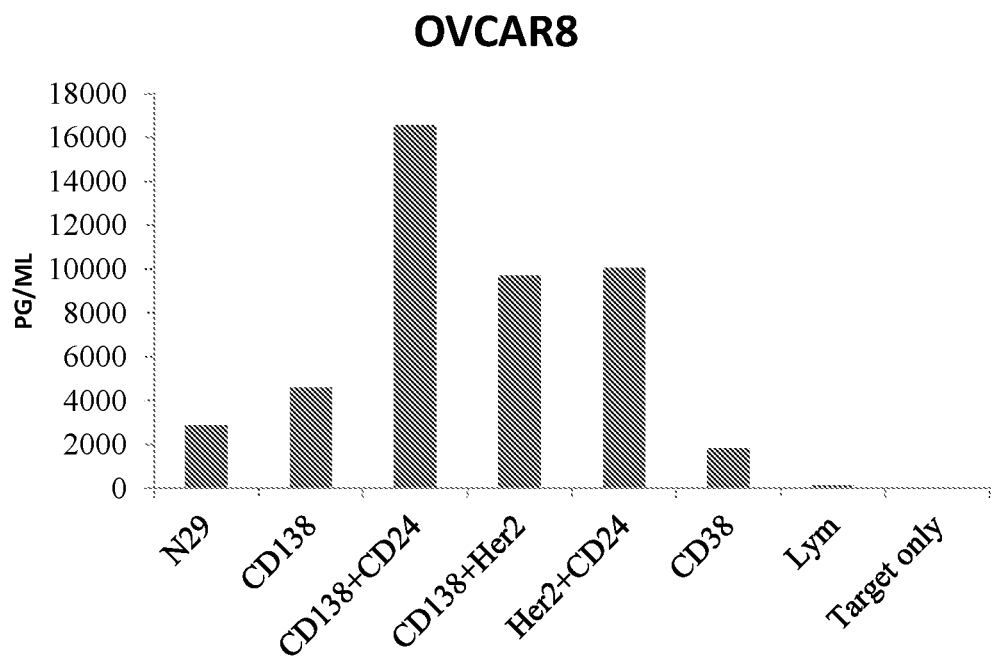
FIG. 6 shows the ability of T-cells transduced with different CARs to interact with OVAR8 ovarian cancer, as tested by IFN-7 assay.

It was also observed (FIG. 6) that all Dual CARs provided much higher IFN-γ secretion than CAR comprising only αCD138 or αCD38 scFv.

Example 3

In order to verify the killing activity of the double CAR combination towards ovarian cancer cells but its safety towards normal tissues, we focus on the stimulation of the various CARs against normal cells. The ability of T-cells transduced with double CAR or as control activated T cells/or nonspecific CARs to interact with primary cells (several normal tissues) or ovarian cancer cell line is tested by IFN-γ assay. It is expected that double CAR T-cells do not show activity towards normal cells, in accordance to the double CAR concept requiring two specific antigens in order the T-cell to be activated.

Although the present invention has been described herein above by way of preferred embodiments thereof, it can be modified, without departing from the spirit and nature of the subject invention as defined in the appended claims.

The invention claimed is:

1. A T-cell genetically modified to express at least two distinct and separate chimeric antigen receptors (CARs), wherein the antigen binding domain of one CAR is different from the antigen binding domain of another CAR, wherein one CAR comprises a costimulatory domain and is devoid of an activation domain and another CAR comprises an activation domain and is devoid of a costimulatory domain and wherein the antigen binding domain is selected from anti-CD138, anti-HER2 and anti-CD24 antigen binding domain, wherein the anti-CD138 antigen binding domain is a single chain variable fragment (anti-CD138 scFv) comprising $V_L$ and $V_H$ domains, wherein the $V_L$ domain comprises three complementarity determining regions (CDRs) of a $V_L$ having the amino acid sequence of SEQ ID NO:

1 and the V<sub>H</sub> domain comprises three CDRs of a V<sub>H</sub> having the amino acid sequence of SEQ ID NO: 2, the anti-HER2 antigen binding domain is a single chain variable fragment (anti-HER2 scFv) comprising V<sub>L</sub> and V<sub>H</sub> domains, wherein the V<sub>L</sub> domain comprises three CDRs of a V<sub>L</sub> having the amino acid sequence of SEQ ID NO: 3 and the V<sub>H</sub> domain comprises three CDRs of a V<sub>H</sub> having the amino acid sequence of SEQ ID NO: 4, and the anti-CD24 antigen binding domain is a single chain variable fragment (anti-CD24 scFv) comprising V<sub>L</sub> and V<sub>H</sub> domains, wherein the V<sub>L</sub> domain comprises three CDRs of a V<sub>L</sub> having the amino acid sequence of SEQ ID NO: 5 and the V<sub>H</sub> domain comprises three CDRs of a V<sub>H</sub> having the amino acid sequence of SEQ ID NO: 6.

2. The T-cell of claim 1, wherein the T-cell is genetically modified to express two distinct and separate CARs, wherein the two distinct and separate CARs are selected from the group consisting of:
(i) the first CAR comprises an antigen binding domain that binds specifically to CD138 and the second CAR comprises an antigen binding domain that binds specifically to HER2;
(ii) the first CAR comprises an antigen binding domain that binds specifically to CD138 and the second CAR comprises an antigen binding domain that binds specifically to CD24; and
(iii) the first CAR comprises an antigen binding domain that binds specifically to HER2 and the second CAR comprises an antigen binding domain that binds specifically to CD24.

3. The T-cell of claim 1, characterized by at least one of:
(i) the anti-CD138 scFv comprises a V<sub>L</sub> domain having the amino acid sequence of SEQ ID NO: 1 and a V<sub>H</sub> domain having the amino acid sequence of SEQ ID NO: 2, wherein the V<sub>L</sub> and the V<sub>H</sub> domains of the anti-CD138 scFv are bound by a peptide linker;
(ii) the anti-HER2 scFv comprises a V<sub>L</sub> domain having the amino acid sequence of SEQ ID NO: 3 and a V<sub>H</sub> domain having the amino acid sequence of SEQ ID NO: 4, wherein the V<sub>L</sub> and the V<sub>H</sub> domains of the anti-HER2 scFv are bound by a peptide linker; and
(iii) the anti-CD24 scFv comprises a V<sub>L</sub> domain having the amino acid sequence of SEQ ID NO: 5 and a V<sub>H</sub> domain having the amino acid sequence of SEQ ID NO: 6, wherein the V<sub>L</sub> and the V<sub>H</sub> domains of the anti-CD24 scFv are bound by a peptide linker.

4. The T-cell according to claim 3, wherein the peptide linker is a peptide having an amino acid sequence selected from SEQ ID NO: 7 or SEQ ID NO: 36.

5. The T-cell of claim 1, wherein the costimulatory domain is selected from a costimulatory domain of CD28, 4-1BB, OX40, ICOS, CD27, CD80, or CD70 and the activation domain is selected from an FcRγ or CD3-ζ activation domain.

6. The T-cell of claim 1, wherein the activation domain is FcRγ activation domain having the amino acid sequence of SEQ ID NO: 8 and the costimulatory domain is a costimulatory domain of CD28 having the amino acid sequence of SEQ ID NO: 9.

7. The T-cell of claim 1, wherein the T-cell is engineered to express two CARs, wherein the two CARs are selected from the group consisting of:
(i) the first CAR has amino acid sequence SEQ ID NO: 10, and the second CAR has amino acid sequence SEQ ID NO: 11;
(ii) the first CAR has amino acid sequence SEQ ID NO: 10, and the second CAR has amino acid sequence SEQ ID NO: 12; and
(iii) the first CAR has amino acid sequence SEQ ID NO: 13, and the second CAR has amino acid sequence SEQ ID NO: 12.

8. The T-cell of claim 1, comprising at least one copy of one or more DNA constructs encoding the at least two distinct and separate chimeric antigen receptors (CARs), wherein the antigen binding domain of one CAR is different from the antigen binding domain of another CAR and wherein the antigen binding domain is selected from anti-CD138, anti-HER2 and anti-CD24 antigen binding domain.

9. The T-cell of claim 8, comprising either:
(I) at least one copy of a DNA construct selected from the group consisting of:
(a) a DNA construct encoding for: (A) from 5' to 3': (i) a leader peptide, (ii) anti-CD138 scFv, (iii) a transmembrane domain I, (iv) a costimulatory domain or an activation domain; and (B) from 5' to 3': (v) a leader peptide, (vi) anti-HER2 scFv, (vii) a transmembrane domain II, and (viii) an activation domain or a costimulatory domain; wherein (A) and (B) are separated by a self-cleaving peptide;
(b) a DNA construct encoding for, from 5' to 3', (i) a leader peptide, (ii) anti-CD138 scFv, (iii) a transmembrane domain I, (iv) a costimulatory domain, (v) a self-cleaving peptide, (vi) a leader peptide, (vii) anti-HER2 scFv, (viii) a transmembrane domain II, and (ix) an activation domain;
(c) a DNA construct encoding for, from 5' to 3', (i) a leader peptide, (ii) anti-HER2 scFv, (iii) transmembrane domain II (iv) an activation domain, (v) a self-cleaving peptide, (vi) a leader peptide, (vii) anti-CD138 scFv, (viii) a transmembrane domain I, and (ix) a costimulatory domain;
(d) a DNA construct encoding for: (A) from 5' to 3': (i) a leader peptide, (ii) anti-CD138 scFv, (iii) transmembrane domain I, and (iv) a costimulatory domain or an activation domain; and (B) from 5' to 3': (v) a leader peptide, (vi) anti-CD24 scFv, (vii) transmembrane domain II and (viii) an activation domain or a costimulatory domain, wherein (A) and (B) are separated by a self-cleaving peptide;
(e) a DNA construct encoding for, from 5' to 3', (i) a leader peptide, (ii) anti-CD24 scFv, (iii) transmembrane domain II (iv) an activation domain, (v) a self-cleaving peptide, (vi) a leader peptide, (vii) anti-CD138 scFv, (viii) transmembrane domain I, and (ix) a costimulatory domain;
(f) a DNA construct encoding for, from 5' to 3', (i) a leader peptide, (ii) anti-CD138 scFv, (iii) transmembrane domain I, (iv) a costimulatory domain, (v) a self-cleaving peptide, (vi) a leader peptide, (vii) anti-CD24 scFv, (viii) transmembrane domain II and (ix) an activation domain;
(g) a DNA construct encoding for: (A) from 5' to 3': (i) a leader peptide, (ii) anti-HER2 scFv, (iii) transmembrane domain I, and (iv) a costimulatory domain or an activation domain; and (B) from 5' to 3': (v) a leader peptide, (vi) anti-CD24 scFv, (vii) transmembrane domain II and (viii) an activation domain or a costimulatory domain; wherein (A) and (B) are separated by a self-cleaving peptide;
(h) a DNA construct encoding for, from 5' to 3', (i) a leader peptide, (ii) anti-HER2 scFv, (iii) transmembrane domain I, (iv) a costimulatory domain, (v) a self-cleaving peptide, (vi) a leader peptide, (vii) anti-CD24 scFv, (viii) transmembrane domain II and (ix) an activation domain;
(i) a DNA construct encoding for, from 5' to 3', (i) a leader peptide, (ii) anti-CD24 scFv, (iii) transmembrane domain II (iv) an activation domain, (v) a self-cleaving peptide, (vi) a leader peptide, (vii) anti-HER2 scFv, (viii) transmembrane domain I and (ix) a costimulatory domain, and
(j) a DNA construct comprising a DNA sequence selected from SEQ ID NO: 21, 22, 23 or a variant thereof, or
(II) two different DNA constructs, wherein the two different DNA constructs are selected from the group consisting of:
(k) the first DNA construct comprises a sequence encoding, from 5' to 3' (i) a leader peptide, (ii) anti-CD138 scFv, (iii) transmembrane domain I and (iv) a costimulatory domain or an activation domain, and the second DNA construct comprises a sequence encoding from 5' to 3' (i) a leader peptide, (ii) anti-HER2 scFv, (iii) transmembrane domain II and (iv) an activation domain or a costimulatory domain;
(l) the first DNA construct comprises a sequence encoding, from 5' to 3' (i) a leader peptide, (ii) anti-CD138 scFv, (iii) transmembrane domain I and (iv) a costimulatory domain or an activation domain, and the second DNA construct comprises a sequence encoding from 5' to 3' (i) a leader peptide, (ii) anti-CD24 scFv, (iii) transmembrane domain II and (iv) an activation domain or a costimulatory domain;
(m) the first DNA construct comprises a sequence encoding, from 5' to 3' (i) a leader peptide, (ii) anti-HER2 scFv, (iii) transmembrane domain I and (iv) a costimulatory domain or an activation domain, and the second DNA construct comprises a sequence encoding from 5' to 3' (i) a leader peptide, (ii) anti-CD24 scFv, (iii) transmembrane domain II and (iv) a costimulatory domain or an activation domain;
(n) the first DNA construct comprises the DNA sequence of SEQ ID NO: 24 or a conservative variant thereof encoding the amino acid sequence SEQ ID NO: 10 and the second DNA construct comprises the DNA sequence of SEQ ID NO: 25 or a variant thereof encoding the amino acid sequence SEQ ID NO: 11;
(o) the first DNA construct comprises the DNA sequence of SEQ ID NO: 24 or a conservative variant thereof encoding the amino acid sequence SEQ ID NO: 10 and the second DNA construct comprises the DNA sequence of SEQ ID NO: 26 or a variant thereof encoding the amino acid sequence SEQ ID NO: 12; and
(p) the first DNA construct comprises the DNA sequence of SEQ ID NO: 27 or a conservative variant thereof encoding the amino acid sequence SEQ ID NO: 13 and the second DNA construct comprises the DNA sequence of SEQ ID NO: 25 or a variant thereof encoding the amino acid sequence SEQ ID NO: 12.
10. The T-cell of claim 9, characterized by at least one of:
(i) the anti-CD138 scFv is encoded by the DNA sequence of SEQ ID NO: 16 or a conservative variant thereof;
(ii) the anti-HER2 scFv is encoded by the DNA sequence of SEQ ID NO: 17 or a conservative variant thereof;
(iv) the anti-CD24 scFv is encoded by the DNA sequence of SEQ ID NO: 18 or a conservative variant thereof;
(v) the costimulatory domain is encoded by the DNA sequence of SEQ ID NO: 19, or a variant thereof;
(vi) the activation domain is encoded by the DNA sequence of SEQ ID NO: 20, or a variant thereof; and (vii) the self-cleaving peptide is selected from a peptide having the amino acid sequence of SEQ ID NO: 14, and IRES peptide or encoded by the DNA sequence of SEQ ID NO: 15 or a variant thereof,
wherein the variant comprises at least 90% sequence identity to the original sequence.
11. The T-cell of claim 1, wherein the T cell is selected from a CD4+ T-cell or CD8+ T-cell.
12. A DNA construct selected from the group consisting of:
(a) A DNA construct encoding for: (A) from 5' to 3': (i) a leader peptide, (ii) an antigen binding domain selected from anti-CD138, anti-HER2 and anti-CD24, (iii) transmembrane domain I, and (iv) a costimulatory domain or an activation domain; and (B) from 5' to 3' (v) a leader peptide, (vi) an antigen binding domain selected from anti-CD138, anti-HER2 and anti-CD24, (vii) transmembrane domain II and (viii) an activation domain or a costimulatory domain; wherein (A) and (B) are separated by a self-cleaving peptide, and wherein the an antigen binding domains of (ii) and of (vi) are different;
(b) a DNA construct encoding for: (A) from 5' to 3': (i) a leader peptide, (ii) anti-CD138 scFv, (iii) transmembrane domain I, and (iv) a costimulatory domain or an activation domain; and (B) from 5' to 3' (v) a leader peptide, (vi) anti-HER2 scFv, (vii) transmembrane domain II and (viii) an activation domain or a costimulatory domain; wherein (A) and (B) are separated by a self-cleaving peptide;
(c) a DNA construct encoding for, from 5' to 3', (i) a leader peptide, (ii) anti-CD138 scFv, (iii) transmembrane domain I, (iv) a costimulatory domain, (v) a self-cleaving peptide, (vi) a leader peptide, (vii) anti-HER2 scFv, (viii) transmembrane domain II, and (ix) an activation domain;
(d) a DNA construct encoding for, from 5' to 3', (i) a leader peptide, (ii) anti-HER2 scFv, (iii) transmembrane domain II (iv) an activation domain, (v) a self-cleaving peptide, (vi) a leader peptide, (vii) anti-CD138 scFv, (viii) transmembrane domain I, and (ix) a costimulatory domain;
(e) a DNA construct encoding for, from 5' to 3', (A) from 5' to 3': (i) a leader peptide, (ii) anti-CD138 scFv, (iii) transmembrane domain I, and (iv) a costimulatory domain or an activation domain; and (B) from 5' to 3': (v) a leader peptide, (vi) anti-CD24 scFv, (vii) transmembrane domain II and (viii) an activation domain or a costimulatory domain, wherein (A) and (B) are separated by a self-cleaving peptide;
(f) a DNA construct encoding for, from 5' to 3', (i) a leader peptide, (ii) anti-CD138 scFv, (iii) transmembrane domain I, (iv) a costimulatory domain, (v) a self-cleaving peptide, (vi) a leader peptide, (vii) anti-CD24 scFv, (viii) transmembrane domain II, and (ix) an activation domain;
(g) a DNA construct encoding for, from 5' to 3', (i) a leader peptide, (ii) anti-CD24 scFv, (iii) transmembrane domain II (iv) an activation domain, (v) a self-cleaving peptide, (vi) a leader peptide, (vii) anti-CD138 scFv, (viii) transmembrane domain I, and (ix) a costimulatory domain;
(h) a DNA construct encoding for: (A) from 5' to 3': (i) a leader peptide, (ii) anti-HER2 scFv, (iii) transmembrane domain I, and (iv) a costimulatory domain or an activation domain; and (B) from 5' to 3': (v) a leader peptide, (vi) anti-CD24 scFv, (vii) transmembrane domain II and (viii) an activation domain or a costimulatory domain; wherein (A) and (B) are separated by a self-cleaving peptide;

(i) a DNA construct encoding for, from 5' to 3': (i) a leader peptide, (ii) anti-HER2 scFv, (iii) transmembrane domain I, (iv) a costimulatory domain, (v) a self-cleaving peptide, (vi) a leader peptide, (vii) anti-CD24 scFv, (viii) transmembrane domain II, and (ix) an activation domain; and (j) a DNA construct encoding for, from 5' to 3': (i) a leader peptide, (ii) anti-CD24 scFv, (iii) transmembrane domain II (iv) an activation domain, (v) a self-cleaving peptide, (vi) a leader peptide, (vii) anti-HER2 scFv, (viii) transmembrane domain I and (ix) a costimulatory domain, wherein one CAR comprises a costimulatory domain and is devoid of an activation domain and another CAR comprises an activation domain and is devoid of a costimulatory domain, wherein the anti-CD138 antigen binding domain is a single chain variable fragment (anti-CD138 scFv) comprising $V_L$ and $V_H$ domains, wherein the $V_L$ domain comprises three complementarity determining regions (CDRs) of a $V_L$ having the amino acid sequence of SEQ ID NO: 1 and the $V_H$ domain comprises three CDRs of a $V_H$ having the amino acid sequence of SEQ ID NO: 2, the antigen anti-HER2 binding domain is a single chain variable fragment (anti-HER2 scFv) comprising a $V_L$ and $V_H$ domains, wherein the $V_L$ domain comprises three CDRs of a $V_L$ having the amino acid sequence of SEQ ID NO: 3 and the $V_H$ domain comprises three CDRs of a $V_H$ having the amino acid sequence of SEQ ID NO: 4, and the antigen anti-CD24 binding domain is a single chain variable fragment (anti-CD24 scFv) comprising $V_L$ and $V_H$ domains, wherein the $V_L$ domain comprises three CDRs of a $V_L$ having the amino acid sequence of SEQ ID NO: 5 and the $V_H$ domain comprises three CDRs of a $V_H$ having the amino acid sequence of SEQ ID NO: 6.

13. The DNA construct of claim 12, characterized by at least one of:
   (i) the anti-CD138 scFv is encoded by the DNA sequence of SEQ ID NO: 16 or a conservative variant thereof;
   (ii) the anti-HER2 scFv is encoded by the DNA sequence of SEQ ID NO: 17 or a conservative variant thereof;
   (iii) the anti-CD24 scFv is encoded by the DNA sequence of SEQ ID NO: 18 or a conservative variant thereof;
   (iv) the costimulatory domain is encoded by the DNA sequence of SEQ ID NO: 19, or a variant thereof;
   (v) the activation domain is encoded by the DNA sequence of SEQ ID NO: 20, or a variant thereof;
   (vi) the transmembrane domain I is encoded by a the DNA sequence of SEQ ID NO: 34, or a variant thereof, the transmembrane domain II is encoded by the DNA sequence of SEQ ID NO: 35, or a variant thereof,
   (viii) the self-cleaving peptide is selected from the peptide having the amino acid sequence of SEQ ID NO: 14, and IRES peptide;
   (ix) the self-cleaving peptide is encoded by the DNA sequence of SEQ ID NO: 15 or a variant thereof; and
   (x) the DNA construct comprises a DNA sequence selected from SEQ ID NO: 21, 22, 23 or a conservative variant thereof,
   wherein the variant comprises at least 90% sequence identity to the original sequence.

14. A cell comprising the DNA construct according to claim 12.

15. A pharmaceutical composition comprising a plurality of T-cells according to claim 1, and a pharmaceutically acceptable carrier.

16. A method of treating cancer in a subject in need thereof, comprising administering an effective amount of T-cells according to claim 1 to the subject.

17. The method of claim 16, wherein the cancer is ovarian cancer.

18. A method for preparation of T-cells genetically modified to express at least two distinct and separate chimeric antigen receptors (CARs) comprising transfecting T-cells with the DNA construct according to claim 12, wherein the antigen binding domains of said distinct CAR are different from each other, and the antigen binding domain is selected from anti-CD138, anti-HER2 and anti-CD24 antigen binding domain.

* * * * *

SEQUENCE LISTING

<160> NUMBER OF SEQ ID NOS: 37

<210> SEQ ID NO 1
<211> LENGTH: 107
<212> TYPE: PRT
<213> ORGANISM: Artificial Sequence
<220> FEATURE:
<223> OTHER INFORMATION: Synthesized

<400> SEQUENCE: 1

```
Asp Ile Gln Met Thr Gln Ser Thr Ser Ser Leu Ser Ala Ser Leu Gly
1               5                   10                  15

Asp Arg Val Thr Ile Ser Cys Ser Ala Ser Gln Gly Ile Asn Asn Tyr
            20                  25                  30

Leu Asn Trp Tyr Gln Gln Lys Pro Asp Gly Thr Val Glu Leu Leu Ile
        35                  40                  45

Tyr Tyr Thr Ser Thr Leu Gln Ser Gly Val Pro Ser Arg Phe Ser Gly
    50                  55                  60

Ser Gly Ser Gly Thr Asp Tyr Ser Leu Thr Ile Ser Asn Leu Glu Pro
65                  70                  75                  80

Glu Asp Ile Gly Thr Tyr Tyr Cys Gln Gln Tyr Ser Lys Leu Pro Arg
                85                  90                  95

Thr Phe Gly Gly Gly Thr Lys Leu Glu Ile Lys
            100                 105

<210> SEQ ID NO 2
<211> LENGTH: 122
<212> TYPE: PRT
<213> ORGANISM: Artificial Sequence
<220> FEATURE:
<223> OTHER INFORMATION: Synthesized

<400> SEQUENCE: 2

Gln Val Gln Leu Gln Gln Ser Gly Ser Glu Leu Met Met Pro Gly Ala
1               5                   10                  15

Ser Val Lys Ile Ser Cys Lys Ala Thr Gly Tyr Thr Phe Ser Asn Tyr
            20                  25                  30

Trp Ile Glu Trp Val Lys Gln Arg Pro Gly His Gly Leu Glu Trp Ile
        35                  40                  45

Gly Glu Ile Leu Pro Gly Thr Gly Arg Thr Ile Tyr Asn Glu Lys Phe
    50                  55                  60

Lys Gly Lys Ala Thr Phe Thr Ala Asp Ile Ser Ser Asn Thr Val Gln
65                  70                  75                  80

Met Gln Leu Ser Ser Leu Thr Ser Glu Asp Ser Ala Val Tyr Tyr Cys
                85                  90                  95

Ala Arg Arg Asp Tyr Tyr Gly Asn Phe Tyr Tyr Ala Met Asp Tyr Trp
            100                 105                 110

Gly Gln Gly Thr Ser Val Thr Val Ser Ser
        115                 120

<210> SEQ ID NO 3
<211> LENGTH: 105
<212> TYPE: PRT
<213> ORGANISM: Artificial Sequence
<220> FEATURE:
<223> OTHER INFORMATION: Synthesized

<400> SEQUENCE: 3

Val Met Thr Gln Ser Pro Lys Phe Met Ser Thr Ser Val Gly Asp Arg
1               5                   10                  15

Ile Ser Val Thr Cys Lys Ala Ser Gln Asp Val Gly Pro Asn Val Ala
            20                  25                  30

Trp Tyr Gln Gln Lys Pro Gly Gln Ser Pro Lys Pro Leu Ile Tyr Ser
        35                  40                  45

Ala Ser Tyr Leu Tyr Asn Gly Val Pro Asp Arg Phe Thr Gly Ser Gly
    50                  55                  60

Ser Gly Thr Asp Phe Ser Leu Thr Ile Ser Asn Val Gln Ser Asp Asp
```

```
                65                  70                  75                  80
Leu Ala Glu Tyr Phe Cys Gln Gln Tyr Asn Thr Tyr Pro Phe Thr Phe
                    85                  90                  95

Gly Gly Gly Thr Lys Leu Glu Ile Lys
            100                 105

<210> SEQ ID NO 4
<211> LENGTH: 123
<212> TYPE: PRT
<213> ORGANISM: Artificial Sequence
<220> FEATURE:
<223> OTHER INFORMATION: Synthesized

<400> SEQUENCE: 4

Glu Val Gln Leu Glu Glu Ser Gly Gly Gly Leu Val Gln Pro Lys Gly
1               5                   10                  15

Ser Leu Lys Leu Ser Cys Ala Ala Ser Gly Phe Thr Phe Asn Thr Tyr
                20                  25                  30

Ala Met Asn Trp Val Arg Gln Ala Pro Gly Lys Gly Leu Glu Trp Ile
            35                  40                  45

Val Arg Ile Arg Ser Lys Ser Asn Asn Tyr Ala Thr Tyr Tyr Val Asp
        50                  55                  60

Ser Val Lys Asp Arg Phe Thr Ile Ser Arg Asp Asp Ser Gln Ser Met
65                  70                  75                  80

Leu Tyr Leu Gln Met Asn Asn Leu Lys Thr Glu Asp Thr Ala Met Tyr
                85                  90                  95

Tyr Cys Val Thr Ser Tyr Asp Tyr Asp Lys Val Leu Phe Ala Tyr
            100                 105                 110

Trp Gly Gln Gly Thr Thr Val Thr Val Lys Gly
        115                 120

<210> SEQ ID NO 5
<211> LENGTH: 113
<212> TYPE: PRT
<213> ORGANISM: Artificial Sequence
<220> FEATURE:
<223> OTHER INFORMATION: Synthesized

<400> SEQUENCE: 5

Asp Ile Val Met Thr Gln Thr Pro Ser Ser Leu Asn Val Ser Val Gly
1               5                   10                  15

Glu Lys Val Thr Met Arg Cys Arg Ser Ser Gln Ser Leu Leu Tyr Ser
                20                  25                  30

Ser Asp Gln Lys Asn Tyr Leu Thr Trp Tyr Gln Gln Lys Pro Gly Gln
            35                  40                  45

Ser Pro Lys Leu Leu Ile Ser Trp Ala Ser Thr Arg Ala Ser Gly Val
        50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Gly Val Tyr Tyr Cys Gln Gln
                85                  90                  95

Tyr Phe Ile Tyr Pro Leu Thr Phe Gly Val Gly Thr Lys Leu Gly Leu
            100                 105                 110

Lys

<210> SEQ ID NO 6
<211> LENGTH: 117
<212> TYPE: PRT
```

```
<213> ORGANISM: Artificial Sequence
<220> FEATURE:
<223> OTHER INFORMATION: Synthesized

<400> SEQUENCE: 6

Glu Val Lys Leu Glu Glu Ser Gly Pro Asp Leu Val Lys Pro Ser Gln
1               5                   10                  15

Ser Leu Ser Leu Thr Cys Thr Val Thr Gly Tyr Ser Ile Thr Ser Gly
            20                  25                  30

Tyr Thr Trp His Trp Ile Arg Gln Phe Pro Gly Asn Thr Val Glu Trp
        35                  40                  45

Met Gly Tyr Ile Gln Tyr Thr Gly Ser Thr Arg Tyr Asn Pro Ala Leu
50                  55                  60

Arg Gly Arg Leu Ser Ile Ser Arg Asp Thr Ser Lys Asn Gln Phe Phe
65                  70                  75                  80

Leu Gln Leu Ile Ser Val Thr Ala Asp Thr Gly Thr Tyr Phe Cys
                85                  90                  95

Ala Arg Gly Thr Thr Ala Ser Phe Asp Tyr Trp Gly Gln Gly Thr Thr
                100                 105                 110

Leu Thr Val Ala Ser
        115

<210> SEQ ID NO 7
<211> LENGTH: 14
<212> TYPE: PRT
<213> ORGANISM: Artificial Sequence
<220> FEATURE:
<223> OTHER INFORMATION: Synthesized

<400> SEQUENCE: 7

Gly Ser Thr Ser Gly Ser Gly Lys Ser Ser Glu Gly Lys Gly
1               5                   10

<210> SEQ ID NO 8
<211> LENGTH: 40
<212> TYPE: PRT
<213> ORGANISM: Artificial Sequence
<220> FEATURE:
<223> OTHER INFORMATION: Synthesized

<400> SEQUENCE: 8

Arg Ser Gln Val Arg Lys Ala Ala Ile Thr Ser Tyr Glu Lys Ser Asp
1               5                   10                  15

Gly Val Tyr Thr Gly Leu Ser Thr Arg Asn Gln Glu Thr Tyr Glu Thr
            20                  25                  30

Leu Lys His Glu Lys Pro Pro Gln
        35                  40

<210> SEQ ID NO 9
<211> LENGTH: 40
<212> TYPE: PRT
<213> ORGANISM: Artificial Sequence
<220> FEATURE:
<223> OTHER INFORMATION: Synthesized

<400> SEQUENCE: 9

Ser Lys Arg Ser Arg Leu Leu His Ser Asp Tyr Met Asn Met Thr Pro
1               5                   10                  15

Arg Arg Pro Gly Pro Thr Arg Lys His Tyr Gln Pro Tyr Ala Pro Pro
            20                  25                  30

Arg Asp Phe Ala Ala Tyr Arg Ser
```

35                  40

<210> SEQ ID NO 10
<211> LENGTH: 353
<212> TYPE: PRT
<213> ORGANISM: Artificial Sequence
<220> FEATURE:
<223> OTHER INFORMATION: Synthesized

<400> SEQUENCE: 10

Met Asp Phe Gln Val Gln Ile Phe Ser Phe Leu Leu Ile Ser Ala Ser
1               5                   10                  15

Val Ile Met Ser Arg Gly Asp Ile Gln Met Thr Gln Ser Thr Ser Ser
            20                  25                  30

Leu Ser Ala Ser Leu Gly Asp Arg Val Thr Ile Ser Cys Ser Ala Ser
        35                  40                  45

Gln Gly Ile Asn Asn Tyr Leu Asn Trp Tyr Gln Gln Lys Pro Asp Gly
    50                  55                  60

Thr Val Glu Leu Leu Ile Tyr Tyr Thr Ser Thr Leu Gln Ser Gly Val
65                  70                  75                  80

Pro Ser Arg Phe Ser Gly Ser Gly Ser Gly Thr Asp Tyr Ser Leu Thr
                85                  90                  95

Ile Ser Asn Leu Glu Pro Glu Asp Ile Gly Thr Tyr Tyr Cys Gln Gln
            100                 105                 110

Tyr Ser Lys Leu Pro Arg Thr Phe Gly Gly Gly Thr Lys Leu Glu Ile
        115                 120                 125

Lys Gly Ser Thr Ser Gly Ser Gly Lys Ser Ser Glu Gly Lys Gly Gln
    130                 135                 140

Val Gln Leu Gln Gln Ser Gly Ser Glu Leu Met Met Pro Gly Ala Ser
145                 150                 155                 160

Val Lys Ile Ser Cys Lys Ala Thr Gly Tyr Thr Phe Ser Asn Tyr Trp
                165                 170                 175

Ile Glu Trp Val Lys Gln Arg Pro Gly His Gly Leu Glu Trp Ile Gly
            180                 185                 190

Glu Ile Leu Pro Gly Thr Gly Arg Thr Ile Tyr Asn Glu Lys Phe Lys
        195                 200                 205

Gly Lys Ala Thr Phe Thr Ala Asp Ile Ser Ser Asn Thr Val Gln Met
    210                 215                 220

Gln Leu Ser Ser Leu Thr Ser Glu Asp Ser Ala Val Tyr Tyr Cys Ala
225                 230                 235                 240

Arg Arg Asp Tyr Tyr Gly Asn Phe Tyr Tyr Ala Met Asp Tyr Trp Gly
                245                 250                 255

Gln Gly Thr Ser Val Thr Val Ser Ser Ala Ala Ala Lys Gly Lys His
            260                 265                 270

Leu Cys Pro Ser Pro Leu Phe Pro Gly Pro Ser Lys Pro Phe Trp Val
        275                 280                 285

Leu Val Val Val Gly Gly Val Leu Ala Cys Tyr Ser Leu Leu Val Thr
    290                 295                 300

Val Ala Phe Ile Ile Phe Trp Val Arg Ser Lys Arg Ser Arg Leu Leu
305                 310                 315                 320

His Ser Asp Tyr Met Asn Met Thr Pro Arg Arg Pro Gly Pro Thr Arg
                325                 330                 335

Lys His Tyr Gln Pro Tyr Ala Pro Pro Arg Asp Phe Ala Ala Tyr Arg
            340                 345                 350

Ser

<210> SEQ ID NO 11
<211> LENGTH: 397
<212> TYPE: PRT
<213> ORGANISM: Artificial Sequence
<220> FEATURE:
<223> OTHER INFORMATION: artificial sequence

<400> SEQUENCE: 11

```
Met Asp Phe Gln Val Gln Ile Phe Ser Phe Leu Leu Ile Ser Ala Ser
1               5                   10                  15

Val Ile Met Ser Arg Gly Asp Ile Val Met Thr Gln Ser Pro Lys Phe
            20                  25                  30

Met Ser Thr Ser Val Gly Asp Arg Ile Ser Val Thr Cys Lys Ala Ser
        35                  40                  45

Gln Asp Val Gly Pro Asn Val Ala Trp Tyr Gln Lys Pro Gly Gln
    50                  55                  60

Ser Pro Lys Pro Leu Ile Tyr Ser Ala Ser Tyr Leu Tyr Asn Gly Val
65                  70                  75                  80

Pro Asp Arg Phe Thr Gly Ser Gly Ser Gly Thr Asp Phe Ser Leu Thr
                85                  90                  95

Ile Ser Asn Val Gln Ser Asp Asp Leu Ala Glu Tyr Phe Cys Gln Gln
            100                 105                 110

Tyr Asn Thr Tyr Pro Phe Thr Phe Gly Gly Gly Thr Lys Leu Glu Ile
        115                 120                 125

Lys Gly Ser Thr Ser Gly Ser Gly Lys Ser Ser Glu Gly Lys Gly Glu
    130                 135                 140

Val Gln Leu Glu Glu Ser Gly Gly Gly Leu Val Gln Pro Lys Gly Ser
145                 150                 155                 160

Leu Lys Leu Ser Cys Ala Ala Ser Gly Phe Thr Phe Asn Thr Tyr Ala
                165                 170                 175

Met Asn Trp Val Arg Gln Ala Pro Gly Lys Gly Leu Glu Trp Ile Val
            180                 185                 190

Arg Ile Arg Ser Lys Ser Asn Asn Tyr Ala Thr Tyr Tyr Val Asp Ser
        195                 200                 205

Val Lys Asp Arg Phe Thr Ile Ser Arg Asp Asp Ser Gln Ser Met Leu
    210                 215                 220

Tyr Leu Gln Met Asn Asn Leu Lys Thr Glu Asp Thr Ala Met Tyr Tyr
225                 230                 235                 240

Cys Val Thr Ser Tyr Tyr Asp Tyr Asp Lys Val Leu Phe Ala Tyr Trp
                245                 250                 255

Gly Gln Gly Thr Thr Val Thr Val Lys Gly Leu Ser Asn Ser Ile Met
            260                 265                 270

Tyr Phe Ser His Phe Val Pro Val Phe Leu Pro Ala Lys Pro Thr Thr
        275                 280                 285

Thr Pro Ala Pro Arg Pro Pro Thr Pro Ala Pro Thr Ile Ala Ser Gln
    290                 295                 300

Pro Leu Ser Leu Arg Pro Glu Ala Cys Arg Pro Ala Ala Gly Gly Ala
305                 310                 315                 320

Val His Thr Arg Gly Leu Asp Phe Ala Cys Asp Ile Tyr Ile Trp Ala
                325                 330                 335

Pro Leu Ala Gly Thr Cys Gly Val Leu Leu Leu Ser Leu Val Ile Thr
            340                 345                 350

Leu Tyr Cys Asn His Arg Ser Gln Val Arg Lys Ala Ala Ile Thr Ser
        355                 360                 365
```

Tyr Glu Lys Ser Asp Gly Val Tyr Thr Gly Leu Ser Thr Arg Asn Gln
        370                 375                 380

Glu Thr Tyr Glu Thr Leu Lys His Glu Lys Pro Pro Gln
385                 390                 395

<210> SEQ ID NO 12
<211> LENGTH: 397
<212> TYPE: PRT
<213> ORGANISM: Artificial Sequence
<220> FEATURE:
<223> OTHER INFORMATION: Synthesized

<400> SEQUENCE: 12

Met Asp Phe Gln Val Gln Ile Phe Ser Phe Leu Leu Ile Ser Ala Ser
1               5                   10                  15

Val Ile Met Ser Arg Gly Asp Ile Val Met Thr Gln Thr Pro Ser Ser
                20                  25                  30

Leu Asn Val Ser Val Gly Glu Lys Val Thr Met Arg Cys Arg Ser Ser
            35                  40                  45

Gln Ser Leu Leu Tyr Ser Ser Asp Gln Lys Asn Tyr Leu Thr Trp Tyr
    50                  55                  60

Gln Gln Lys Pro Gly Gln Ser Pro Lys Leu Leu Ile Ser Trp Ala Ser
65                  70                  75                  80

Thr Arg Ala Ser Gly Val Pro Asp Arg Phe Thr Gly Ser Gly Ser Gly
                85                  90                  95

Thr Asp Phe Thr Leu Thr Ile Ser Ser Val Lys Ala Glu Asp Leu Gly
            100                 105                 110

Val Tyr Tyr Cys Gln Gln Tyr Phe Ile Tyr Pro Leu Thr Phe Gly Val
        115                 120                 125

Gly Thr Lys Leu Gly Leu Lys Gly Ser Ser Gly Ser Gly Lys Ser
    130                 135                 140

Ser Glu Gly Lys Gly Glu Val Lys Leu Glu Glu Ser Gly Pro Asp Leu
145                 150                 155                 160

Val Lys Pro Ser Gln Ser Leu Ser Leu Thr Cys Thr Val Thr Gly Tyr
                165                 170                 175

Ser Ile Thr Ser Gly Tyr Thr Trp His Trp Ile Arg Gln Phe Pro Gly
            180                 185                 190

Asn Thr Val Glu Trp Met Gly Tyr Ile Gln Tyr Thr Gly Ser Thr Arg
        195                 200                 205

Tyr Asn Pro Ala Leu Arg Gly Arg Leu Ser Ile Ser Arg Asp Thr Ser
    210                 215                 220

Lys Asn Gln Phe Phe Leu Gln Leu Ile Ser Val Thr Thr Ala Asp Thr
225                 230                 235                 240

Gly Thr Tyr Phe Cys Ala Arg Gly Thr Thr Ala Ser Phe Asp Tyr Trp
                245                 250                 255

Gly Gln Gly Thr Thr Leu Thr Val Ala Ser Leu Ser Asn Ser Ile Met
            260                 265                 270

Tyr Phe Ser His Phe Val Pro Val Phe Leu Pro Ala Lys Pro Thr Thr
        275                 280                 285

Thr Pro Ala Pro Arg Pro Pro Thr Pro Ala Pro Thr Ile Ala Ser Gln
    290                 295                 300

Pro Leu Ser Leu Arg Pro Glu Ala Cys Arg Pro Ala Ala Gly Gly Ala
305                 310                 315                 320

Val His Thr Arg Gly Leu Asp Phe Ala Cys Asp Ile Tyr Ile Trp Ala
                325                 330                 335

```
Pro Leu Ala Gly Thr Cys Gly Val Leu Leu Ser Leu Val Ile Thr
            340                 345                 350

Leu Tyr Cys Asn His Arg Ser Gln Val Arg Lys Ala Ala Ile Thr Ser
            355                 360                 365

Tyr Glu Lys Ser Asp Gly Val Tyr Thr Gly Leu Ser Thr Arg Asn Gln
            370                 375                 380

Glu Thr Tyr Glu Thr Leu Lys His Glu Lys Pro Pro Gln
385                 390                 395

<210> SEQ ID NO 13
<211> LENGTH: 354
<212> TYPE: PRT
<213> ORGANISM: Artificial Sequence
<220> FEATURE:
<223> OTHER INFORMATION: Synthesized

<400> SEQUENCE: 13

Met Asp Phe Gln Val Gln Ile Phe Ser Phe Leu Leu Ile Ser Ala Ser
1               5                   10                  15

Val Ile Met Ser Arg Gly Asp Ile Val Met Thr Gln Ser Pro Lys Phe
            20                  25                  30

Met Ser Thr Ser Val Gly Asp Arg Ile Ser Val Thr Cys Lys Ala Ser
        35                  40                  45

Gln Asp Val Gly Pro Asn Val Ala Trp Tyr Gln Gln Lys Pro Gly Gln
    50                  55                  60

Ser Pro Lys Pro Leu Ile Tyr Ser Ala Ser Tyr Leu Tyr Asn Gly Val
65                  70                  75                  80

Pro Asp Arg Phe Thr Gly Ser Gly Ser Gly Thr Asp Phe Ser Leu Thr
                85                  90                  95

Ile Ser Asn Val Gln Ser Asp Asp Leu Ala Glu Tyr Phe Cys Gln Gln
            100                 105                 110

Tyr Asn Thr Tyr Pro Phe Thr Phe Gly Gly Gly Thr Lys Leu Glu Ile
        115                 120                 125

Lys Gly Ser Thr Ser Gly Ser Gly Lys Ser Ser Glu Gly Lys Gly Glu
    130                 135                 140

Val Gln Leu Glu Glu Ser Gly Gly Gly Leu Val Gln Pro Lys Gly Ser
145                 150                 155                 160

Leu Lys Leu Ser Cys Ala Ala Ser Gly Phe Thr Phe Asn Thr Tyr Ala
                165                 170                 175

Met Asn Trp Val Arg Gln Ala Pro Gly Lys Gly Leu Glu Trp Ile Val
            180                 185                 190

Arg Ile Arg Ser Lys Ser Asn Asn Tyr Ala Thr Tyr Tyr Val Asp Ser
        195                 200                 205

Val Lys Asp Arg Phe Thr Ile Ser Arg Asp Asp Ser Gln Ser Met Leu
    210                 215                 220

Tyr Leu Gln Met Asn Asn Leu Lys Thr Glu Asp Thr Ala Met Tyr Tyr
225                 230                 235                 240

Cys Val Thr Ser Tyr Tyr Asp Tyr Asp Lys Val Leu Phe Ala Tyr Trp
                245                 250                 255

Gly Gln Gly Thr Thr Val Thr Val Lys Gly Ala Ala Ala Lys Gly Lys
            260                 265                 270

His Leu Cys Pro Ser Pro Leu Phe Pro Gly Pro Ser Lys Pro Phe Trp
        275                 280                 285

Val Leu Val Val Val Gly Gly Val Leu Ala Cys Tyr Ser Leu Leu Val
    290                 295                 300
```

Thr Val Ala Phe Ile Ile Phe Trp Val Arg Ser Lys Arg Ser Arg Leu
305                 310                 315                 320

Leu His Ser Asp Tyr Met Asn Met Thr Pro Arg Arg Pro Gly Pro Thr
            325                 330                 335

Arg Lys His Tyr Gln Pro Tyr Ala Pro Pro Arg Asp Phe Ala Ala Tyr
            340                 345                 350

Arg Ser

<210> SEQ ID NO 14
<211> LENGTH: 20
<212> TYPE: PRT
<213> ORGANISM: Artificial Sequence
<220> FEATURE:
<223> OTHER INFORMATION: Synthesized

<400> SEQUENCE: 14

Gly Ser Gly Glu Gly Arg Gly Ser Leu Leu Thr Cys Gly Asp Val Glu
1               5                   10                  15

Glu Asn Pro Gly
            20

<210> SEQ ID NO 15
<211> LENGTH: 63
<212> TYPE: DNA
<213> ORGANISM: Artificial Sequence
<220> FEATURE:
<223> OTHER INFORMATION: Synthesized

<400> SEQUENCE: 15
ggctccggag agggcagagg aagtcttcta acatgcggtg acgtggagga gaatcccggc      60
cct                                                                   63

<210> SEQ ID NO 16
<211> LENGTH: 729
<212> TYPE: DNA
<213> ORGANISM: Artificial Sequence
<220> FEATURE:
<223> OTHER INFORMATION: Synthesized

<400> SEQUENCE: 16
gatatccaga tgacacagag tacatcctcc ctgtctgcct ctctgggaga cagagtcacc      60
atcagttgca gtgcaagtca gggcattaac aattatttaa actggtatca gcagaaacca    120
gatggaactg ttgaactcct gatctattac acatcaactt tacagtcagg agtcccatca    180
aggttcagtg gcagtgggtc tgggacagat tattctctca ccatcagcaa cctggaacct    240
gaagatattg cacttacta ttgtcagcag tatagtaagc ttcctcggac gttcggtgga    300
ggcaccaagc tggaaatcaa aggtcgact tccggtagcg gcaaatcctc tgaaggcaaa    360
ggtcaggttc agctgcagca gtctggatct gagctgatga tgcctggggc ctcagtgaag    420
atatcctgca aggctactgg ctacacattc agtaactact ggatagagtg ggtaaagcag    480
aggcctggac atggccttga gtggattgga gagatttttac ctggaactgg tagaactatc    540
tacaatgaga gttcaagggg caaggccaca ttcactgcag atatatcctc caacacagtc    600
caaatgcaac tcagcagcct gacatctgag gactctgccg tctattactg tgcaagaagg    660
gactattatg gtaacttta ctatgctatg gactactggg gtcaagggac ctcagtcacc    720
gtctcctca                                                            729

<210> SEQ ID NO 17
<211> LENGTH: 798
<212> TYPE: DNA
<213> ORGANISM: Artificial Sequence
<220> FEATURE:
<223> OTHER INFORMATION: Synthesized

<400> SEQUENCE: 17

```
atggattttc aggtgcagat tttcagcttc ctgctaatca gtgcctcagt cataatgtct    60
agaggagata ttgtgatgac ccagtctcca aaattcatgt ccacatcagt aggagacagg   120
atcagcgtca cctgcaaggc cagtcaagat gtgggtccta atgtagcctg gtatcaacag   180
aaaccagggc aatctcctaa accactgatt tactcggcat cctacctata taatggagtc   240
cctgatcgct tcacaggcag tggatctggg acagatttct ctctcaccat cagcaatgtg   300
cagtctgatg acttggcaga gtatttctgt cagcaatata cacctatcc gttcacgttc    360
ggaggggggca ccaagctgga aatcaaaggg tcgacttccg gtagcggcaa atcctctgaa   420
ggcaaaggtg aggtgcagct ggaggagtct ggtggaggat tggtgcagcc taaagggtca   480
ttgaaactct catgtgcagc ctctggattc accttcaata cctacgccat gaactgggtc   540
cgccaggctc aggaaaaggg tttggaatgg attgttcgca taagaagtaa aagtaataat   600
tatgcaacat attatgtcga ttcagtgaaa gacaggttca ccatctccag agatgattca   660
caaagcatgc tctatctgca aatgaacaac ttgaaaactg aggacacagc catgtattac   720
tgtgtgactt cttactatga ttacgacaag gtcctgtttg cttactgggg ccaagggacc   780
acggtcaccg tgaaaggg                                                  798
```

<210> SEQ ID NO 18
<211> LENGTH: 798
<212> TYPE: DNA
<213> ORGANISM: Artificial Sequence
<220> FEATURE:
<223> OTHER INFORMATION: Synthesized

<400> SEQUENCE: 18

```
atggattttc aggtgcagat tttcagcttc ctgctaatca gtgcctcagt cataatgtct    60
agaggagaca ttgtgatgac ccagactcca tcctccctaa atgtgtcagt ggagagaag   120
gttactatga ggtgcaggtc cagtcagagc cttttatata gtagcgatca aaagaactac   180
ttgacctggt accagcagaa acctgggcag tctcctaaat tgctgatttc ctgggcatcc   240
actagggcat ctggggtccc tgatcgcttc acaggcagtg gatctgggac agatttcact   300
ctcaccatca gcagtgtgaa ggctgaagac ctggagtttt attactgtca acaatatttt   360
atctatccgc tcacgttcgg tgttgggacc aagctggggc tgaaagggtc gagttccggt   420
agcggcaaat cctctgaagg caaaggtgag gtaaagctgg aggagtctgg acctgacctg   480
gtgaaacctt ctcagtcact ttcgctcacc tgcaccgtca ctggctactc catcaccagt   540
ggttatacct ggcactggat ccggcagttt ccaggaaaca cagtgaatg gatgggctac   600
atacagtaca ctggttccac taggtacaac cccgctctca gaggtcgact ctctatcagt   660
cgagacacat ccaagaacca gttcttcctg cagttgattt ctgtgactac tgcggacaca   720
ggcacatatt tctgtgcaag gggtactacg gcctcctttg actactgggg ccaaggcacc   780
actctcacag tcgcctca                                                  798
```

<210> SEQ ID NO 19
<211> LENGTH: 120
<212> TYPE: DNA

<213> ORGANISM: Artificial Sequence
<220> FEATURE:
<223> OTHER INFORMATION: Synthesized

<400> SEQUENCE: 19

| | |
|---|---|
| agtaagagga gcaggctcct gcacagtgac tacatgaaca tgactccccg ccgccccggg | 60 |
| cccacccgca agcattacca gccctatgcc ccaccacgcg acttcgcagc ctatagatct | 120 |

<210> SEQ ID NO 20
<211> LENGTH: 130
<212> TYPE: DNA
<213> ORGANISM: Artificial Sequence
<220> FEATURE:
<223> OTHER INFORMATION: Synthesized

<400> SEQUENCE: 20

| | |
|---|---|
| agatctcaag tgcgaaaggc agctataacc agctatgaga aatcagatgg tgtttacacg | 60 |
| ggcctgagca ccaggaacca ggagacttac gagactctga agcatgagaa accaccacag | 120 |
| tagactcgag | 130 |

<210> SEQ ID NO 21
<211> LENGTH: 2323
<212> TYPE: DNA
<213> ORGANISM: Artificial Sequence
<220> FEATURE:
<223> OTHER INFORMATION: Synthesized

<400> SEQUENCE: 21

| | |
|---|---|
| atggattttc aggtgcagat tttcagcttc ctgctaatca gtgcctcagt cataatgtcc | 60 |
| agaggagata tccagatgac acagagtaca tcctccctgt ctgcctctct gggagacaga | 120 |
| gtcaccatca gttgcagtgc aagtcagggc attaacaatt atttaaactg gtatcagcag | 180 |
| aaaccagatg gaactgttga actcctgatc tattacacat caactttaca gtcaggagtc | 240 |
| ccatcaaggt tcagtggcag tgggtctggg acagattatt ctctcaccat cagcaacctg | 300 |
| gaacctgaag atattggcac ttactattgt cagcagtata gtaagcttcc tcggacgttc | 360 |
| ggtggaggca ccaagctgga aatcaaaggg tcgacttccg gtagcggcaa atcctctgaa | 420 |
| ggcaaaggtc aggttcagct gcagcagtct ggatctgagc tgatgatgcc tggggcctca | 480 |
| gtgaagatat cctgcaaggc tactggctac acattcagta actactggat agagtgggta | 540 |
| aagcagaggc ctggacatgg ccttgagtgg attggagaga ttttacctgg aactggtaga | 600 |
| actatctcac atgagaagtt caagggcaag gccacattca ctgcagatat atcctccaac | 660 |
| acagtccaaa tgcaactcag cagcctgaca tctgaggact ctgccgtcta ttactgtgca | 720 |
| agaagggact attatggtaa cttttactat gctatggact actggggtca agggacctca | 780 |
| gtcaccgtct cctcagcggc cgcaaaaggg aaacaccttt gtccaagtcc cctatttccc | 840 |
| ggaccttcta gcccttttg gtgctggtg tggttggtg gagtcctggc ttgctatagc | 900 |
| ttgctagtaa cagtggcctt tattattttc tgggtgagga gtaagaggag caggctcctg | 960 |
| cacagtgact acatgaacat gactccccgc cgccccgggc ccacccgcaa gcattaccag | 1020 |
| ccctatgccc caccacgcga cttcgcagcc tatagatctg gctccggaga gggcagagga | 1080 |
| agtcttctaa catgcggtga cgtggaggag aatcccggcc cttacgtaat ggattttcag | 1140 |
| gtgcagattt tcagcttcct gctaatcagt gcctcagtca taatgtctag aggagatatt | 1200 |
| gtgatgaccc agtctccaaa attcatgtcc acatcagtag gagacaggat cagcgtcacc | 1260 |
| tgcaaggcca gtcaagatgt gggtcctaat gtagcctggt atcaacagaa accagggcaa | 1320 |

```
tctcctaaac cactgattta ctcggcatcc tacctatata atggagtccc tgatcgcttc      1380
acaggcagtg gatctgggac agatttctct ctcaccatca gcaatgtgca gtctgatgac      1440
ttggcagagt atttctgtca gcaatataac acctatccgt tcacgttcgg agggggcacc      1500
aagctggaaa tcaaagggtc gacttccggt agcggcaaat cctctgaagg caaaggtgag      1560
gtgcagctgg aggagtctgg tggaggattg gtgcagccta aagggtcatt gaaactctca      1620
tgtgcagcct ctggattcac cttcaatacc tacgccatga actgggtccg ccaggctcca      1680
ggaaagggtt tggaatggat tgttcgcata agaagtaaaa gtaataatta tgcaacatat      1740
tatgtcgatt cagtgaaaga caggttcacc atctccagag atgattcaca aagcatgctc      1800
tatctgcaaa tgaacaactt gaaaactgag gacacagcca tgtattactg tgtgacttct      1860
tactatgatt acgacaaggt cctgtttgct tactgggggcc aagggaccac ggtcaccgtg      1920
aaagggctga gcaactccat catgtacttc agccacttcg tgccggtctt cctgccagcg      1980
aagcccacca cgacgccagc gccgcgacca ccaacaccgg cgcccaccat cgcgtcgcag      2040
cccctgtccc tgcgcccaga ggcgtgccgg ccagcggcgg ggggcgcagt gcacacgagg      2100
gggctggact cgcctgtga tatctacatc tgggcgccct tggccgggac ttgtggggtc      2160
cttctcctgt cactggttat cacccttttac tgcaaccaca gatctcaagt gcgaaaggca      2220
gctataacca gctatgagaa atcagatggt gtttacacgg gcctgagcac caggaaccag      2280
gagacttacg agactctgaa gcatgagaaa ccaccacagt aga                        2323

<210> SEQ ID NO 22
<211> LENGTH: 2323
<212> TYPE: DNA
<213> ORGANISM: artificial sequence
<220> FEATURE:
<223> OTHER INFORMATION: Synthesized

<400> SEQUENCE: 22
atggattttc aggtgcagat tttcagcttc ctgctaatca gtgcctcagt cataatgtcc       60
agaggagata tccagatgac acagagtaca tcctccctgt ctgcctctct gggagacaga      120
gtcaccatca gttgcagtgc aagtcagggc attaacaatt atttaaactg gtatcagcag      180
aaaccagatg gaactgttga actcctgatc tattacacat caactttaca gtcaggagtc      240
ccatcaaggt tcagtggcag tgggtctggg acagattatt ctctcaccat cagcaacctg      300
gaacctgaag atattggcac ttactattgt cagcagtata gtaagcttcc tcggacgttc      360
ggtggaggca ccaagctgga aatcaaaggg tcgacttccg gtagcggcaa atcctctgaa      420
ggcaaaggtc aggttcagct gcagcagtct ggatctgagc tgatgatgcc tggggcctca      480
gtgaagatat cctgcaaggc tactggctac acattcagta actactggat agagtgggta      540
aagcagaggc ctggacatgg ccttgagtgg attggagaga ttttacctgg aactggtaga      600
actatctaca tgagaagtt caagggcaag gccacattca ctgcagatat atcctccaac      660
acagtccaaa tgcaactcag cagcctgaca tctgaggact ctgccgtcta ttactgtgca      720
agaagggact attatggtaa cttttactat gctatggact actggggtca agggacctca      780
gtcaccgtct cctcagcggc cgcaaaaggg aacacccttt gtccaagtcc ctatttccc      840 ggaccttcta agcccttttg ggtgctggtg gtggttggtg gagtcctggc ttgctatagc      900
ttgctagtaa cagtggcctt tattattttc tgggtgagga gtaagaggag caggctcctg      960
cacagtgact acatgaacat gactccccgc cgccccgggc ccacccgcaa gcattaccag     1020
```

```
cccuatgccc caccacgcga cttcgcagcc tatagatctg gctccggaga gggcagagga    1080
agtcttctaa catgcggtga cgtggaggag aatcccggcc cttacgtaat ggattttcag    1140
gtgcagattt tcagcttcct gctaatcagt gcctcagtca taatgtctag aggagacatt    1200
gtgatgaccc agactccatc ctccctaaat gtgtcagttg gagagaaggt tactatgagg    1260
tgcaggtcca gtcagagcct tttatatagt agcgatcaaa agaactactt gacctggtac    1320
cagcagaaac ctgggcagtc tcctaaattg ctgatttcct gggcatccac tagggcatct    1380
ggggtccctg atcgcttcac aggcagtgga tctgggacag atttcactct caccatcagc    1440
agtgtgaagg ctgaagacct gggagtttat tactgtcaac aatattttat ctatccgctc    1500
acgttcggtg ttgggaccaa gctggggctg aaagggtcga gttccggtag cggcaaatcc    1560
tctgaaggca aaggtgaggt aaagctggag gagtctggac ctgacctggt gaaaccttct    1620
cagtcacttt cgctcacctg caccgtcact ggctactcca tcaccagtgg ttatacctgg    1680
cactggatcc ggcagtttcc aggaaacaca gtggaatgga tgggctacat acagtacact    1740
ggttccacta ggtacaaccc cgctctcaga ggtcgactct ctatcagtcg agacacatcc    1800
aagaaccagt tcttcctgca gttgatttct gtgactactg cggacacagg cacatatttc    1860
tgtgcaaggg gtactacggc ctcctttgac tactggggcc aaggcaccac tctcacagtc    1920
gcctcactga gcaactccat catgtacttc agccacttcg tgccggtctt cctgccagcg    1980
aagcccacca cgacgccagc gccgcgacca ccaacaccgg cgccaccat cgcgtcgcag    2040 cccctgtccc tgcgcccaga ggcgtgccgg ccagcggcgg ggggcgcagt gcacacgagg    2100
gggctggact tcgcctgtga tatctacatc tgggcgccct tggccgggac ttgtggggtc    2160
cttctcctgt cactggttat caccctttac tgcaaccaca gatctcaagt gcgaaaggca    2220
gctataacca gctatgagaa atcagatggt gtttacacgg gcctgagcac caggaaccag    2280
gagacttacg agactctgaa gcatgagaaa ccaccacagt aga                     2323
```

<210> SEQ ID NO 23
<211> LENGTH: 2326
<212> TYPE: DNA
<213> ORGANISM: artificial sequence
<220> FEATURE:
<223> OTHER INFORMATION: Synthesized

<400> SEQUENCE: 23

```
atggattttc aggtgcagat tttcagcttc ctgctaatca gtgcctcagt cataatgtct    60
agaggagata ttgtgatgac ccagtctcca aaattcatgt ccacatcagt aggagacagg    120
atcagcgtca cctgcaaggc cagtcaagat gtgggtccta atgtagcctg gtatcaacag    180
aaaccagggc aatctcctaa accactgatt tactcggcat cctacctata taatggagtc    240
cctgatcgct tcacaggcag tggatctggg acagatttct ctctcaccat cagcaatgtg    300
cagtctgatg acttggcaga gtatttctgt cagcaatata cacctatcc gttcacgttc    360 ggaggggca ccaagctgga aatcaaaggg tcgacttccg gtagcggcaa atcctctgaa    420
ggcaaaggtg aggtgcagct ggaggagtct ggtggaggat tggtgcagcc taaagggtca    480
ttgaaactct catgtgcagc ctctggattc accttcaata cctacgccat gaactgggtc    540
cgccaggctc aggaaaggg tttggaatgg attgttcgca taagaagtaa aagtaataat    600
tatgcaacat attatgtcga ttcagtgaaa gacaggttca ccatctccag agatgattca    660
caaagcatgc tctatctgca aatgaacaac ttgaaaactg aggacacagc catgtattac    720
tgtgtgactt cttactatga ttacgacaag gtcctgtttg cttactgggg ccaagggacc    780
```

```
acggtcaccg tgaaaggggc ggccgcaaaa gggaaacacc tttgtccaag tcccctattt      840
cccggacctt ctaagccctt ttgggtgctg gtggtggttg gtggagtcct ggcttgctat      900
agcttgctag taacagtggc ctttattatt ttctgggtga ggagtaagag gagcaggctc      960
ctgcacagtg actacatgaa catgactccc cgccgccccg ggcccacccg caagcattac     1020
cagccctatg ccccaccacg cgacttcgca gcctatagat ctggctccgg agagggcaga     1080
ggaagtcttc taacatgcgg tgacgtggag gagaatcccg gcccttacgt aatggatttt     1140
caggtgcaga ttttcagctt cctgctaatc agtgcctcag tcataatgtc tagaggagac     1200
attgtgatga cccagactcc atcctcccta aatgtgtcag ttggagagaa ggttactatg     1260
aggtgcaggt ccagtcagag cctttatat agtagcgatc aaaagaacta cttgacctgg     1320
taccagcaga aacctgggca gtctcctaaa ttgctgattt cctgggcatc cactagggca     1380
tctggggtcc ctgatcgctt cacaggcagt ggatctggga cagatttcac tctcaccatc     1440
agcagtgtga aggctgaaga cctgggagtt tattactgtc aacatattt tatctatccg     1500 ctcacgttcg gtgttgggac caagctgggg ctgaaagggt cgagttccgg tagcggcaaa     1560
tcctctgaag gcaaaggtga ggtaaagctg gaggagtctg gacctgacct ggtgaaacct     1620
tctcagtcac tttcgctcac ctgcaccgtc actggctact ccatcaccag tggttatacc     1680
tggcactgga tccggcagtt tccaggaaac acagtggaat ggatgggcta catacagtac     1740
actggttcca ctaggtacaa ccccgctctc agaggtcgac tctctatcag tcgagacaca     1800
tccaagaacc agttcttcct gcagttgatt tctgtgacta ctgcggacac aggcacatat     1860
ttctgtgcaa ggggtactac ggcctccttt gactactggg gccaaggcac cactctcaca     1920
gtcgcctcac tgagcaactc catcatgtac ttcagccact tcgtgccggt cttcctgcca     1980
gcgaagccca ccacgacgcc agcgccgcga ccaccaacac cggcgcccac catcgcgtcg     2040
cagcccctgt ccctgcgccc agaggcgtgc cggccagcgg cggggggcgc agtgcacacg     2100
agggggctgg acttcgcctg tgatatctac atctgggcgc ccttggccgg acttgtggg      2160 gtccttctcc tgtcactggt tatcacccct tactgcaacc acagatctca agtgcgaaag     2220
gcagctataa ccagctatga gaatcagat ggtgtttaca cgggcctgag caccaggaac     2280
caggagactt acgagactct gaagcatgag aaaccaccac agtaga                    2326
```

<210> SEQ ID NO 24
<211> LENGTH: 1059
<212> TYPE: DNA
<213> ORGANISM: Artificial Sequence
<220> FEATURE:
<223> OTHER INFORMATION: Synthesized

<400> SEQUENCE: 24

```
atggattttc aggtgcagat tttcagcttc ctgctaatca gtgcctcagt cataatgtcc       60
agaggagata tccagatgac acagagtaca tcctccctgt ctgcctctct gggagacaga      120
gtcaccatca gttgcagtgc aagtcagggc attaacaatt atttaaactg gtatcagcag      180
aaaccagatg gaactgttga actcctgatc tattacacat caactttaca gtcaggagtc      240
ccatcaaggt tcagtggcag tgggtctggg acagattatt ctctcaccat cagcaacctg      300
gaacctgaag atattggcac ttactattgt cagcagtata gtaagcttcc tcggacgttc      360
ggtggaggca ccaagctgga aatcaaaggg tcgacttccg gtagcggcaa atcctctgaa      420
ggcaaaggtc aggttcagct gcagcagtct ggatctgagc tgatgatgcc tggggcctca      480
```

| | | |
|---|---|---|
| gtgaagatat cctgcaaggc tactggctac acattcagta actactggat agagtgggta | 540 | |
| aagcagaggc ctggacatgg ccttgagtgg attggagaga ttttacctgg aactggtaga | 600 | |
| actatctaca atgagaagtt caagggcaag gccacattca ctgcagatat atcctccaac | 660 | |
| acagtccaaa tgcaactcag cagcctgaca tctgaggact ctgccgtcta ttactgtgca | 720 | |
| agaagggact attatggtaa cttttactat gctatggact actggggtca agggacctca | 780 | |
| gtcaccgtct cctcagcggc cgcaaaaggg aaacaccttt gtccaagtcc cctatttccc | 840 | |
| ggaccttcta agccctttg ggtgctggtg gtggttggtg gagtcctggc ttgctatagc | 900 | |
| ttgctagtaa cagtggcctt tattattttc tgggtgagga gtaagaggag caggctcctg | 960 | |
| cacagtgact acatgaacat gactccccgc cgccccgggc ccacccgcaa gcattaccag | 1020 | |
| ccctatgccc caccacgcga cttcgcagcc tatagatct | 1059 | |

<210> SEQ ID NO 25
<211> LENGTH: 1195
<212> TYPE: DNA
<213> ORGANISM: Artificial Sequence
<220> FEATURE:
<223> OTHER INFORMATION: Synthesized

<400> SEQUENCE: 25

| | | |
|---|---|---|
| atggattttc aggtgcagat tttcagcttc ctgctaatca gtgcctcagt cataatgtct | 60 | |
| agaggagata ttgtgatgac ccagtctcca aaattcatgt ccacatcagt aggagacagg | 120 | |
| atcagcgtca cctgcaaggc cagtcaagat gtgggtccta atgtagcctg gtatcaacag | 180 | |
| aaaccagggc aatctcctaa accactgatt tactcggcat cctacctata taatggagtc | 240 | |
| cctgatcgct tcacaggcag tggatctggg acagatttct ctctcaccat cagcaatgtg | 300 | |
| cagtctgatg acttggcaga gtatttctgt cagcaatata cacctatcc gttcacgttc | 360 | |
| ggaggggggca ccaagctgga aatcaaaggg tcgacttccg gtagcggcaa atcctctgaa | 420 | |
| ggcaaaggtg aggtgcagct ggaggagtct ggtggaggat tggtgcagcc taaagggtca | 480 | |
| ttgaaactct catgtgcagc ctctggattc accttcaata cctacgccat gaactgggtc | 540 | |
| cgccaggctc caggaaaggg tttggaatgg attgttcgca taagaagtaa aagtaataat | 600 | |
| tatgcaacat attatgtcga ttcagtgaaa gacaggttca ccatctccag agatgattca | 660 | |
| caaagcatgc tctatctgca aatgaacaac ttgaaaactg aggacacagc catgtattac | 720 | |
| tgtgtgactt cttactatga ttacgacaag gtcctgtttg cttactgggg ccaagggacc | 780 | |
| acggtcaccg tgaaagggct gagcaactcc atcatgtact tcagccactt cgtgccggtc | 840 | |
| ttcctgccag cgaagcccac cacgacgcca gcgccgcgac caccaacacc ggcgcccacc | 900 | |
| atcgcgtcgc agcccctgtc cctgcgccca gaggcgtgcc ggccagcggc ggggggcgca | 960 | |
| gtgcacacga ggggctgga cttcgcctgt gatatctaca tctgggcgcc cttggccggg | 1020 | |
| acttgtgggg tccttctcct gtcactggtt atcaccctt actgcaacca cagatctcaa | 1080 | |
| gtgcgaaagg cagctataac cagctatgag aaatcagatg gtgtttacac gggcctgagc | 1140 | |
| accaggaacc aggagactta cgagactctg aagcatgaga aaccaccaca gtaga | 1195 | |

<210> SEQ ID NO 26
<211> LENGTH: 1195
<212> TYPE: DNA
<213> ORGANISM: Artificial Sequence
<220> FEATURE:
<223> OTHER INFORMATION: Synthesized

<400> SEQUENCE: 26

```
atggattttc aggtgcagat tttcagcttc ctgctaatca gtgcctcagt cataatgtct    60
agaggagaca ttgtgatgac ccagactcca tcctccctaa atgtgtcagt tggagagaag   120
gttactatga ggtgcaggtc cagtcagagc ctttatata gtagcgatca aaagaactac   180
ttgacctggt accagcagaa acctgggcag tctcctaaat tgctgatttc ctgggcatcc   240
actagggcat ctggggtccc tgatcgcttc acaggcagtg gatctgggac agatttcact   300
ctcaccatca gcagtgtgaa ggctgaagac ctggagtttt attactgtca acaatatttt   360
atctatccgc tcacgttcgg tgttgggacc aagctggggc tgaaagggtc gagttccggt   420
agcggcaaat cctctgaagg caaaggtgag gtaaagctgg aggagtctgg acctgacctg   480
gtgaaacctt ctcagtcact ttcgctcacc tgcaccgtca ctggctactc catcaccagt   540
ggttatacct ggcactggat ccggcagttt ccaggaaaca cagtggaatg gatgggctac   600
atacagtaca ctggttccac taggtacaac cccgctctca gaggtcgact ctctatcagt   660
cgagacacat ccaagaacca gttcttcctg cagttgattt ctgtgactac tgcggacaca   720
ggcacatatt tctgtgcaag gggtactacg gcctcctttg actactgggg ccaaggcacc   780
actctcacag tcgcctcact gagcaactcc atcatgtact tcagccactt cgtgccggtc   840
ttcctgccag cgaagcccac cacgacgcca gcgccgcgac caccaacacc ggcgcccacc   900
atcgcgtcgc agcccctgtc cctgcgccca gaggcgtgcc ggccagcggc gggggggcgca   960 gtgcacacga gggggctgga cttcgcctgt gatatctaca tctgggcgcc cttggccggg  1020
acttgtgggg tccttctcct gtcactggtt atcacccttt actgcaacca cagatctcaa  1080
gtgcgaaagg cagctataac cagctatgag aaatcagatg gtgtttacac gggcctgagc  1140
accaggaacc aggagactta cgagactctg aagcatgaga accaccaca gtaga       1195

<210> SEQ ID NO 27
<211> LENGTH: 1062
<212> TYPE: DNA
<213> ORGANISM: Artificial Sequence
<220> FEATURE:
<223> OTHER INFORMATION: Synthesized

<400> SEQUENCE: 27
atggattttc aggtgcagat tttcagcttc ctgctaatca gtgcctcagt cataatgtct    60
agaggagata ttgtgatgac ccagtctcca aaattcatgt ccacatcagt aggagacagg   120
atcagcgtca cctgcaaggc cagtcaagat gtgggtccta atgtagcctg gtatcaacag   180
aaaccagggc aatctcctaa accactgatt tactcggcat cctacctata taatggagtc   240
cctgatcgct tcacaggcag tggatctggg acagatttct ctctcaccat cagcaatgtg   300
cagtctgatg acttggcaga gtatttctgt cagcaatata cacctatcc gttcacgttc   360 ggaggggca ccaagctgga aatcaaaggg tcgacttccg gtagcggcaa atcctctgaa   420
ggcaaaggtg aggtgcagct ggaggagtct ggtggaggat tggtgcagcc taaagggtca   480
ttgaaactct catgtgcagc ctctggattc accttcaata cctacgccat gaactgggtc   540
cgccaggctc caggaaaggg tttggaatgg attgttcgca taagaagtaa aagtaataat   600
tatgcaacat attatgtcga ttcagtgaaa gacaggttcc catctccag agatgattca   660 caaagcatgc tctatctgca aatgaacaac ttgaaaactg aggacacagc catgtattac   720
tgtgtgactt cttactatga ttacgacaag gtcctgtttg cttactgggg ccaagggacc   780
acggtcaccg tgaagggggc ggccgcaaaa gggaaacacc tttgtccaag tcccctattt   840
```

```
cccggacctt ctaagcccttt ttgggtgctg gtggtggttg gtggagtcct ggcttgctat    900
agcttgctag taacagtggc ctttattatt ttctgggtga ggagtaagag gagcaggctc    960
ctgcacagtg actacatgaa catgactccc cgccgccccg ggcccacccg caagcattac   1020
cagccctatg ccccaccacg cgacttcgca gcctatagat ct                      1062
```

<210> SEQ ID NO 28
<211> LENGTH: 243
<212> TYPE: PRT
<213> ORGANISM: Artificial Sequence
<220> FEATURE:
<223> OTHER INFORMATION: Synthesized

<400> SEQUENCE: 28

```
Asp Ile Gln Met Thr Gln Ser Thr Ser Ser Leu Ser Ala Ser Leu Gly
1               5                   10                  15

Asp Arg Val Thr Ile Ser Cys Ser Ala Ser Gln Gly Ile Asn Asn Tyr
            20                  25                  30

Leu Asn Trp Tyr Gln Gln Lys Pro Asp Gly Thr Val Glu Leu Leu Ile
        35                  40                  45

Tyr Tyr Thr Ser Thr Leu Gln Ser Gly Val Pro Ser Arg Phe Ser Gly
50                  55                  60

Ser Gly Ser Gly Thr Asp Tyr Ser Leu Thr Ile Ser Asn Leu Glu Pro
65                  70                  75                  80

Glu Asp Ile Gly Thr Tyr Tyr Cys Gln Gln Tyr Ser Lys Leu Pro Arg
                85                  90                  95

Thr Phe Gly Gly Gly Thr Lys Leu Glu Ile Lys Gly Ser Thr Ser Gly
            100                 105                 110

Ser Gly Lys Ser Ser Glu Gly Lys Gly Gln Val Gln Leu Gln Gln Ser
        115                 120                 125

Gly Ser Glu Leu Met Met Pro Gly Ala Ser Val Lys Ile Ser Cys Lys
130                 135                 140

Ala Thr Gly Tyr Thr Phe Ser Asn Tyr Trp Ile Glu Trp Val Lys Gln
145                 150                 155                 160

Arg Pro Gly His Gly Leu Glu Trp Ile Gly Glu Ile Leu Pro Gly Thr
                165                 170                 175

Gly Arg Thr Ile Tyr Asn Glu Lys Phe Lys Gly Lys Ala Thr Phe Thr
            180                 185                 190

Ala Asp Ile Ser Ser Asn Thr Val Gln Met Gln Leu Ser Ser Leu Thr
        195                 200                 205

Ser Glu Asp Ser Ala Val Tyr Tyr Cys Ala Arg Arg Asp Tyr Tyr Gly
    210                 215                 220

Asn Phe Tyr Tyr Ala Met Asp Tyr Trp Gly Gln Gly Thr Ser Val Thr
225                 230                 235                 240

Val Ser Ser
```

<210> SEQ ID NO 29
<211> LENGTH: 244
<212> TYPE: PRT
<213> ORGANISM: Artificial Sequence
<220> FEATURE:
<223> OTHER INFORMATION: Synthesized

<400> SEQUENCE: 29

```
Asp Ile Val Met Thr Gln Ser Pro Lys Phe Met Ser Thr Ser Val Gly
1               5                   10                  15

Asp Arg Ile Ser Val Thr Cys Lys Ala Ser Gln Asp Val Gly Pro Asn
```

```
            20                  25                  30
Val Ala Trp Tyr Gln Gln Lys Pro Gly Gln Ser Pro Lys Pro Leu Ile
        35                  40                  45
Tyr Ser Ala Ser Tyr Leu Tyr Asn Gly Val Pro Asp Arg Phe Thr Gly
    50                  55                  60
Ser Gly Ser Gly Thr Asp Phe Ser Leu Thr Ile Ser Asn Val Gln Ser
65                  70                  75                  80
Asp Asp Leu Ala Glu Tyr Phe Cys Gln Gln Tyr Asn Thr Tyr Pro Phe
                85                  90                  95
Thr Phe Gly Gly Gly Thr Lys Leu Glu Ile Lys Gly Ser Thr Ser Gly
            100                 105                 110
Ser Gly Lys Ser Ser Glu Gly Lys Gly Val Gln Leu Glu Glu Ser
        115                 120                 125
Gly Gly Gly Leu Val Gln Pro Lys Gly Ser Leu Lys Leu Ser Cys Ala
    130                 135                 140
Ala Ser Gly Phe Thr Phe Asn Thr Tyr Ala Met Asn Trp Val Arg Gln
145                 150                 155                 160
Ala Pro Gly Lys Gly Leu Glu Trp Ile Val Arg Ile Arg Ser Lys Ser
                165                 170                 175
Asn Asn Tyr Ala Thr Tyr Tyr Val Asp Ser Val Lys Asp Arg Phe Thr
            180                 185                 190
Ile Ser Arg Asp Asp Ser Gln Ser Met Leu Tyr Leu Gln Met Asn Asn
        195                 200                 205
Leu Lys Thr Glu Asp Thr Ala Met Tyr Cys Val Thr Ser Tyr Tyr
    210                 215                 220
Asp Tyr Asp Lys Val Leu Phe Ala Tyr Trp Gly Gln Gly Thr Thr Val
225                 230                 235                 240
Thr Val Lys Gly
```

<210> SEQ ID NO 30
<211> LENGTH: 22
<212> TYPE: PRT
<213> ORGANISM: Artificial Sequence
<220> FEATURE:
<223> OTHER INFORMATION: Synthesized

<400> SEQUENCE: 30

```
Met Asp Phe Gln Val Gln Ile Phe Ser Phe Leu Leu Ile Ser Ala Ser
1               5                   10                  15
Val Ile Met Ser Arg Gly
            20
```

<210> SEQ ID NO 31
<211> LENGTH: 45
<212> TYPE: PRT
<213> ORGANISM: Artificial Sequence
<220> FEATURE:
<223> OTHER INFORMATION: Synthesized

<400> SEQUENCE: 31

```
Lys Gly Lys His Leu Cys Pro Ser Pro Leu Phe Pro Gly Pro Ser Lys
1               5                   10                  15
Pro Phe Trp Val Leu Val Val Gly Gly Val Leu Ala Cys Tyr Ser
                20                  25                  30
Leu Leu Val Thr Val Ala Phe Ile Ile Phe Trp Val Arg
            35                  40                  45
```

<210> SEQ ID NO 32
<211> LENGTH: 91
<212> TYPE: PRT
<213> ORGANISM: Artificial Sequence
<220> FEATURE:
<223> OTHER INFORMATION: Synthesized

<400> SEQUENCE: 32

```
Leu Ser Asn Ser Ile Met Tyr Phe Ser His Phe Val Pro Val Phe Leu
1               5                   10                  15

Pro Ala Lys Pro Thr Thr Thr Pro Ala Pro Arg Pro Pro Thr Pro Ala
            20                  25                  30

Pro Thr Ile Ala Ser Gln Pro Leu Ser Leu Arg Pro Glu Ala Cys Arg
        35                  40                  45

Pro Ala Ala Gly Gly Ala Val His Thr Arg Gly Leu Asp Phe Ala Cys
    50                  55                  60

Asp Ile Tyr Ile Trp Ala Pro Leu Ala Gly Thr Cys Gly Val Leu Leu
65                  70                  75                  80

Leu Ser Leu Val Ile Thr Leu Tyr Cys Asn His
                85                  90
```

<210> SEQ ID NO 33
<211> LENGTH: 244
<212> TYPE: PRT
<213> ORGANISM: Artificial Sequence
<220> FEATURE:
<223> OTHER INFORMATION: Synthesized

<400> SEQUENCE: 33

```
Asp Ile Val Met Thr Gln Thr Pro Ser Ser Leu Asn Val Ser Val Gly
1               5                   10                  15

Glu Lys Val Thr Met Arg Cys Arg Ser Ser Gln Ser Leu Leu Tyr Ser
            20                  25                  30

Ser Asp Gln Lys Asn Tyr Leu Thr Trp Tyr Gln Gln Lys Pro Gly Gln
        35                  40                  45

Ser Pro Lys Leu Leu Ile Ser Trp Ala Ser Thr Arg Ala Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Gly Val Tyr Tyr Cys Gln Gln
                85                  90                  95

Tyr Phe Ile Tyr Pro Leu Thr Phe Gly Val Gly Thr Lys Leu Gly Leu
            100                 105                 110

Lys Gly Ser Ser Ser Gly Ser Gly Lys Ser Ser Glu Gly Lys Gly Glu
        115                 120                 125

Val Lys Leu Glu Glu Ser Gly Pro Asp Leu Val Lys Pro Ser Gln Ser
    130                 135                 140

Leu Ser Leu Thr Cys Thr Val Thr Gly Tyr Ser Ile Thr Ser Gly Tyr
145                 150                 155                 160

Thr Trp His Trp Ile Arg Gln Phe Pro Gly Asn Thr Val Glu Trp Met
                165                 170                 175

Gly Tyr Ile Gln Tyr Thr Gly Ser Thr Arg Tyr Asn Pro Ala Leu Arg
            180                 185                 190

Gly Arg Leu Ser Ile Ser Arg Asp Thr Ser Lys Asn Gln Phe Phe Leu
        195                 200                 205

Gln Leu Ile Ser Val Thr Thr Ala Asp Thr Gly Thr Tyr Phe Cys Ala
    210                 215                 220
```

```
Arg Gly Thr Thr Ala Ser Phe Asp Tyr Trp Gly Gln Gly Thr Thr Leu
225                 230                 235                 240

Thr Val Ala Ser

<210> SEQ ID NO 34
<211> LENGTH: 134
<212> TYPE: DNA
<213> ORGANISM: Artificial Sequence
<220> FEATURE:
<223> OTHER INFORMATION: Synthesized

<400> SEQUENCE: 34
aaagggaaac acctttgtcc aagtcccta tttcccggac cttctaagcc cttttgggtg      60
ctggtggtgg ttggtggagt cctggcttgc tatagcttgc tagtaacagt ggcctttatt    120
attttctggg tgag                                                      134

<210> SEQ ID NO 35
<211> LENGTH: 273
<212> TYPE: DNA
<213> ORGANISM: Artificial Sequence
<220> FEATURE:
<223> OTHER INFORMATION: Synthesized

<400> SEQUENCE: 35
ctgagcaact ccatcatgta cttcagccac ttcgtgccgg tcttcctgcc agcgaagccc      60
accacgacgc cagcgccgcg accaccaaca ccggcgccca ccatcgcgtc gcagcccctg    120
tccctgcgcc cagaggcgtg ccggccagcg gcggggggcg cagtgcacac gagggggctg    180
gacttcgcct gtgatatcta catctgggcg cccttggccg ggacttgtgg ggtccttctc    240
ctgtcactgg ttatcaccct ttactgcaac cac                                 273

<210> SEQ ID NO 36
<211> LENGTH: 13
<212> TYPE: PRT
<213> ORGANISM: Artificial Sequence
<220> FEATURE:
<223> OTHER INFORMATION: Synthesized

<400> SEQUENCE: 36

Gly Ser Ser Ser Gly Ser Gly Lys Ser Ser Glu Gly Lys
1               5                   10

<210> SEQ ID NO 37
<211> LENGTH: 66
<212> TYPE: DNA
<213> ORGANISM: Artificial Sequence
<220> FEATURE:
<223> OTHER INFORMATION: Synthesized

<400> SEQUENCE: 37
atggattttc aggtgcagat tttcagcttc ctgctaatca gtgcctcagt cataatgtcc      60
agagga                                                                66
```